(12) United States Patent
Usmani-Brown

(10) Patent No.: US 10,508,308 B2
(45) Date of Patent: Dec. 17, 2019

(54) ASSAYS FOR DIAGNOSING TYPE 1 DIABETES

(71) Applicant: L2 Diagnostics, LLC, New Haven, CT (US)

(72) Inventor: Sahar Usmani-Brown, New Haven, CT (US)

(73) Assignee: L2 Disgnostics, LLC, New Haven, CT (US)

( * ) Notice: Subject to any disclaimer, the term of this patent is extended or adjusted under 35 U.S.C. 154(b) by 0 days.

(21) Appl. No.: 15/784,650

(22) Filed: Oct. 16, 2017

(65) Prior Publication Data
US 2018/0195125 A1    Jul. 12, 2018

Related U.S. Application Data

(63) Continuation-in-part of application No. 14/490,333, filed on Sep. 18, 2014.

(60) Provisional application No. 61/879,347, filed on Sep. 18, 2013.

(51) Int. Cl.
*C12Q 1/68* (2018.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 10,125,394 B2 | 11/2018 | Herold et al. | |
| 2011/0077215 A1* | 3/2011 | Yu | A61K 31/7072 514/46 |
| 2013/0230850 A1 | 9/2013 | Akirav | |
| 2014/0178348 A1* | 6/2014 | Kelsey | C12Q 1/6886 424/93.71 |
| 2016/0273051 A1* | 9/2016 | Hayashi | C12Q 1/6886 |
| 2018/0195125 A1 | 7/2018 | Usmani-Brown | |

FOREIGN PATENT DOCUMENTS

| WO | WO 2012-112970 A2 * | 8/2012 |
| WO | WO-2012/112970 A2 | 8/2012 |
| WO | WO-2012178007 A1 | 12/2012 |

OTHER PUBLICATIONS

Dos Santos et al. Diabetes. 2009. 58: 489-492.*
Akirav, et al. Detection of beta cell death in diabetes using differentially methylated circulating DNA, PNAS, 108(47): 19018-19023 (2011).
Fisher, et al. "Detection of islet beta cell death in vivo by multiplex PCR analysis of differentially methylated DNA," Endocrinology, 154(9): 3476-3481 (Jul. 3, 2013).
Husseiny, et al. "Development of a quantitative methylation-specific polymerase chain reaction method for monitoring beta cell death in type 1 diabetes," PloS One, 7(10): e47942 (internal pp. 1-11) (2012).
ISR for PCT/US2014/056355 mailed Dec. 15, 2014.
Li et al., "MethPrimer: designing primers for methylation PCRs," Bioinformatics, 18:1427-1431 (2002).
NCBI Database, GenBank Accession No. J00265.1, Feb. 12, 2001.
Wilson et al., "A novel fluorescence-based assay for the rapid detection and quantification of cellular deoxyribonucleoside triphosphates," Nucleic Acids Res, 39(17):e112 (2011).

* cited by examiner

*Primary Examiner* — Carla J Myers

(74) *Attorney, Agent, or Firm* — Foley Hoag LLP

(57) ABSTRACT

Described herein are compositions and methods for diagnosing or monitoring type 1 diabetes.

17 Claims, 6 Drawing Sheets

Specification includes a Sequence Listing.

ial application Ser. No. 14/490,333, filed Sep. 18, 2014, which

SEQUENCE LISTING

```
<160> NUMBER OF SEQ ID NOS: 437

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
atttaagatt tgttgggagg tagag                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
atttaagatt cgtcgggagg tagag                                          25

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
gtggtttata tttggtgga                                                 19

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
attaactcac cctacaaatc                                                20

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
gtggtttata tttggtgga                                                 19

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
attaactcac cctacaaatc                                                20

<210> SEQ ID NO 7
<211> LENGTH: 16
<212> TYPE: DNA
<213> ORGANISM: Artificial Sequence
```

```
<220> FEATURE:
<223> OTHER INFORMATION: Synthetic primer

<400> SEQUENCE: 7
agagttttgt tttgta                                                       16

<210> SEQ ID NO 8
<211> LENGTH: 16
<212> TYPE: DNA
<213> ORGANISM: Artificial Sequence
<220> FEATURE:
<223> OTHER INFORMATION: Synthetic primer

<400> SEQUENCE: 8
agagtttcgt tttgta                                                       16

<210> SEQ ID NO 9
<211> LENGTH: 15
<212> TYPE: DNA
<213> ORGANISM: Artificial Sequence
<220> FEATURE:
<223> OTHER INFORMATION: Synthetic primer

<400> SEQUENCE: 9
gggatagtag tgtaa                                                        15

<210> SEQ ID NO 10
<211> LENGTH: 15
<212> TYPE: DNA
<213> ORGANISM: Artificial Sequence
<220> FEATURE:
<223> OTHER INFORMATION: Synthetic primer

<400> SEQUENCE: 10
cctactcaca actaa                                                        15

<210> SEQ ID NO 11
<211> LENGTH: 15
<212> TYPE: DNA
<213> ORGANISM: Artificial Sequence
<220> FEATURE:
<223> OTHER INFORMATION: Synthetic primer

<400> SEQUENCE: 11
tggttattgg gtttt                                                        15

<210> SEQ ID NO 12
<211> LENGTH: 15
<212> TYPE: DNA
<213> ORGANISM: Artificial Sequence
<220> FEATURE:
<223> OTHER INFORMATION: Synthetic primer

<400> SEQUENCE: 12
tggttatcgg gtttt                                                        15

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
ggaaagtggt ttaggtgagg gttt                                              24
```

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14
ctccttaatc atcaacacct cttcctc                                           27

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
tagttgtgag tagggatagg tt                                                22

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
aatctcctta atcatcaaca cct                                               23

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
ggtttaatgt ggaaagtggt ttag                                              24

<210> SEQ ID NO 18
<211> LENGTH: 28
<212> TYPE: DNA
<213> ORGANISM: Artificial Sequence
<220> FEATURE:
<223> OTHER INFORMATION: Synthetic primer

<400> SEQUENCE: 18
aaccatttcc ctaatactaa atctataa                                          28

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tttggtttaa tgtggaaagt                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ccaaaccatt tccctaatac                                                    20

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
gggatagtag tgtaaagagt t                                                  21

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
actacaattt ccaaaccatt tc                                                 22

<210> SEQ ID NO 23
<211> LENGTH: 21
<212> TYPE: DNA
<213> ORGANISM: Artificial Sequence
<220> FEATURE:
<223> OTHER INFORMATION: Synthetic primer

<400> SEQUENCE: 23
ttaatgattt gttggttttg a                                                  21

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
ttaatgattc gttggttttg a                                                  21

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

<400> SEQUENCE: 25
ggaaagtggt ttaggtgagg gttt                                               24

<210> SEQ ID NO 26
<211> LENGTH: 27
<212> TYPE: DNA
<213> ORGANISM: Artificial Sequence
<220> FEATURE:
<223> OTHER INFORMATION: Synthetic primer

<400> SEQUENCE: 26
atctccttaa tcatcaacac ctcttcc                                            27

<210> SEQ ID NO 27

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 27
gtgagtaggg ataggtttgg ttat                                              24

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
ccctaccacc taacccatta aa                                                22

<210> SEQ ID NO 29
<211> LENGTH: 23
<212> TYPE: DNA
<213> ORGANISM: Artificial Sequence
<220> FEATURE:
<223> OTHER INFORMATION: Synthetic primer

<400> SEQUENCE: 29
ggataggttt ggttattggg ttt                                               23

<210> SEQ ID NO 30
<211> LENGTH: 26
<212> TYPE: DNA
<213> ORGANISM: Artificial Sequence
<220> FEATURE:
<223> OTHER INFORMATION: Synthetic primer

<400> SEQUENCE: 30
tccaaaccat ttccctaata ctaaat                                            26

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
tagttgtgag tagggatagg t                                                 21

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
aaactacaat ttccaaacca tttc                                              24

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
```

```
tttaatgtgg aaagtggttt ag                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
aaatctcctt aatcatcaac ac                                              22

<210> SEQ ID NO 35
<211> LENGTH: 25
<212> TYPE: DNA
<213> ORGANISM: Artificial Sequence
<220> FEATURE:
<223> OTHER INFORMATION: Synthetic primer

<400> SEQUENCE: 35
aagaggtgtt gatgattaag gagat                                           25

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
aagaggtgtt gacgattaag gagat                                           25

<210> SEQ ID NO 37
<211> LENGTH: 24
<212> TYPE: DNA
<213> ORGANISM: Artificial Sequence
<220> FEATURE:
<223> OTHER INFORMATION: Synthetic primer

<400> SEQUENCE: 37
gtgagtaggg ataggtttgg ttat                                            24

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
ccctaccacc taacccatta aa                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic primer

<400> SEQUENCE: 39
gaaagtggtt taggtgaggg tt                                              22

<210> SEQ ID NO 40
<211> LENGTH: 28
<212> TYPE: DNA
```

```
<213> ORGANISM: Artificial Sequence
<220> FEATURE:
<223> OTHER INFORMATION: Synthetic primer

<400> SEQUENCE: 40
tccaaaccat ttccctaata ctaaatct                                          28

<210> SEQ ID NO 41
<211> LENGTH: 21
<212> TYPE: DNA
<213> ORGANISM: Artificial Sequence
<220> FEATURE:
<223> OTHER INFORMATION: Synthetic primer

<400> SEQUENCE: 41
tagttgtgag tagggatagg t                                                 21

<210> SEQ ID NO 42
<211> LENGTH: 24
<212> TYPE: DNA
<213> ORGANISM: Artificial Sequence
<220> FEATURE:
<223> OTHER INFORMATION: Synthetic primer

<400> SEQUENCE: 42
aaactacaat ttccaaacca tttc                                              24

<210> SEQ ID NO 43
<211> LENGTH: 22
<212> TYPE: DNA
<213> ORGANISM: Artificial Sequence
<220> FEATURE:
<223> OTHER INFORMATION: Synthetic primer

<400> SEQUENCE: 43
gataggtttg gttattgggt tt                                                22

<210> SEQ ID NO 44
<211> LENGTH: 23
<212> TYPE: DNA
<213> ORGANISM: Artificial Sequence
<220> FEATURE:
<223> OTHER INFORMATION: Synthetic primer

<400> SEQUENCE: 44
atttccaaac catttcccta ata                                               23

<210> SEQ ID NO 45
<211> LENGTH: 19
<212> TYPE: DNA
<213> ORGANISM: Artificial Sequence
<220> FEATURE:
<223> OTHER INFORMATION: Synthetic primer

<400> SEQUENCE: 45
tttaatgatt tgttggttt                                                    19

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
cccactaact ttataatctc                                                   20
```

```
<210> SEQ ID NO 47
<211> LENGTH: 19
<212> TYPE: DNA
<213> ORGANISM: Artificial Sequence
<220> FEATURE:
<223> OTHER INFORMATION: Synthetic primer

<400> SEQUENCE: 47
aaatggtttg gaaattgta                                              19

<210> SEQ ID NO 48
<211> LENGTH: 19
<212> TYPE: DNA
<213> ORGANISM: Artificial Sequence
<220> FEATURE:
<223> OTHER INFORMATION: Synthetic primer

<400> SEQUENCE: 48
aaatggttcg gaaattgta                                              19

<210> SEQ ID NO 49
<211> LENGTH: 22
<212> TYPE: DNA
<213> ORGANISM: Artificial Sequence
<220> FEATURE:
<223> OTHER INFORMATION: Synthetic primer

<400> SEQUENCE: 49
tgaggaagag gtgttgatga tt                                          22

<210> SEQ ID NO 50
<211> LENGTH: 22
<212> TYPE: DNA
<213> ORGANISM: Artificial Sequence
<220> FEATURE:
<223> OTHER INFORMATION: Synthetic primer

<400> SEQUENCE: 50
ccctaccacc taacccatta aa                                          22

<210> SEQ ID NO 51
<211> LENGTH: 25
<212> TYPE: DNA
<213> ORGANISM: Artificial Sequence
<220> FEATURE:
<223> OTHER INFORMATION: Synthetic primer

<400> SEQUENCE: 51
agaggtgttg atgattaagg agatt                                       25

<210> SEQ ID NO 52
<211> LENGTH: 27
<212> TYPE: DNA
<213> ORGANISM: Artificial Sequence
<220> FEATURE:
<223> OTHER INFORMATION: Synthetic primer

<400> SEQUENCE: 52
acctcttcta atacaaccta tcctaaa                                     27

<210> SEQ ID NO 53
<211> LENGTH: 19
<212> TYPE: DNA
<213> ORGANISM: Artificial Sequence
<220> FEATURE:
```

```
<223> OTHER INFORMATION: Synthetic primer

<400> SEQUENCE: 53
agttgtgagt agggatagg                                              19

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
cccactaact ttataatctc aaa                                         23

<210> SEQ ID NO 55
<211> LENGTH: 17
<212> TYPE: DNA
<213> ORGANISM: Artificial Sequence
<220> FEATURE:
<223> OTHER INFORMATION: Synthetic primer

<400> SEQUENCE: 55
tttgaggaag aggtgtt                                                17

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
acctcttcta atacaaccta                                             20

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
tttatagatt tagtattagg g                                           21

<210> SEQ ID NO 58
<211> LENGTH: 19
<212> TYPE: DNA
<213> ORGANISM: Artificial Sequence
<220> FEATURE:
<223> OTHER INFORMATION: Synthetic primer

<400> SEQUENCE: 58
ctacttaata acctcttct                                              19

<210> SEQ ID NO 59
<211> LENGTH: 13
<212> TYPE: DNA
<213> ORGANISM: Artificial Sequence
<220> FEATURE:
<223> OTHER INFORMATION: Synthetic primer

<400> SEQUENCE: 59
ttaggtggta ggg                                                    13
```

```
<210> SEQ ID NO 60
<211> LENGTH: 13
<212> TYPE: DNA
<213> ORGANISM: Artificial Sequence
<220> FEATURE:
<223> OTHER INFORMATION: Synthetic primer

<400> SEQUENCE: 60
ttaggtggta ggg                                                          13

<210> SEQ ID NO 61
<211> LENGTH: 28
<212> TYPE: DNA
<213> ORGANISM: Artificial Sequence
<220> FEATURE:
<223> OTHER INFORMATION: Synthetic primer

<400> SEQUENCE: 61
aataacctct tctaatacaa cctatcct                                          28

<210> SEQ ID NO 62
<211> LENGTH: 22
<212> TYPE: DNA
<213> ORGANISM: Artificial Sequence
<220> FEATURE:
<223> OTHER INFORMATION: Synthetic primer

<400> SEQUENCE: 62
agtattaggg aaatggtttg ga                                                22

<210> SEQ ID NO 63
<211> LENGTH: 27
<212> TYPE: DNA
<213> ORGANISM: Artificial Sequence
<220> FEATURE:
<223> OTHER INFORMATION: Synthetic primer

<400> SEQUENCE: 63
caaacctact taataacctc ttctaat                                           27

<210> SEQ ID NO 64
<211> LENGTH: 18
<212> TYPE: DNA
<213> ORGANISM: Artificial Sequence
<220> FEATURE:
<223> OTHER INFORMATION: Synthetic primer

<400> SEQUENCE: 64
gaggaagagg tgttgatg                                                     18

<210> SEQ ID NO 65
<211> LENGTH: 23
<212> TYPE: DNA
<213> ORGANISM: Artificial Sequence
<220> FEATURE:
<223> OTHER INFORMATION: Synthetic primer

<400> SEQUENCE: 65
cccactaact ttataatctc aaa                                               23

<210> SEQ ID NO 66
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 66
tttagtatta gggaaatg                                                 18

<210> SEQ ID NO 67
<211> LENGTH: 17
<212> TYPE: DNA
<213> ORGANISM: Artificial Sequence
<220> FEATURE:
<223> OTHER INFORMATION: Synthetic primer

<400> SEQUENCE: 67
acctacttaa taacctc                                                  17

<210> SEQ ID NO 68
<211> LENGTH: 16
<212> TYPE: DNA
<213> ORGANISM: Artificial Sequence
<220> FEATURE:
<223> OTHER INFORMATION: Synthetic primer

<400> SEQUENCE: 68
aagttagtgg gggttt                                                   16

<210> SEQ ID NO 69
<211> LENGTH: 16
<212> TYPE: DNA
<213> ORGANISM: Artificial Sequence
<220> FEATURE:
<223> OTHER INFORMATION: Synthetic primer

<400> SEQUENCE: 69
aagttagcgg gggttt                                                   16

<210> SEQ ID NO 70
<211> LENGTH: 22
<212> TYPE: DNA
<213> ORGANISM: Artificial Sequence
<220> FEATURE:
<223> OTHER INFORMATION: Synthetic primer

<400> SEQUENCE: 70
tttaatgggt taggtggtag gg                                            22

<210> SEQ ID NO 71
<211> LENGTH: 27
<212> TYPE: DNA
<213> ORGANISM: Artificial Sequence
<220> FEATURE:
<223> OTHER INFORMATION: Synthetic primer

<400> SEQUENCE: 71
acctcttcta atacaaccta tcctaaa                                       27

<210> SEQ ID NO 72
<211> LENGTH: 25
<212> TYPE: DNA
<213> ORGANISM: Artificial Sequence
<220> FEATURE:
<223> OTHER INFORMATION: Synthetic primer

<400> SEQUENCE: 72
gggaaatggt ttggaaattg tagtt                                         25

<210> SEQ ID NO 73
<211> LENGTH: 30
```

<212> TYPE: DNA
<213> ORGANISM: Artificial Sequence
<220> FEATURE:
<223> OTHER INFORMATION: Synthetic primer

<400> SEQUENCE: 73
acctacttaa taacctcttc taatacaacc                                    30

<210> SEQ ID NO 74
<211> LENGTH: 24
<212> TYPE: DNA
<213> ORGANISM: Artificial Sequence
<220> FEATURE:
<223> OTHER INFORMATION: Synthetic primer

<400> SEQUENCE: 74
gtattaggga aatggtttgg aaat                                          24

<210> SEQ ID NO 75
<211> LENGTH: 26
<212> TYPE: DNA
<213> ORGANISM: Artificial Sequence
<220> FEATURE:
<223> OTHER INFORMATION: Synthetic primer

<400> SEQUENCE: 75
acaaacctac ttaataacct cttcta                                        26

<210> SEQ ID NO 76
<211> LENGTH: 17
<212> TYPE: DNA
<213> ORGANISM: Artificial Sequence
<220> FEATURE:
<223> OTHER INFORMATION: Synthetic primer

<400> SEQUENCE: 76
agtattaggg aaatggt                                                  17

<210> SEQ ID NO 77
<211> LENGTH: 18
<212> TYPE: DNA
<213> ORGANISM: Artificial Sequence
<220> FEATURE:
<223> OTHER INFORMATION: Synthetic primer

<400> SEQUENCE: 77
caaacctact taataacc                                                 18

<210> SEQ ID NO 78
<211> LENGTH: 12
<212> TYPE: DNA
<213> ORGANISM: Artificial Sequence
<220> FEATURE:
<223> OTHER INFORMATION: Synthetic primer

<400> SEQUENCE: 78
tttgtgttag gt                                                       12

<210> SEQ ID NO 79
<211> LENGTH: 12
<212> TYPE: DNA
<213> ORGANISM: Artificial Sequence
<220> FEATURE:
<223> OTHER INFORMATION: Synthetic primer

<400> SEQUENCE: 79
tttgcgttag gt                                                                  12

<210> SEQ ID NO 80
<211> LENGTH: 30
<212> TYPE: DNA
<213> ORGANISM: Artificial Sequence
<220> FEATURE:
<223> OTHER INFORMATION: Synthetic primer

<400> SEQUENCE: 80
ggttgtatta gaagaggtta ttaagtaggt                                               30

<210> SEQ ID NO 81
<211> LENGTH: 22
<212> TYPE: DNA
<213> ORGANISM: Artificial Sequence
<220> FEATURE:
<223> OTHER INFORMATION: Synthetic primer

<400> SEQUENCE: 81
cttcacaaac ccaaccacat cc                                                       22

<210> SEQ ID NO 82
<211> LENGTH: 30
<212> TYPE: DNA
<213> ORGANISM: Artificial Sequence
<220> FEATURE:
<223> OTHER INFORMATION: Synthetic primer

<400> SEQUENCE: 82
ttaggatagg ttgtattaga agaggttatt                                               30

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
ccaaccacat cctccctact                                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
taatgggtta ggtggtaggg                                                          20

<210> SEQ ID NO 85
<211> LENGTH: 19
<212> TYPE: DNA
<213> ORGANISM: Artificial Sequence
<220> FEATURE:
<223> OTHER INFORMATION: Synthetic primer

<400> SEQUENCE: 85
cccacatact tcacaaacc                                                           19

<210> SEQ ID NO 86
<211> LENGTH: 21
<212> TYPE: DNA
<213> ORGANISM: Artificial Sequence -continued

```
<220> FEATURE:
<223> OTHER INFORMATION: Synthetic primer

<400> SEQUENCE: 86
aggataggtt gtattagaag a                                              21

<210> SEQ ID NO 87
<211> LENGTH: 18
<212> TYPE: DNA
<213> ORGANISM: Artificial Sequence
<220> FEATURE:
<223> OTHER INFORMATION: Synthetic primer

<400> SEQUENCE: 87
aaatccaacc accctaaa                                                  18

<210> SEQ ID NO 88
<211> LENGTH: 21
<212> TYPE: DNA
<213> ORGANISM: Artificial Sequence
<220> FEATURE:
<223> OTHER INFORMATION: Synthetic primer

<400> SEQUENCE: 88
ttgagattat aaagttagtg g                                              21

<210> SEQ ID NO 89
<211> LENGTH: 17
<212> TYPE: DNA
<213> ORGANISM: Artificial Sequence
<220> FEATURE:
<223> OTHER INFORMATION: Synthetic primer

<400> SEQUENCE: 89
aaaccaaata ccctacc                                                   17

<210> SEQ ID NO 90
<211> LENGTH: 20
<212> TYPE: DNA
<213> ORGANISM: Artificial Sequence
<220> FEATURE:
<223> OTHER INFORMATION: Synthetic primer

<400> SEQUENCE: 90
tagggaggat gtggttgggt                                                20

<210> SEQ ID NO 91
<211> LENGTH: 20
<212> TYPE: DNA
<213> ORGANISM: Artificial Sequence
<220> FEATURE:
<223> OTHER INFORMATION: Synthetic primer

<400> SEQUENCE: 91
tagggaggac gtggttgggt                                                20

<210> SEQ ID NO 92
<211> LENGTH: 19
<212> TYPE: DNA
<213> ORGANISM: Artificial Sequence
<220> FEATURE:
<223> OTHER INFORMATION: Synthetic primer

<400> SEQUENCE: 92
gtgttaggtg ggtttagga                                                 19
```

```
<210> SEQ ID NO 93
<211> LENGTH: 19
<212> TYPE: DNA
<213> ORGANISM: Artificial Sequence
<220> FEATURE:
<223> OTHER INFORMATION: Synthetic primer

<400> SEQUENCE: 93
aaaccaacaa caccaacaa                                                19

<210> SEQ ID NO 94
<211> LENGTH: 23
<212> TYPE: DNA
<213> ORGANISM: Artificial Sequence
<220> FEATURE:
<223> OTHER INFORMATION: Synthetic primer

<400> SEQUENCE: 94
aggataggtt gtattagaag agg                                           23

<210> SEQ ID NO 95
<211> LENGTH: 22
<212> TYPE: DNA
<213> ORGANISM: Artificial Sequence
<220> FEATURE:
<223> OTHER INFORMATION: Synthetic primer

<400> SEQUENCE: 95
aaaccaaata ccctacctta aa                                            22

<210> SEQ ID NO 96
<211> LENGTH: 17
<212> TYPE: DNA
<213> ORGANISM: Artificial Sequence
<220> FEATURE:
<223> OTHER INFORMATION: Synthetic primer

<400> SEQUENCE: 96
ttagggtggt tggattt                                                  17

<210> SEQ ID NO 97
<211> LENGTH: 22
<212> TYPE: DNA
<213> ORGANISM: Artificial Sequence
<220> FEATURE:
<223> OTHER INFORMATION: Synthetic primer

<400> SEQUENCE: 97
cacacaaata ttaattcaca aa                                            22

<210> SEQ ID NO 98
<211> LENGTH: 16
<212> TYPE: DNA
<213> ORGANISM: Artificial Sequence
<220> FEATURE:
<223> OTHER INFORMATION: Synthetic primer

<400> SEQUENCE: 98
ttgttggtgt tgttgg                                                   16

<210> SEQ ID NO 99
<211> LENGTH: 16
<212> TYPE: DNA
<213> ORGANISM: Artificial Sequence
<220> FEATURE:
<223> OTHER INFORMATION: Synthetic primer
```

<400> SEQUENCE: 99
ttgttggcgt tgttgg                                                                                      16

<210> SEQ ID NO 100
<211> LENGTH: 22
<212> TYPE: DNA
<213> ORGANISM: Artificial Sequence
<220> FEATURE:
<223> OTHER INFORMATION: Synthetic primer

<400> SEQUENCE: 100
gaggatgtgg ttgggtttgt ga                                                                               22

<210> SEQ ID NO 101
<211> LENGTH: 30
<212> TYPE: DNA
<213> ORGANISM: Artificial Sequence
<220> FEATURE:
<223> OTHER INFORMATION: Synthetic primer

<400> SEQUENCE: 101
aacttccacc aaatataaac cacacaaata                                                                       30

<210> SEQ ID NO 102
<211> LENGTH: 22
<212> TYPE: DNA
<213> ORGANISM: Artificial Sequence
<220> FEATURE:
<223> OTHER INFORMATION: Synthetic primer

<400> SEQUENCE: 102
ggttgggttt gtgaagtatg tg                                                                               22

<210> SEQ ID NO 103
<211> LENGTH: 30
<212> TYPE: DNA
<213> ORGANISM: Artificial Sequence
<220> FEATURE:
<223> OTHER INFORMATION: Synthetic primer

<400> SEQUENCE: 103
accaaatata aaccacacaa atattaattc                                                                       30

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
ttgtagtagg gaggatgtgg                                                                                  20

<210> SEQ ID NO 105
<211> LENGTH: 23
<212> TYPE: DNA
<213> ORGANISM: Artificial Sequence
<220> FEATURE:
<223> OTHER INFORMATION: Synthetic primer

<400> SEQUENCE: 105
aaacttccac caaatataaa cca                                                                              23

<210> SEQ ID NO 106

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 106
tttaaggtag ggtatttggt tt                                           22

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
cctctacctc ccaacaaatc                                              20

<210> SEQ ID NO 108
<211> LENGTH: 19
<212> TYPE: DNA
<213> ORGANISM: Artificial Sequence
<220> FEATURE:
<223> OTHER INFORMATION: Synthetic primer

<400> SEQUENCE: 108
gtgttaggtg ggtttagga                                               19

<210> SEQ ID NO 109
<211> LENGTH: 23
<212> TYPE: DNA
<213> ORGANISM: Artificial Sequence
<220> FEATURE:
<223> OTHER INFORMATION: Synthetic primer

<400> SEQUENCE: 109
aaactacaac taaatcaaat ccc                                          23

<210> SEQ ID NO 110
<211> LENGTH: 22
<212> TYPE: DNA
<213> ORGANISM: Artificial Sequence
<220> FEATURE:
<223> OTHER INFORMATION: Synthetic primer

<400> SEQUENCE: 110
tttaaggtag ggtatttggt tt                                           22

<210> SEQ ID NO 111
<211> LENGTH: 24
<212> TYPE: DNA
<213> ORGANISM: Artificial Sequence
<220> FEATURE:
<223> OTHER INFORMATION: Synthetic primer

<400> SEQUENCE: 111
accacacaaa tattaattca caaa                                         24

<210> SEQ ID NO 112
<211> LENGTH: 20
<212> TYPE: DNA
<213> ORGANISM: Artificial Sequence
<220> FEATURE:
<223> OTHER INFORMATION: Synthetic primer

<400> SEQUENCE: 112
```

```
ttgtagtagg gaggatgtgg                                           20

<210> SEQ ID NO 113
<211> LENGTH: 23
<212> TYPE: DNA
<213> ORGANISM: Artificial Sequence
<220> FEATURE:
<223> OTHER INFORMATION: Synthetic primer

<400> SEQUENCE: 113
aaactacaac taaatcaaat ccc                                       23

<210> SEQ ID NO 114
<211> LENGTH: 12
<212> TYPE: DNA
<213> ORGANISM: Artificial Sequence
<220> FEATURE:
<223> OTHER INFORMATION: Synthetic primer

<400> SEQUENCE: 114
ttagttgtag tt                                                   12

<210> SEQ ID NO 115
<211> LENGTH: 12
<212> TYPE: DNA
<213> ORGANISM: Artificial Sequence
<220> FEATURE:
<223> OTHER INFORMATION: Synthetic primer

<400> SEQUENCE: 115
ttagtcgtag tt                                                   12

<210> SEQ ID NO 116
<211> LENGTH: 22
<212> TYPE: DNA
<213> ORGANISM: Artificial Sequence
<220> FEATURE:
<223> OTHER INFORMATION: Synthetic primer

<400> SEQUENCE: 116
ggttgggttt gtgaagtatg tg                                        22

<210> SEQ ID NO 117
<211> LENGTH: 30
<212> TYPE: DNA
<213> ORGANISM: Artificial Sequence
<220> FEATURE:
<223> OTHER INFORMATION: Synthetic primer

<400> SEQUENCE: 117
accaaatata aaccacacaa atattaattc                                30

<210> SEQ ID NO 118
<211> LENGTH: 20
<212> TYPE: DNA
<213> ORGANISM: Artificial Sequence
<220> FEATURE:
<223> OTHER INFORMATION: Synthetic primer

<400> SEQUENCE: 118
ttgtagtagg gaggatgtgg                                           20

<210> SEQ ID NO 119
<211> LENGTH: 23
<212> TYPE: DNA
```

```
<213> ORGANISM: Artificial Sequence
<220> FEATURE:
<223> OTHER INFORMATION: Synthetic primer

<400> SEQUENCE: 119
aaacttccac caaatataaa cca                                               23

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
tttgttggtg ttgttggttt                                                   20

<210> SEQ ID NO 121
<211> LENGTH: 20
<212> TYPE: DNA
<213> ORGANISM: Artificial Sequence
<220> FEATURE:
<223> OTHER INFORMATION: Synthetic primer

<400> SEQUENCE: 121
cctctacctc ccaacaaatc                                                   20

<210> SEQ ID NO 122
<211> LENGTH: 22
<212> TYPE: DNA
<213> ORGANISM: Artificial Sequence
<220> FEATURE:
<223> OTHER INFORMATION: Synthetic primer

<400> SEQUENCE: 122
tttaaggtag ggtatttggt tt                                                22

<210> SEQ ID NO 123
<211> LENGTH: 24
<212> TYPE: DNA
<213> ORGANISM: Artificial Sequence
<220> FEATURE:
<223> OTHER INFORMATION: Synthetic primer

<400> SEQUENCE: 123
accacacaaa tattaattca caaa                                              24

<210> SEQ ID NO 124
<211> LENGTH: 12
<212> TYPE: DNA
<213> ORGANISM: Artificial Sequence
<220> FEATURE:
<223> OTHER INFORMATION: Synthetic primer

<400> SEQUENCE: 124
ttgtgtggtt ta                                                           12

<210> SEQ ID NO 125
<211> LENGTH: 12
<212> TYPE: DNA
<213> ORGANISM: Artificial Sequence
<220> FEATURE:
<223> OTHER INFORMATION: Synthetic primer

<400> SEQUENCE: 125
ttgtgcggtt ta                                                           12
```

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
tttgttggtg ttgttggttt                                        20

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
cctctacctc ccaacaaatc                                        20

<210> SEQ ID NO 128
<211> LENGTH: 23
<212> TYPE: DNA
<213> ORGANISM: Artificial Sequence
<220> FEATURE:
<223> OTHER INFORMATION: Synthetic primer

<400> SEQUENCE: 128
gggatttgat ttagttgtag ttt                                    23

<210> SEQ ID NO 129
<211> LENGTH: 21
<212> TYPE: DNA
<213> ORGANISM: Artificial Sequence
<220> FEATURE:
<223> OTHER INFORMATION: Synthetic primer

<400> SEQUENCE: 129
ctcaccctac aaatcctcta c                                      21

<210> SEQ ID NO 130
<211> LENGTH: 21
<212> TYPE: DNA
<213> ORGANISM: Artificial Sequence
<220> FEATURE:
<223> OTHER INFORMATION: Synthetic primer

<400> SEQUENCE: 130
tttaaggtag ggtatttggt t                                      21

<210> SEQ ID NO 131
<211> LENGTH: 22
<212> TYPE: DNA
<213> ORGANISM: Artificial Sequence
<220> FEATURE:
<223> OTHER INFORMATION: Synthetic primer

<400> SEQUENCE: 131
acctcccaac aaatcttaaa ta                                     22

<210> SEQ ID NO 132
<211> LENGTH: 17
<212> TYPE: DNA
<213> ORGANISM: Artificial Sequence
<220> FEATURE:

<223> OTHER INFORMATION: Synthetic primer

<400> SEQUENCE: 132
gttgggtttg tgaagta                                                    17

<210> SEQ ID NO 133
<211> LENGTH: 17
<212> TYPE: DNA
<213> ORGANISM: Artificial Sequence
<220> FEATURE:
<223> OTHER INFORMATION: Synthetic primer

<400> SEQUENCE: 133
cccacacact aaataaa                                                    17

<210> SEQ ID NO 134
<211> LENGTH: 13
<212> TYPE: DNA
<213> ORGANISM: Artificial Sequence
<220> FEATURE:
<223> OTHER INFORMATION: Synthetic primer

<400> SEQUENCE: 134
agtgtgtggg gaa                                                        13

<210> SEQ ID NO 135
<211> LENGTH: 13
<212> TYPE: DNA
<213> ORGANISM: Artificial Sequence
<220> FEATURE:
<223> OTHER INFORMATION: Synthetic primer

<400> SEQUENCE: 135
agtgtgcggg gaa                                                        13

<210> SEQ ID NO 136
<211> LENGTH: 28
<212> TYPE: DNA
<213> ORGANISM: Artificial Sequence
<220> FEATURE:
<223> OTHER INFORMATION: Synthetic primer

<400> SEQUENCE: 136
atttgtgtgg tttatatttg gtggaagt                                        28

<210> SEQ ID NO 137
<211> LENGTH: 24
<212> TYPE: DNA
<213> ORGANISM: Artificial Sequence
<220> FEATURE:
<223> OTHER INFORMATION: Synthetic primer

<400> SEQUENCE: 137
actcacccta caaatcctct acct                                            24

<210> SEQ ID NO 138
<211> LENGTH: 30
<212> TYPE: DNA
<213> ORGANISM: Artificial Sequence
<220> FEATURE:
<223> OTHER INFORMATION: Synthetic primer

<400> SEQUENCE: 138
ttgtgaatta atatttgtgt ggtttatatt                                      30

```
<210> SEQ ID NO 139
<211> LENGTH: 21
<212> TYPE: DNA
<213> ORGANISM: Artificial Sequence
<220> FEATURE:
<223> OTHER INFORMATION: Synthetic primer

<400> SEQUENCE: 139
tcctctacct cccaacaaat c                                              21

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
tttgttggtg ttgttggttt                                                20

<210> SEQ ID NO 141
<211> LENGTH: 25
<212> TYPE: DNA
<213> ORGANISM: Artificial Sequence
<220> FEATURE:
<223> OTHER INFORMATION: Synthetic primer

<400> SEQUENCE: 141
tctacctccc aacaaatctt aaata                                          25

<210> SEQ ID NO 142
<211> LENGTH: 24
<212> TYPE: DNA
<213> ORGANISM: Artificial Sequence
<220> FEATURE:
<223> OTHER INFORMATION: Synthetic primer

<400> SEQUENCE: 142
tttgtgaatt aatatttgtg tggt                                           24

<210> SEQ ID NO 143
<211> LENGTH: 24
<212> TYPE: DNA
<213> ORGANISM: Artificial Sequence
<220> FEATURE:
<223> OTHER INFORMATION: Synthetic primer

<400> SEQUENCE: 143
caataaacaa ttaactcacc ctac                                           24

<210> SEQ ID NO 144
<211> LENGTH: 23
<212> TYPE: DNA
<213> ORGANISM: Artificial Sequence
<220> FEATURE:
<223> OTHER INFORMATION: Synthetic primer

<400> SEQUENCE: 144
gggatttgat ttagttgtag ttt                                            23

<210> SEQ ID NO 145
<211> LENGTH: 21
<212> TYPE: DNA
<213> ORGANISM: Artificial Sequence
<220> FEATURE:
<223> OTHER INFORMATION: Synthetic primer
```

-continued

<400> SEQUENCE: 145
ctaaataaca acctcctacc c    21

<210> SEQ ID NO 146
<211> LENGTH: 14
<212> TYPE: DNA
<213> ORGANISM: Artificial Sequence
<220> FEATURE:
<223> OTHER INFORMATION: Synthetic primer

<400> SEQUENCE: 146
agatttgttg ggag    14

<210> SEQ ID NO 147
<211> LENGTH: 14
<212> TYPE: DNA
<213> ORGANISM: Artificial Sequence
<220> FEATURE:
<223> OTHER INFORMATION: Synthetic primer

<400> SEQUENCE: 147
agattcgtcg ggag    14

<210> SEQ ID NO 148
<211> LENGTH: 28
<212> TYPE: DNA
<213> ORGANISM: Artificial Sequence
<220> FEATURE:
<223> OTHER INFORMATION: Synthetic primer

<400> SEQUENCE: 148
atttgtgtgg tttatatttg gtggaagt    28

<210> SEQ ID NO 149
<211> LENGTH: 29
<212> TYPE: DNA
<213> ORGANISM: Artificial Sequence
<220> FEATURE:
<223> OTHER INFORMATION: Synthetic primer

<400> SEQUENCE: 149
acaattaact caccctacaa atcctctac    29

<210> SEQ ID NO 150
<211> LENGTH: 30
<212> TYPE: DNA
<213> ORGANISM: Artificial Sequence
<220> FEATURE:
<223> OTHER INFORMATION: Synthetic primer

<400> SEQUENCE: 150
tgaattaata tttgtgtggt ttatatttgg    30

<210> SEQ ID NO 151
<211> LENGTH: 26
<212> TYPE: DNA
<213> ORGANISM: Artificial Sequence
<220> FEATURE:
<223> OTHER INFORMATION: Synthetic primer

<400> SEQUENCE: 151
acaataaaca attaactcac cctaca    26

<210> SEQ ID NO 152
<211> LENGTH: 27

```
<212> TYPE: DNA
<213> ORGANISM: Artificial Sequence
<220> FEATURE:
<223> OTHER INFORMATION: Synthetic primer

<400> SEQUENCE: 152
tttgtgaatt aatatttgtg tggttta                                       27

<210> SEQ ID NO 153
<211> LENGTH: 24
<212> TYPE: DNA
<213> ORGANISM: Artificial Sequence
<220> FEATURE:
<223> OTHER INFORMATION: Synthetic primer

<400> SEQUENCE: 153
cctactaaat aacaacctcc tacc                                          24

<210> SEQ ID NO 154
<211> LENGTH: 18
<212> TYPE: DNA
<213> ORGANISM: Artificial Sequence
<220> FEATURE:
<223> OTHER INFORMATION: Synthetic primer

<400> SEQUENCE: 154
tgttggtgtt gttggttt                                                 18

<210> SEQ ID NO 155
<211> LENGTH: 23
<212> TYPE: DNA
<213> ORGANISM: Artificial Sequence
<220> FEATURE:
<223> OTHER INFORMATION: Synthetic primer

<400> SEQUENCE: 155
cccttctacc catactaaat aaa                                           23

<210> SEQ ID NO 156
<211> LENGTH: 20
<212> TYPE: DNA
<213> ORGANISM: Artificial Sequence
<220> FEATURE:
<223> OTHER INFORMATION: Synthetic primer

<400> SEQUENCE: 156
tttgtgaatt aatatttgtg                                               20

<210> SEQ ID NO 157
<211> LENGTH: 18
<212> TYPE: DNA
<213> ORGANISM: Artificial Sequence
<220> FEATURE:
<223> OTHER INFORMATION: Synthetic primer

<400> SEQUENCE: 157
ccctactaaa taacaacc                                                 18

<210> SEQ ID NO 158
<211> LENGTH: 12
<212> TYPE: DNA
<213> ORGANISM: Artificial Sequence
<220> FEATURE:
<223> OTHER INFORMATION: Synthetic primer

<400> SEQUENCE: 158
```

```
ttggttgttt tt                                                     12

<210> SEQ ID NO 159
<211> LENGTH: 12
<212> TYPE: DNA
<213> ORGANISM: Artificial Sequence
<220> FEATURE:
<223> OTHER INFORMATION: Synthetic primer

<400> SEQUENCE: 159
ttggtcgttt tt                                                     12

<210> SEQ ID NO 160
<211> LENGTH: 27
<212> TYPE: DNA
<213> ORGANISM: Artificial Sequence
<220> FEATURE:
<223> OTHER INFORMATION: Synthetic primer

<400> SEQUENCE: 160
ggtagaggat ttgtagggtg agttaat                                     27

<210> SEQ ID NO 161
<211> LENGTH: 26
<212> TYPE: DNA
<213> ORGANISM: Artificial Sequence
<220> FEATURE:
<223> OTHER INFORMATION: Synthetic primer

<400> SEQUENCE: 161
ccctactaaa taacaacctc ctaccc                                      26

<210> SEQ ID NO 162
<211> LENGTH: 24
<212> TYPE: DNA
<213> ORGANISM: Artificial Sequence
<220> FEATURE:
<223> OTHER INFORMATION: Synthetic primer

<400> SEQUENCE: 162
ttgttgggag gtagaggatt tgta                                        24

<210> SEQ ID NO 163
<211> LENGTH: 25
<212> TYPE: DNA
<213> ORGANISM: Artificial Sequence
<220> FEATURE:
<223> OTHER INFORMATION: Synthetic primer

<400> SEQUENCE: 163
aaaccaacac catcctcaaa ctaaa                                       25

<210> SEQ ID NO 164
<211> LENGTH: 28
<212> TYPE: DNA
<213> ORGANISM: Artificial Sequence
<220> FEATURE:
<223> OTHER INFORMATION: Synthetic primer

<400> SEQUENCE: 164
agggtgagtt aattgtttat tgttgttt                                    28

<210> SEQ ID NO 165
<211> LENGTH: 27
<212> TYPE: DNA
<213> ORGANISM: Artificial Sequence
```

```
<220> FEATURE:
<223> OTHER INFORMATION: Synthetic primer

<400> SEQUENCE: 165
acatacccac cctctaatat atctcaa                                              27

<210> SEQ ID NO 166
<211> LENGTH: 22
<212> TYPE: DNA
<213> ORGANISM: Artificial Sequence
<220> FEATURE:
<223> OTHER INFORMATION: Synthetic primer

<400> SEQUENCE: 166
taagatttgt tgggaggtag ag                                                   22

<210> SEQ ID NO 167
<211> LENGTH: 23
<212> TYPE: DNA
<213> ORGANISM: Artificial Sequence
<220> FEATURE:
<223> OTHER INFORMATION: Synthetic primer

<400> SEQUENCE: 167
cccttctacc catactaaat aaa                                                  23

<210> SEQ ID NO 168
<211> LENGTH: 23
<212> TYPE: DNA
<213> ORGANISM: Artificial Sequence
<220> FEATURE:
<223> OTHER INFORMATION: Synthetic primer

<400> SEQUENCE: 168
gtagggtgag ttaattgttt att                                                  23

<210> SEQ ID NO 169
<211> LENGTH: 17
<212> TYPE: DNA
<213> ORGANISM: Artificial Sequence
<220> FEATURE:
<223> OTHER INFORMATION: Synthetic primer

<400> SEQUENCE: 169
aaccaacacc atcctca                                                         17

<210> SEQ ID NO 170
<211> LENGTH: 12
<212> TYPE: DNA
<213> ORGANISM: Artificial Sequence
<220> FEATURE:
<223> OTHER INFORMATION: Synthetic primer

<400> SEQUENCE: 170
tttggtgttt tt                                                              12

<210> SEQ ID NO 171
<211> LENGTH: 12
<212> TYPE: DNA
<213> ORGANISM: Artificial Sequence
<220> FEATURE:
<223> OTHER INFORMATION: Synthetic primer

<400> SEQUENCE: 171
tttggcgttt tt                                                              12
```

<210> SEQ ID NO 172
<211> LENGTH: 27
<212> TYPE: DNA
<213> ORGANISM: Artificial Sequence
<220> FEATURE:
<223> OTHER INFORMATION: Synthetic primer

<400> SEQUENCE: 172
ggtagaggat ttgtagggtg agttaat                                27

<210> SEQ ID NO 173
<211> LENGTH: 26
<212> TYPE: DNA
<213> ORGANISM: Artificial Sequence
<220> FEATURE:
<223> OTHER INFORMATION: Synthetic primer

<400> SEQUENCE: 173
ccctactaaa taacaacctc ctaccc                                 26

<210> SEQ ID NO 174
<211> LENGTH: 24
<212> TYPE: DNA
<213> ORGANISM: Artificial Sequence
<220> FEATURE:
<223> OTHER INFORMATION: Synthetic primer

<400> SEQUENCE: 174
ttgttgggag gtagaggatt tgta                                   24

<210> SEQ ID NO 175
<211> LENGTH: 25
<212> TYPE: DNA
<213> ORGANISM: Artificial Sequence
<220> FEATURE:
<223> OTHER INFORMATION: Synthetic primer

<400> SEQUENCE: 175
aaaccaacac catcctcaaa ctaaa                                  25

<210> SEQ ID NO 176
<211> LENGTH: 28
<212> TYPE: DNA
<213> ORGANISM: Artificial Sequence
<220> FEATURE:
<223> OTHER INFORMATION: Synthetic primer

<400> SEQUENCE: 176
agggtgagtt aattgtttat tgttgttt                               28

<210> SEQ ID NO 177
<211> LENGTH: 27
<212> TYPE: DNA
<213> ORGANISM: Artificial Sequence
<220> FEATURE:
<223> OTHER INFORMATION: Synthetic primer

<400> SEQUENCE: 177
acatacccac cctctaatat atctcaa                                27

<210> SEQ ID NO 178
<211> LENGTH: 25
<212> TYPE: DNA
<213> ORGANISM: Artificial Sequence
<220> FEATURE:
<223> OTHER INFORMATION: Synthetic primer -continued

<400> SEQUENCE: 178
atttaagatt tgttgggagg tagag                                    25

<210> SEQ ID NO 179
<211> LENGTH: 25
<212> TYPE: DNA
<213> ORGANISM: Artificial Sequence
<220> FEATURE:
<223> OTHER INFORMATION: Synthetic primer

<400> SEQUENCE: 179
atttaagatt cgtcgggagg tagag                                    25

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
agatttgttg ggaggtagag                                          20

<210> SEQ ID NO 181
<211> LENGTH: 18
<212> TYPE: DNA
<213> ORGANISM: Artificial Sequence
<220> FEATURE:
<223> OTHER INFORMATION: Synthetic primer

<400> SEQUENCE: 181
aaaccaacac catcctca                                            18

<210> SEQ ID NO 182
<211> LENGTH: 22
<212> TYPE: DNA
<213> ORGANISM: Artificial Sequence
<220> FEATURE:
<223> OTHER INFORMATION: Synthetic primer

<400> SEQUENCE: 182
gtagggtgag ttaattgttt at                                       22

<210> SEQ ID NO 183
<211> LENGTH: 20
<212> TYPE: DNA
<213> ORGANISM: Artificial Sequence
<220> FEATURE:
<223> OTHER INFORMATION: Synthetic primer

<400> SEQUENCE: 183
cccttctacc catactaaat                                          20

<210> SEQ ID NO 184
<211> LENGTH: 14
<212> TYPE: DNA
<213> ORGANISM: Artificial Sequence
<220> FEATURE:
<223> OTHER INFORMATION: Synthetic primer

<400> SEQUENCE: 184
tggttatgtt ttaa                                                14

<210> SEQ ID NO 185

```
<211> LENGTH: 14
<212> TYPE: DNA
<213> ORGANISM: Artificial Sequence
<220> FEATURE:
<223> OTHER INFORMATION: Synthetic primer

<400> SEQUENCE: 185
tggttacgtt ttaa                                                         14

<210> SEQ ID NO 186
<211> LENGTH: 26
<212> TYPE: DNA
<213> ORGANISM: Artificial Sequence
<220> FEATURE:
<223> OTHER INFORMATION: Synthetic primer

<400> SEQUENCE: 186
gggtaggagg ttgttattta gtaggg                                            26

<210> SEQ ID NO 187
<211> LENGTH: 22
<212> TYPE: DNA
<213> ORGANISM: Artificial Sequence
<220> FEATURE:
<223> OTHER INFORMATION: Synthetic primer

<400> SEQUENCE: 187
aaaccaacac catcctcaaa ct                                                22

<210> SEQ ID NO 188
<211> LENGTH: 28
<212> TYPE: DNA
<213> ORGANISM: Artificial Sequence
<220> FEATURE:
<223> OTHER INFORMATION: Synthetic primer

<400> SEQUENCE: 188
agggtgagtt aattgtttat tgttgttt                                          28

<210> SEQ ID NO 189
<211> LENGTH: 27
<212> TYPE: DNA
<213> ORGANISM: Artificial Sequence
<220> FEATURE:
<223> OTHER INFORMATION: Synthetic primer

<400> SEQUENCE: 189
acatacccac cctctaatat atctcaa                                           27

<210> SEQ ID NO 190
<211> LENGTH: 19
<212> TYPE: DNA
<213> ORGANISM: Artificial Sequence
<220> FEATURE:
<223> OTHER INFORMATION: Synthetic primer

<400> SEQUENCE: 190
gggtaggagg ttgttattt                                                    19

<210> SEQ ID NO 191
<211> LENGTH: 19
<212> TYPE: DNA
<213> ORGANISM: Artificial Sequence
<220> FEATURE:
<223> OTHER INFORMATION: Synthetic primer

<400> SEQUENCE: 191
```
acatacccac cctctaata                                                  19

<210> SEQ ID NO 192
<211> LENGTH: 18
<212> TYPE: DNA
<213> ORGANISM: Artificial Sequence
<220> FEATURE:
<223> OTHER INFORMATION: Synthetic primer

<400> SEQUENCE: 192
ttagtatggg tagaaggg                                                   18

<210> SEQ ID NO 193
<211> LENGTH: 21
<212> TYPE: DNA
<213> ORGANISM: Artificial Sequence
<220> FEATURE:
<223> OTHER INFORMATION: Synthetic primer

<400> SEQUENCE: 193
aaattctaac taaaccacaa a                                               21

<210> SEQ ID NO 194
<211> LENGTH: 14
<212> TYPE: DNA
<213> ORGANISM: Artificial Sequence
<220> FEATURE:
<223> OTHER INFORMATION: Synthetic primer

<400> SEQUENCE: 194
tgaggatggt gttg                                                       14

<210> SEQ ID NO 195
<211> LENGTH: 14
<212> TYPE: DNA
<213> ORGANISM: Artificial Sequence
<220> FEATURE:
<223> OTHER INFORMATION: Synthetic primer

<400> SEQUENCE: 195
tgaggacggt gttg                                                       14

<210> SEQ ID NO 196
<211> LENGTH: 28
<212> TYPE: DNA
<213> ORGANISM: Artificial Sequence
<220> FEATURE:
<223> OTHER INFORMATION: Synthetic primer

<400> SEQUENCE: 196
agggtgagtt aattgtttat tgttgttt                                        28

<210> SEQ ID NO 197
<211> LENGTH: 27
<212> TYPE: DNA
<213> ORGANISM: Artificial Sequence
<220> FEATURE:
<223> OTHER INFORMATION: Synthetic primer

<400> SEQUENCE: 197
acatacccac cctctaatat atctcaa                                         27

<210> SEQ ID NO 198
<211> LENGTH: 22
<212> TYPE: DNA

<213> ORGANISM: Artificial Sequence
<220> FEATURE:
<223> OTHER INFORMATION: Synthetic primer

<400> SEQUENCE: 198
gggtaggagg ttgttattta gt                                                22

<210> SEQ ID NO 199
<211> LENGTH: 21
<212> TYPE: DNA
<213> ORGANISM: Artificial Sequence
<220> FEATURE:
<223> OTHER INFORMATION: Synthetic primer

<400> SEQUENCE: 199
aaacataccc accctctaat a                                                 21

<210> SEQ ID NO 200
<211> LENGTH: 21
<212> TYPE: DNA
<213> ORGANISM: Artificial Sequence
<220> FEATURE:
<223> OTHER INFORMATION: Synthetic primer

<400> SEQUENCE: 200
tttgtggttt agttagaatt t                                                 21

<210> SEQ ID NO 201
<211> LENGTH: 17
<212> TYPE: DNA
<213> ORGANISM: Artificial Sequence
<220> FEATURE:
<223> OTHER INFORMATION: Synthetic primer

<400> SEQUENCE: 201
ccctcctcca aacataa                                                      17

<210> SEQ ID NO 202
<211> LENGTH: 28
<212> TYPE: DNA
<213> ORGANISM: Artificial Sequence
<220> FEATURE:
<223> OTHER INFORMATION: Synthetic primer

<400> SEQUENCE: 202
agggtgagtt aattgtttat tgttgttt                                          28

<210> SEQ ID NO 203
<211> LENGTH: 27
<212> TYPE: DNA
<213> ORGANISM: Artificial Sequence
<220> FEATURE:
<223> OTHER INFORMATION: Synthetic primer

<400> SEQUENCE: 203
acatacccac cctctaatat atctcaa                                           27

<210> SEQ ID NO 204
<211> LENGTH: 22
<212> TYPE: DNA
<213> ORGANISM: Artificial Sequence
<220> FEATURE:
<223> OTHER INFORMATION: Synthetic primer

<400> SEQUENCE: 204
gggtaggagg ttgttattta gt                                                22

```
<210> SEQ ID NO 205
<211> LENGTH: 21
<212> TYPE: DNA
<213> ORGANISM: Artificial Sequence
<220> FEATURE:
<223> OTHER INFORMATION: Synthetic primer

<400> SEQUENCE: 205
aaacataccc accctctaat a                                              21

<210> SEQ ID NO 206
<211> LENGTH: 18
<212> TYPE: DNA
<213> ORGANISM: Artificial Sequence
<220> FEATURE:
<223> OTHER INFORMATION: Synthetic primer

<400> SEQUENCE: 206
ttagtttgag gatggtgt                                                  18

<210> SEQ ID NO 207
<211> LENGTH: 20
<212> TYPE: DNA
<213> ORGANISM: Artificial Sequence
<220> FEATURE:
<223> OTHER INFORMATION: Synthetic primer

<400> SEQUENCE: 207
cctcctccaa acataataaa                                                20

<210> SEQ ID NO 208
<211> LENGTH: 21
<212> TYPE: DNA
<213> ORGANISM: Artificial Sequence
<220> FEATURE:
<223> OTHER INFORMATION: Synthetic primer

<400> SEQUENCE: 208
tttgtggttt agttagaatt t                                              21

<210> SEQ ID NO 209
<211> LENGTH: 22
<212> TYPE: DNA
<213> ORGANISM: Artificial Sequence
<220> FEATURE:
<223> OTHER INFORMATION: Synthetic primer

<400> SEQUENCE: 209
aaacacttaa atctacaatc at                                             22

<210> SEQ ID NO 210
<211> LENGTH: 12
<212> TYPE: DNA
<213> ORGANISM: Artificial Sequence
<220> FEATURE:
<223> OTHER INFORMATION: Synthetic primer

<400> SEQUENCE: 210
agttttgaga ta                                                        12

<210> SEQ ID NO 211
<211> LENGTH: 12
<212> TYPE: DNA
<213> ORGANISM: Artificial Sequence
<220> FEATURE:
```

<223> OTHER INFORMATION: Synthetic primer

<400> SEQUENCE: 211
agtttcgaga ta                                                          12

<210> SEQ ID NO 212
<211> LENGTH: 19
<212> TYPE: DNA
<213> ORGANISM: Artificial Sequence
<220> FEATURE:
<223> OTHER INFORMATION: Synthetic primer

<400> SEQUENCE: 212
ttgaggatgg tgttggttt                                                   19

<210> SEQ ID NO 213
<211> LENGTH: 22
<212> TYPE: DNA
<213> ORGANISM: Artificial Sequence
<220> FEATURE:
<223> OTHER INFORMATION: Synthetic primer

<400> SEQUENCE: 213
caccctcctc caaacataat aa                                               22

<210> SEQ ID NO 214
<211> LENGTH: 22
<212> TYPE: DNA
<213> ORGANISM: Artificial Sequence
<220> FEATURE:
<223> OTHER INFORMATION: Synthetic primer

<400> SEQUENCE: 214
gggtaggagg ttgttattta gt                                               22

<210> SEQ ID NO 215
<211> LENGTH: 21
<212> TYPE: DNA
<213> ORGANISM: Artificial Sequence
<220> FEATURE:
<223> OTHER INFORMATION: Synthetic primer

<400> SEQUENCE: 215
aaacataccc accctctaat a                                                21

<210> SEQ ID NO 216
<211> LENGTH: 18
<212> TYPE: DNA
<213> ORGANISM: Artificial Sequence
<220> FEATURE:
<223> OTHER INFORMATION: Synthetic primer

<400> SEQUENCE: 216
tttagtttga ggatggtg                                                    18

<210> SEQ ID NO 217
<211> LENGTH: 22
<212> TYPE: DNA
<213> ORGANISM: Artificial Sequence
<220> FEATURE:
<223> OTHER INFORMATION: Synthetic primer

<400> SEQUENCE: 217
aaacacttaa atctacaatc at                                               22

```
<210> SEQ ID NO 218
<211> LENGTH: 19
<212> TYPE: DNA
<213> ORGANISM: Artificial Sequence
<220> FEATURE:
<223> OTHER INFORMATION: Synthetic primer

<400> SEQUENCE: 218
tgtggtttag ttagaattt                                                19

<210> SEQ ID NO 219
<211> LENGTH: 20
<212> TYPE: DNA
<213> ORGANISM: Artificial Sequence
<220> FEATURE:
<223> OTHER INFORMATION: Synthetic primer

<400> SEQUENCE: 219
aatctacaat catcaaataa                                               20

<210> SEQ ID NO 220
<211> LENGTH: 13
<212> TYPE: DNA
<213> ORGANISM: Artificial Sequence
<220> FEATURE:
<223> OTHER INFORMATION: Synthetic primer

<400> SEQUENCE: 220
tgggtatgtt ttt                                                      13

<210> SEQ ID NO 221
<211> LENGTH: 13
<212> TYPE: DNA
<213> ORGANISM: Artificial Sequence
<220> FEATURE:
<223> OTHER INFORMATION: Synthetic primer

<400> SEQUENCE: 221
tgggtacgtt ttt                                                      13

<210> SEQ ID NO 222
<211> LENGTH: 19
<212> TYPE: DNA
<213> ORGANISM: Artificial Sequence
<220> FEATURE:
<223> OTHER INFORMATION: Synthetic primer

<400> SEQUENCE: 222
ttgaggatgg tgttggttt                                                19

<210> SEQ ID NO 223
<211> LENGTH: 22
<212> TYPE: DNA
<213> ORGANISM: Artificial Sequence
<220> FEATURE:
<223> OTHER INFORMATION: Synthetic primer

<400> SEQUENCE: 223
caccctcctc caaacataat aa                                            22

<210> SEQ ID NO 224
<211> LENGTH: 25
<212> TYPE: DNA
<213> ORGANISM: Artificial Sequence
<220> FEATURE:
<223> OTHER INFORMATION: Synthetic primer
```

<400> SEQUENCE: 224
gggtaggagg ttgttattta gtagg                                    25

<210> SEQ ID NO 225
<211> LENGTH: 30
<212> TYPE: DNA
<213> ORGANISM: Artificial Sequence
<220> FEATURE:
<223> OTHER INFORMATION: Synthetic primer

<400> SEQUENCE: 225
aaacacttaa atctacaatc atcaaataaa                               30

<210> SEQ ID NO 226
<211> LENGTH: 18
<212> TYPE: DNA
<213> ORGANISM: Artificial Sequence
<220> FEATURE:
<223> OTHER INFORMATION: Synthetic primer

<400> SEQUENCE: 226
gggtaggagg ttgttatt                                            18

<210> SEQ ID NO 227
<211> LENGTH: 22
<212> TYPE: DNA
<213> ORGANISM: Artificial Sequence
<220> FEATURE:
<223> OTHER INFORMATION: Synthetic primer

<400> SEQUENCE: 227
aaacacttaa atctacaatc at                                       22

<210> SEQ ID NO 228
<211> LENGTH: 18
<212> TYPE: DNA
<213> ORGANISM: Artificial Sequence
<220> FEATURE:
<223> OTHER INFORMATION: Synthetic primer

<400> SEQUENCE: 228
tttagtttga ggatggtg                                            18

<210> SEQ ID NO 229
<211> LENGTH: 17
<212> TYPE: DNA
<213> ORGANISM: Artificial Sequence
<220> FEATURE:
<223> OTHER INFORMATION: Synthetic primer

<400> SEQUENCE: 229
caaacaaaca accacac                                             17

<210> SEQ ID NO 230
<211> LENGTH: 12
<212> TYPE: DNA
<213> ORGANISM: Artificial Sequence
<220> FEATURE:
<223> OTHER INFORMATION: Synthetic primer

<400> SEQUENCE: 230
ttatttgttt tt                                                  12

<210> SEQ ID NO 231
<211> LENGTH: 12

```
<212> TYPE: DNA
<213> ORGANISM: Artificial Sequence
<220> FEATURE:
<223> OTHER INFORMATION: Synthetic primer

<400> SEQUENCE: 231
ttattcgttt tt                                                              12

<210> SEQ ID NO 232
<211> LENGTH: 28
<212> TYPE: DNA
<213> ORGANISM: Artificial Sequence
<220> FEATURE:
<223> OTHER INFORMATION: Synthetic primer

<400> SEQUENCE: 232
tttgagatat attagagggt gggtatgt                                             28

<210> SEQ ID NO 233
<211> LENGTH: 22
<212> TYPE: DNA
<213> ORGANISM: Artificial Sequence
<220> FEATURE:
<223> OTHER INFORMATION: Synthetic primer

<400> SEQUENCE: 233
aacccactca aacaaacaac ca                                                   22

<210> SEQ ID NO 234
<211> LENGTH: 19
<212> TYPE: DNA
<213> ORGANISM: Artificial Sequence
<220> FEATURE:
<223> OTHER INFORMATION: Synthetic primer

<400> SEQUENCE: 234
ttgaggatgg tgttggttt                                                       19

<210> SEQ ID NO 235
<211> LENGTH: 22
<212> TYPE: DNA
<213> ORGANISM: Artificial Sequence
<220> FEATURE:
<223> OTHER INFORMATION: Synthetic primer

<400> SEQUENCE: 235
caccctcctc caaacataat aa                                                   22

<210> SEQ ID NO 236
<211> LENGTH: 25
<212> TYPE: DNA
<213> ORGANISM: Artificial Sequence
<220> FEATURE:
<223> OTHER INFORMATION: Synthetic primer

<400> SEQUENCE: 236
gggtaggagg ttgttatttta gtagg                                               25

<210> SEQ ID NO 237
<211> LENGTH: 30
<212> TYPE: DNA
<213> ORGANISM: Artificial Sequence
<220> FEATURE:
<223> OTHER INFORMATION: Synthetic primer

<400> SEQUENCE: 237
```

```
aaacacttaa atctacaatc atcaaataaa                                    30

<210> SEQ ID NO 238
<211> LENGTH: 18
<212> TYPE: DNA
<213> ORGANISM: Artificial Sequence
<220> FEATURE:
<223> OTHER INFORMATION: Synthetic primer

<400> SEQUENCE: 238
gggtaggagg ttgttatt                                                 18

<210> SEQ ID NO 239
<211> LENGTH: 22
<212> TYPE: DNA
<213> ORGANISM: Artificial Sequence
<220> FEATURE:
<223> OTHER INFORMATION: Synthetic primer

<400> SEQUENCE: 239
aaacacttaa atctacaatc at                                            22

<210> SEQ ID NO 240
<211> LENGTH: 12
<212> TYPE: DNA
<213> ORGANISM: Artificial Sequence
<220> FEATURE:
<223> OTHER INFORMATION: Synthetic primer

<400> SEQUENCE: 240
tgttttgtag tt                                                       12

<210> SEQ ID NO 241
<211> LENGTH: 12
<212> TYPE: DNA
<213> ORGANISM: Artificial Sequence
<220> FEATURE:
<223> OTHER INFORMATION: Synthetic primer

<400> SEQUENCE: 241
tgtttcgtag tt                                                       12

<210> SEQ ID NO 242
<211> LENGTH: 26
<212> TYPE: DNA
<213> ORGANISM: Artificial Sequence
<220> FEATURE:
<223> OTHER INFORMATION: Synthetic primer

<400> SEQUENCE: 242
gagatatatt agagggtggg tatgtt                                        26

<210> SEQ ID NO 243
<211> LENGTH: 24
<212> TYPE: DNA
<213> ORGANISM: Artificial Sequence
<220> FEATURE:
<223> OTHER INFORMATION: Synthetic primer

<400> SEQUENCE: 243
acaccctcct ccaaacataa taaa                                          24

<210> SEQ ID NO 244
<211> LENGTH: 22
<212> TYPE: DNA
<213> ORGANISM: Artificial Sequence
```

```
<220> FEATURE:
<223> OTHER INFORMATION: Synthetic primer

<400> SEQUENCE: 244
gggatagtag tgtaaagagt tt                                          22

<210> SEQ ID NO 245
<211> LENGTH: 22
<212> TYPE: DNA
<213> ORGANISM: Artificial Sequence
<220> FEATURE:
<223> OTHER INFORMATION: Synthetic primer

<400> SEQUENCE: 245
cctatcccta ctcacaacta aa                                          22

<210> SEQ ID NO 246
<211> LENGTH: 17
<212> TYPE: DNA
<213> ORGANISM: Artificial Sequence
<220> FEATURE:
<223> OTHER INFORMATION: Synthetic primer

<400> SEQUENCE: 246
tgaggatggt gttggtt                                                17

<210> SEQ ID NO 247
<211> LENGTH: 27
<212> TYPE: DNA
<213> ORGANISM: Artificial Sequence
<220> FEATURE:
<223> OTHER INFORMATION: Synthetic primer

<400> SEQUENCE: 247
cacttaaatc tacaatcatc aaataaa                                     27

<210> SEQ ID NO 248
<211> LENGTH: 21
<212> TYPE: DNA
<213> ORGANISM: Artificial Sequence
<220> FEATURE:
<223> OTHER INFORMATION: Synthetic primer

<400> SEQUENCE: 248
tttgtggttt agttagaatt t                                           21

<210> SEQ ID NO 249
<211> LENGTH: 22
<212> TYPE: DNA
<213> ORGANISM: Artificial Sequence
<220> FEATURE:
<223> OTHER INFORMATION: Synthetic primer

<400> SEQUENCE: 249
aaacacttaa atctacaatc at                                          22

<210> SEQ ID NO 250
<211> LENGTH: 11
<212> TYPE: DNA
<213> ORGANISM: Artificial Sequence
<220> FEATURE:
<223> OTHER INFORMATION: Synthetic primer

<400> SEQUENCE: 250
atgattgtag a                                                      11
```

```
<210> SEQ ID NO 251
<211> LENGTH: 11
<212> TYPE: DNA
<213> ORGANISM: Artificial Sequence
<220> FEATURE:
<223> OTHER INFORMATION: Synthetic primer

<400> SEQUENCE: 251
atgatcgtag a                                                          11

<210> SEQ ID NO 252
<211> LENGTH: 26
<212> TYPE: DNA
<213> ORGANISM: Artificial Sequence
<220> FEATURE:
<223> OTHER INFORMATION: Synthetic primer

<400> SEQUENCE: 252
gagatatatt agagggtggg tatgtt                                          26

<210> SEQ ID NO 253
<211> LENGTH: 24
<212> TYPE: DNA
<213> ORGANISM: Artificial Sequence
<220> FEATURE:
<223> OTHER INFORMATION: Synthetic primer

<400> SEQUENCE: 253
acaccctcct ccaaacataa taaa                                            24

<210> SEQ ID NO 254
<211> LENGTH: 17
<212> TYPE: DNA
<213> ORGANISM: Artificial Sequence
<220> FEATURE:
<223> OTHER INFORMATION: Synthetic primer

<400> SEQUENCE: 254
tgttttatgt tgtttgt                                                    17

<210> SEQ ID NO 255
<211> LENGTH: 17
<212> TYPE: DNA
<213> ORGANISM: Artificial Sequence
<220> FEATURE:
<223> OTHER INFORMATION: Synthetic primer

<400> SEQUENCE: 255
tgttttacgt tgtttgt                                                    17

<210> SEQ ID NO 256
<211> LENGTH: 26
<212> TYPE: DNA
<213> ORGANISM: Artificial Sequence
<220> FEATURE:
<223> OTHER INFORMATION: Synthetic primer

<400> SEQUENCE: 256
gagatatatt agagggtggg tatgtt                                          26

<210> SEQ ID NO 257
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 257
acaccctcct ccaaacataa taaa                                          24

<210> SEQ ID NO 258
<211> LENGTH: 30
<212> TYPE: DNA
<213> ORGANISM: Artificial Sequence
<220> FEATURE:
<223> OTHER INFORMATION: Synthetic primer

<400> SEQUENCE: 258
tttatttgat gattgtagat ttaagtgttt                                    30

<210> SEQ ID NO 259
<211> LENGTH: 18
<212> TYPE: DNA
<213> ORGANISM: Artificial Sequence
<220> FEATURE:
<223> OTHER INFORMATION: Synthetic primer

<400> SEQUENCE: 259
aaacaaccac accctcct                                                 18

<210> SEQ ID NO 260
<211> LENGTH: 20
<212> TYPE: DNA
<213> ORGANISM: Artificial Sequence
<220> FEATURE:
<223> OTHER INFORMATION: Synthetic primer

<400> SEQUENCE: 260
tatttgatga ttgtagattt                                               20

<210> SEQ ID NO 261
<211> LENGTH: 18
<212> TYPE: DNA
<213> ORGANISM: Artificial Sequence
<220> FEATURE:
<223> OTHER INFORMATION: Synthetic primer

<400> SEQUENCE: 261
cccatctcct aactataa                                                 18

<210> SEQ ID NO 262
<211> LENGTH: 12
<212> TYPE: DNA
<213> ORGANISM: Artificial Sequence
<220> FEATURE:
<223> OTHER INFORMATION: Synthetic primer

<400> SEQUENCE: 262
ttgggtgaat at                                                       12

<210> SEQ ID NO 263
<211> LENGTH: 12
<212> TYPE: DNA
<213> ORGANISM: Artificial Sequence
<220> FEATURE:
<223> OTHER INFORMATION: Synthetic primer

<400> SEQUENCE: 263
ttgggcgaat at                                                       12

<210> SEQ ID NO 264
```

```
<211> LENGTH: 26
<212> TYPE: DNA
<213> ORGANISM: Artificial Sequence
<220> FEATURE:
<223> OTHER INFORMATION: Synthetic primer

<400> SEQUENCE: 264
gagatatatt agagggtggg tatgtt                                          26

<210> SEQ ID NO 265
<211> LENGTH: 24
<212> TYPE: DNA
<213> ORGANISM: Artificial Sequence
<220> FEATURE:
<223> OTHER INFORMATION: Synthetic primer

<400> SEQUENCE: 265
acaccctcct ccaaacataa taaa                                            24

<210> SEQ ID NO 266
<211> LENGTH: 30
<212> TYPE: DNA
<213> ORGANISM: Artificial Sequence
<220> FEATURE:
<223> OTHER INFORMATION: Synthetic primer

<400> SEQUENCE: 266
tttatttgat gattgtagat ttaagtgttt                                      30

<210> SEQ ID NO 267
<211> LENGTH: 18
<212> TYPE: DNA
<213> ORGANISM: Artificial Sequence
<220> FEATURE:
<223> OTHER INFORMATION: Synthetic primer

<400> SEQUENCE: 267
aaacaaccac accctcct                                                   18

<210> SEQ ID NO 268
<211> LENGTH: 20
<212> TYPE: DNA
<213> ORGANISM: Artificial Sequence
<220> FEATURE:
<223> OTHER INFORMATION: Synthetic primer

<400> SEQUENCE: 268
tatttgatga ttgtagattt                                                 20

<210> SEQ ID NO 269
<211> LENGTH: 18
<212> TYPE: DNA
<213> ORGANISM: Artificial Sequence
<220> FEATURE:
<223> OTHER INFORMATION: Synthetic primer

<400> SEQUENCE: 269
cccatctcct aactataa                                                   18

<210> SEQ ID NO 270
<211> LENGTH: 14
<212> TYPE: DNA
<213> ORGANISM: Artificial Sequence
<220> FEATURE:
<223> OTHER INFORMATION: Synthetic primer

<400> SEQUENCE: 270
```

```
attatgtttg gagg                                                      14

<210> SEQ ID NO 271
<211> LENGTH: 14
<212> TYPE: DNA
<213> ORGANISM: Artificial Sequence
<220> FEATURE:
<223> OTHER INFORMATION: Synthetic primer

<400> SEQUENCE: 271
attacgttcg gagg                                                      14

<210> SEQ ID NO 272
<211> LENGTH: 30
<212> TYPE: DNA
<213> ORGANISM: Artificial Sequence
<220> FEATURE:
<223> OTHER INFORMATION: Synthetic primer

<400> SEQUENCE: 272
tttatttgat gattgtagat ttaagtgttt                                     30

<210> SEQ ID NO 273
<211> LENGTH: 20
<212> TYPE: DNA
<213> ORGANISM: Artificial Sequence
<220> FEATURE:
<223> OTHER INFORMATION: Synthetic primer

<400> SEQUENCE: 273
caaacaaaca accacaccct                                                20

<210> SEQ ID NO 274
<211> LENGTH: 20
<212> TYPE: DNA
<213> ORGANISM: Artificial Sequence
<220> FEATURE:
<223> OTHER INFORMATION: Synthetic primer

<400> SEQUENCE: 274
tatttgatga ttgtagattt                                                20

<210> SEQ ID NO 275
<211> LENGTH: 18
<212> TYPE: DNA
<213> ORGANISM: Artificial Sequence
<220> FEATURE:
<223> OTHER INFORMATION: Synthetic primer

<400> SEQUENCE: 275
cccatctcct aactataa                                                  18

<210> SEQ ID NO 276
<211> LENGTH: 15
<212> TYPE: DNA
<213> ORGANISM: Artificial Sequence
<220> FEATURE:
<223> OTHER INFORMATION: Synthetic primer

<400> SEQUENCE: 276
aggagggtgt ggttg                                                     15

<210> SEQ ID NO 277
<211> LENGTH: 15
<212> TYPE: DNA
```

```
<213> ORGANISM: Artificial Sequence
<220> FEATURE:
<223> OTHER INFORMATION: Synthetic primer

<400> SEQUENCE: 277
aggagggcgt ggttg                                                    15

<210> SEQ ID NO 278
<211> LENGTH: 25
<212> TYPE: DNA
<213> ORGANISM: Artificial Sequence
<220> FEATURE:
<223> OTHER INFORMATION: Synthetic primer

<400> SEQUENCE: 278
ttgatgattg tagatttaag tgttt                                         25

<210> SEQ ID NO 279
<211> LENGTH: 22
<212> TYPE: DNA
<213> ORGANISM: Artificial Sequence
<220> FEATURE:
<223> OTHER INFORMATION: Synthetic primer

<400> SEQUENCE: 279
aaatctaacc cactcaaaca aa                                            22

<210> SEQ ID NO 280
<211> LENGTH: 20
<212> TYPE: DNA
<213> ORGANISM: Artificial Sequence
<220> FEATURE:
<223> OTHER INFORMATION: Synthetic primer

<400> SEQUENCE: 280
tatttgatga ttgtagattt                                               20

<210> SEQ ID NO 281
<211> LENGTH: 18
<212> TYPE: DNA
<213> ORGANISM: Artificial Sequence
<220> FEATURE:
<223> OTHER INFORMATION: Synthetic primer

<400> SEQUENCE: 281
cccatctcct aactataa                                                 18

<210> SEQ ID NO 282
<211> LENGTH: 13
<212> TYPE: DNA
<213> ORGANISM: Artificial Sequence
<220> FEATURE:
<223> OTHER INFORMATION: Synthetic primer

<400> SEQUENCE: 282
ttttgttgtt agg                                                      13

<210> SEQ ID NO 283
<211> LENGTH: 13
<212> TYPE: DNA
<213> ORGANISM: Artificial Sequence
<220> FEATURE:
<223> OTHER INFORMATION: Synthetic primer

<400> SEQUENCE: 283
ttttgtcgtt agg                                                      13
```

<210> SEQ ID NO 284
<211> LENGTH: 25
<212> TYPE: DNA
<213> ORGANISM: Artificial Sequence
<220> FEATURE:
<223> OTHER INFORMATION: Synthetic primer

<400> SEQUENCE: 284
tggttgtttg tttgagtggg ttaga                                    25

<210> SEQ ID NO 285
<211> LENGTH: 21
<212> TYPE: DNA
<213> ORGANISM: Artificial Sequence
<220> FEATURE:
<223> OTHER INFORMATION: Synthetic primer

<400> SEQUENCE: 285
acccacatat cccacctcct t                                        21

<210> SEQ ID NO 286
<211> LENGTH: 20
<212> TYPE: DNA
<213> ORGANISM: Artificial Sequence
<220> FEATURE:
<223> OTHER INFORMATION: Synthetic primer

<400> SEQUENCE: 286
tttggaggag ggtgtggttg                                          20

<210> SEQ ID NO 287
<211> LENGTH: 30
<212> TYPE: DNA
<213> ORGANISM: Artificial Sequence
<220> FEATURE:
<223> OTHER INFORMATION: Synthetic primer

<400> SEQUENCE: 287
aacctaaaca aataatccca atacttctcc                               30

<210> SEQ ID NO 288
<211> LENGTH: 22
<212> TYPE: DNA
<213> ORGANISM: Artificial Sequence
<220> FEATURE:
<223> OTHER INFORMATION: Synthetic primer

<400> SEQUENCE: 288
gagggtgtgg ttgtttgttt ga                                       22

<210> SEQ ID NO 289
<211> LENGTH: 20
<212> TYPE: DNA
<213> ORGANISM: Artificial Sequence
<220> FEATURE:
<223> OTHER INFORMATION: Synthetic primer

<400> SEQUENCE: 289
cccaacaccc acatatccca                                          20

<210> SEQ ID NO 290
<211> LENGTH: 18
<212> TYPE: DNA
<213> ORGANISM: Artificial Sequence
<220> FEATURE:

<223> OTHER INFORMATION: Synthetic primer

<400> SEQUENCE: 290
ttatgtttgg aggagggt                                                    18

<210> SEQ ID NO 291
<211> LENGTH: 24
<212> TYPE: DNA
<213> ORGANISM: Artificial Sequence
<220> FEATURE:
<223> OTHER INFORMATION: Synthetic primer

<400> SEQUENCE: 291
aaacctaaac aaataatccc aata                                             24

<210> SEQ ID NO 292
<211> LENGTH: 21
<212> TYPE: DNA
<213> ORGANISM: Artificial Sequence
<220> FEATURE:
<223> OTHER INFORMATION: Synthetic primer

<400> SEQUENCE: 292
tgattgtaga tttaagtgtt t                                                21

<210> SEQ ID NO 293
<211> LENGTH: 19
<212> TYPE: DNA
<213> ORGANISM: Artificial Sequence
<220> FEATURE:
<223> OTHER INFORMATION: Synthetic primer

<400> SEQUENCE: 293
cccatctcct aactataaa                                                   19

<210> SEQ ID NO 294
<211> LENGTH: 11
<212> TYPE: DNA
<213> ORGANISM: Artificial Sequence
<220> FEATURE:
<223> OTHER INFORMATION: Synthetic primer

<400> SEQUENCE: 294
ttttatggta g                                                           11

<210> SEQ ID NO 295
<211> LENGTH: 11
<212> TYPE: DNA
<213> ORGANISM: Artificial Sequence
<220> FEATURE:
<223> OTHER INFORMATION: Synthetic primer

<400> SEQUENCE: 295
ttttacggta g                                                           11

<210> SEQ ID NO 296
<211> LENGTH: 25
<212> TYPE: DNA
<213> ORGANISM: Artificial Sequence
<220> FEATURE:
<223> OTHER INFORMATION: Synthetic primer

<400> SEQUENCE: 296
tggttgtttg tttgagtggg ttaga                                            25

```
<210> SEQ ID NO 297
<211> LENGTH: 21
<212> TYPE: DNA
<213> ORGANISM: Artificial Sequence
<220> FEATURE:
<223> OTHER INFORMATION: Synthetic primer

<400> SEQUENCE: 297
acccacatat cccacctcct t                                              21

<210> SEQ ID NO 298
<211> LENGTH: 20
<212> TYPE: DNA
<213> ORGANISM: Artificial Sequence
<220> FEATURE:
<223> OTHER INFORMATION: Synthetic primer

<400> SEQUENCE: 298
tttggaggag ggtgtggttg                                                20

<210> SEQ ID NO 299
<211> LENGTH: 30
<212> TYPE: DNA
<213> ORGANISM: Artificial Sequence
<220> FEATURE:
<223> OTHER INFORMATION: Synthetic primer

<400> SEQUENCE: 299
aacctaaaca aataatccca atacttctcc                                     30

<210> SEQ ID NO 300
<211> LENGTH: 22
<212> TYPE: DNA
<213> ORGANISM: Artificial Sequence
<220> FEATURE:
<223> OTHER INFORMATION: Synthetic primer

<400> SEQUENCE: 300
gagggtgtgg ttgtttgttt ga                                             22

<210> SEQ ID NO 301
<211> LENGTH: 20
<212> TYPE: DNA
<213> ORGANISM: Artificial Sequence
<220> FEATURE:
<223> OTHER INFORMATION: Synthetic primer

<400> SEQUENCE: 301
cccaacaccc acatatccca                                                20

<210> SEQ ID NO 302
<211> LENGTH: 18
<212> TYPE: DNA
<213> ORGANISM: Artificial Sequence
<220> FEATURE:
<223> OTHER INFORMATION: Synthetic primer

<400> SEQUENCE: 302
ttatgtttgg aggagggt                                                  18

<210> SEQ ID NO 303
<211> LENGTH: 24
<212> TYPE: DNA
<213> ORGANISM: Artificial Sequence
<220> FEATURE:
<223> OTHER INFORMATION: Synthetic primer
```

<400> SEQUENCE: 303
aaacctaaac aaataatccc aata                                            24

<210> SEQ ID NO 304
<211> LENGTH: 21
<212> TYPE: DNA
<213> ORGANISM: Artificial Sequence
<220> FEATURE:
<223> OTHER INFORMATION: Synthetic primer

<400> SEQUENCE: 304
tgattgtaga tttaagtgtt t                                               21

<210> SEQ ID NO 305
<211> LENGTH: 19
<212> TYPE: DNA
<213> ORGANISM: Artificial Sequence
<220> FEATURE:
<223> OTHER INFORMATION: Synthetic primer

<400> SEQUENCE: 305
cccatctcct aactataaa                                                  19

<210> SEQ ID NO 306
<211> LENGTH: 13
<212> TYPE: DNA
<213> ORGANISM: Artificial Sequence
<220> FEATURE:
<223> OTHER INFORMATION: Synthetic primer

<400> SEQUENCE: 306
tgtgggtgtt ggg                                                        13

<210> SEQ ID NO 307
<211> LENGTH: 13
<212> TYPE: DNA
<213> ORGANISM: Artificial Sequence
<220> FEATURE:
<223> OTHER INFORMATION: Synthetic primer

<400> SEQUENCE: 307
tgtgggcgtt ggg                                                        13

<210> SEQ ID NO 308
<211> LENGTH: 30
<212> TYPE: DNA
<213> ORGANISM: Artificial Sequence
<220> FEATURE:
<223> OTHER INFORMATION: Synthetic primer

<400> SEQUENCE: 308
gggagaagta ttgggattat ttgtttaggt                                      30

<210> SEQ ID NO 309
<211> LENGTH: 20
<212> TYPE: DNA
<213> ORGANISM: Artificial Sequence
<220> FEATURE:
<223> OTHER INFORMATION: Synthetic primer

<400> SEQUENCE: 309
acactcccac ccatctccaa                                                 20

<210> SEQ ID NO 310
<211> LENGTH: 17

```
<212> TYPE: DNA
<213> ORGANISM: Artificial Sequence
<220> FEATURE:
<223> OTHER INFORMATION: Synthetic primer

<400> SEQUENCE: 310
gggaaggagg tgggata                                                    17

<210> SEQ ID NO 311
<211> LENGTH: 21
<212> TYPE: DNA
<213> ORGANISM: Artificial Sequence
<220> FEATURE:
<223> OTHER INFORMATION: Synthetic primer

<400> SEQUENCE: 311
ccatctccaa ccaaactaaa c                                               21

<210> SEQ ID NO 312
<211> LENGTH: 23
<212> TYPE: DNA
<213> ORGANISM: Artificial Sequence
<220> FEATURE:
<223> OTHER INFORMATION: Synthetic primer

<400> SEQUENCE: 312
gggagaagta ttgggattat ttg                                             23

<210> SEQ ID NO 313
<211> LENGTH: 20
<212> TYPE: DNA
<213> ORGANISM: Artificial Sequence
<220> FEATURE:
<223> OTHER INFORMATION: Synthetic primer

<400> SEQUENCE: 313
ctacccacca accctaaatc                                                 20

<210> SEQ ID NO 314
<211> LENGTH: 19
<212> TYPE: DNA
<213> ORGANISM: Artificial Sequence
<220> FEATURE:
<223> OTHER INFORMATION: Synthetic primer

<400> SEQUENCE: 314
tttgtttgag tgggttaga                                                  19

<210> SEQ ID NO 315
<211> LENGTH: 23
<212> TYPE: DNA
<213> ORGANISM: Artificial Sequence
<220> FEATURE:
<223> OTHER INFORMATION: Synthetic primer

<400> SEQUENCE: 315
ccacactaaa tataaaccta caa                                             23

<210> SEQ ID NO 316
<211> LENGTH: 19
<212> TYPE: DNA
<213> ORGANISM: Artificial Sequence
<220> FEATURE:
<223> OTHER INFORMATION: Synthetic primer

<400> SEQUENCE: 316
```

```
tttatagtta ggagatggg                                                    19

<210> SEQ ID NO 317
<211> LENGTH: 19
<212> TYPE: DNA
<213> ORGANISM: Artificial Sequence
<220> FEATURE:
<223> OTHER INFORMATION: Synthetic primer

<400> SEQUENCE: 317
ccaaactaaa cccaaatta                                                    19

<210> SEQ ID NO 318
<211> LENGTH: 13
<212> TYPE: DNA
<213> ORGANISM: Artificial Sequence
<220> FEATURE:
<223> OTHER INFORMATION: Synthetic primer

<400> SEQUENCE: 318
ttagtttggt tgg                                                          13

<210> SEQ ID NO 319
<211> LENGTH: 13
<212> TYPE: DNA
<213> ORGANISM: Artificial Sequence
<220> FEATURE:
<223> OTHER INFORMATION: Synthetic primer

<400> SEQUENCE: 319
ttagttcggt tgg                                                          13

<210> SEQ ID NO 320
<211> LENGTH: 21
<212> TYPE: DNA
<213> ORGANISM: Artificial Sequence
<220> FEATURE:
<223> OTHER INFORMATION: Synthetic primer

<400> SEQUENCE: 320
ggaggtggga tatgtgggtg t                                                 21

<210> SEQ ID NO 321
<211> LENGTH: 23
<212> TYPE: DNA
<213> ORGANISM: Artificial Sequence
<220> FEATURE:
<223> OTHER INFORMATION: Synthetic primer

<400> SEQUENCE: 321
acctacccac caaccctaaa tca                                               23

<210> SEQ ID NO 322
<211> LENGTH: 30
<212> TYPE: DNA
<213> ORGANISM: Artificial Sequence
<220> FEATURE:
<223> OTHER INFORMATION: Synthetic primer

<400> SEQUENCE: 322
gggagaagta ttgggattat ttgtttaggt                                        30

<210> SEQ ID NO 323
<211> LENGTH: 22
<212> TYPE: DNA
<213> ORGANISM: Artificial Sequence
```

```
<220> FEATURE:
<223> OTHER INFORMATION: Synthetic primer

<400> SEQUENCE: 323
acaataccca cctacccacc aa                                        22

<210> SEQ ID NO 324
<211> LENGTH: 30
<212> TYPE: DNA
<213> ORGANISM: Artificial Sequence
<220> FEATURE:
<223> OTHER INFORMATION: Synthetic primer

<400> SEQUENCE: 324
gtttgtaggt ttatatttag tgtgggtgat                                30

<210> SEQ ID NO 325
<211> LENGTH: 23
<212> TYPE: DNA
<213> ORGANISM: Artificial Sequence
<220> FEATURE:
<223> OTHER INFORMATION: Synthetic primer

<400> SEQUENCE: 325
ctaaatcaca ctcccaccca tct                                       23

<210> SEQ ID NO 326
<211> LENGTH: 17
<212> TYPE: DNA
<213> ORGANISM: Artificial Sequence
<220> FEATURE:
<223> OTHER INFORMATION: Synthetic primer

<400> SEQUENCE: 326
gggaaggagg tgggata                                              17

<210> SEQ ID NO 327
<211> LENGTH: 19
<212> TYPE: DNA
<213> ORGANISM: Artificial Sequence
<220> FEATURE:
<223> OTHER INFORMATION: Synthetic primer

<400> SEQUENCE: 327
accctaaatc acactccca                                            19

<210> SEQ ID NO 328
<211> LENGTH: 19
<212> TYPE: DNA
<213> ORGANISM: Artificial Sequence
<220> FEATURE:
<223> OTHER INFORMATION: Synthetic primer

<400> SEQUENCE: 328
gggagaagta ttgggatta                                            19

<210> SEQ ID NO 329
<211> LENGTH: 18
<212> TYPE: DNA
<213> ORGANISM: Artificial Sequence
<220> FEATURE:
<223> OTHER INFORMATION: Synthetic primer

<400> SEQUENCE: 329
aaacacaata cccaccta                                             18
```

```
<210> SEQ ID NO 330
<211> LENGTH: 11
<212> TYPE: DNA
<213> ORGANISM: Artificial Sequence
<220> FEATURE:
<223> OTHER INFORMATION: Synthetic primer

<400> SEQUENCE: 330
agtgtgattt a                                                              11

<210> SEQ ID NO 331
<211> LENGTH: 11
<212> TYPE: DNA
<213> ORGANISM: Artificial Sequence
<220> FEATURE:
<223> OTHER INFORMATION: Synthetic primer

<400> SEQUENCE: 331
agtgcgattt a                                                              11

<210> SEQ ID NO 332
<211> LENGTH: 30
<212> TYPE: DNA
<213> ORGANISM: Artificial Sequence
<220> FEATURE:
<223> OTHER INFORMATION: Synthetic primer

<400> SEQUENCE: 332
gggagaagta ttgggattat ttgtttaggt                                          30

<210> SEQ ID NO 333
<211> LENGTH: 22
<212> TYPE: DNA
<213> ORGANISM: Artificial Sequence
<220> FEATURE:
<223> OTHER INFORMATION: Synthetic primer

<400> SEQUENCE: 333
acaataccca cctacccacc aa                                                  22

<210> SEQ ID NO 334
<211> LENGTH: 25
<212> TYPE: DNA
<213> ORGANISM: Artificial Sequence
<220> FEATURE:
<223> OTHER INFORMATION: Synthetic primer

<400> SEQUENCE: 334
aatttgggtt tagtttggtt ggaga                                               25

<210> SEQ ID NO 335
<211> LENGTH: 11
<212> TYPE: DNA
<213> ORGANISM: Artificial Sequence
<220> FEATURE:
<223> OTHER INFORMATION: Synthetic primer

<400> SEQUENCE: 335
agtgtgattt a                                                              11

<210> SEQ ID NO 336
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 336
cacccaactc cacctaccc                                              19

<210> SEQ ID NO 337
<211> LENGTH: 21
<212> TYPE: DNA
<213> ORGANISM: Artificial Sequence
<220> FEATURE:
<223> OTHER INFORMATION: Synthetic primer

<400> SEQUENCE: 337
tttaatttgg gtttagtttg g                                           21

<210> SEQ ID NO 338
<211> LENGTH: 11
<212> TYPE: DNA
<213> ORGANISM: Artificial Sequence
<220> FEATURE:
<223> OTHER INFORMATION: Synthetic primer

<400> SEQUENCE: 338
agtgtgattt a                                                      11

<210> SEQ ID NO 339
<211> LENGTH: 18
<212> TYPE: DNA
<213> ORGANISM: Artificial Sequence
<220> FEATURE:
<223> OTHER INFORMATION: Synthetic primer

<400> SEQUENCE: 339
aacacaatac ccacctac                                               18

<210> SEQ ID NO 340
<211> LENGTH: 11
<212> TYPE: DNA
<213> ORGANISM: Artificial Sequence
<220> FEATURE:
<223> OTHER INFORMATION: Synthetic primer

<400> SEQUENCE: 340
ttggtgggta g                                                      11

<210> SEQ ID NO 341
<211> LENGTH: 11
<212> TYPE: DNA
<213> ORGANISM: Artificial Sequence
<220> FEATURE:
<223> OTHER INFORMATION: Synthetic primer

<400> SEQUENCE: 341
ttggcgggta g                                                      11

<210> SEQ ID NO 342
<211> LENGTH: 23
<212> TYPE: DNA
<213> ORGANISM: Artificial Sequence
<220> FEATURE:
<223> OTHER INFORMATION: Synthetic primer

<400> SEQUENCE: 342
gagatgggtg ggagtgtgat tta                                         23

<210> SEQ ID NO 343

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 343
cacccaactc cacctaccc                                                    19

<210> SEQ ID NO 344
<211> LENGTH: 19
<212> TYPE: DNA
<213> ORGANISM: Artificial Sequence
<220> FEATURE:
<223> OTHER INFORMATION: Synthetic primer

<400> SEQUENCE: 344
ttggagatgg gtgggagtg                                                    19

<210> SEQ ID NO 345
<211> LENGTH: 24
<212> TYPE: DNA
<213> ORGANISM: Artificial Sequence
<220> FEATURE:
<223> OTHER INFORMATION: Synthetic primer

<400> SEQUENCE: 345
aaactacaaa ctacctacac caaa                                              24

<210> SEQ ID NO 346
<211> LENGTH: 9
<212> TYPE: DNA
<213> ORGANISM: Artificial Sequence
<220> FEATURE:
<223> OTHER INFORMATION: Synthetic primer

<400> SEQUENCE: 346 aggtgggta                                                                9

<210> SEQ ID NO 347
<211> LENGTH: 9
<212> TYPE: DNA
<213> ORGANISM: Artificial Sequence
<220> FEATURE:
<223> OTHER INFORMATION: Synthetic primer

<400> SEQUENCE: 347 aggcgggta                                                                9

<210> SEQ ID NO 348
<211> LENGTH: 23
<212> TYPE: DNA
<213> ORGANISM: Artificial Sequence
<220> FEATURE:
<223> OTHER INFORMATION: Synthetic primer

<400> SEQUENCE: 348
gagatgggtg ggagtgtgat tta                                               23

<210> SEQ ID NO 349
<211> LENGTH: 19
<212> TYPE: DNA
<213> ORGANISM: Artificial Sequence
<220> FEATURE:
<223> OTHER INFORMATION: Synthetic primer

<400> SEQUENCE: 349
```
cacccaactc cacctaccc                                         19

<210> SEQ ID NO 350
<211> LENGTH: 19
<212> TYPE: DNA
<213> ORGANISM: Artificial Sequence
<220> FEATURE:
<223> OTHER INFORMATION: Synthetic primer

<400> SEQUENCE: 350
ttggagatgg gtgggagtg                                         19

<210> SEQ ID NO 351
<211> LENGTH: 24
<212> TYPE: DNA
<213> ORGANISM: Artificial Sequence
<220> FEATURE:
<223> OTHER INFORMATION: Synthetic primer

<400> SEQUENCE: 351
aaactacaaa ctacctacac caaa                                   24

<210> SEQ ID NO 352
<211> LENGTH: 18
<212> TYPE: DNA
<213> ORGANISM: Artificial Sequence
<220> FEATURE:
<223> OTHER INFORMATION: Synthetic primer

<400> SEQUENCE: 352
gatttagggt tggtgggt                                          18

<210> SEQ ID NO 353
<211> LENGTH: 21
<212> TYPE: DNA
<213> ORGANISM: Artificial Sequence
<220> FEATURE:
<223> OTHER INFORMATION: Synthetic primer

<400> SEQUENCE: 353
ccacaatacc acacttctac a                                      21

<210> SEQ ID NO 354
<211> LENGTH: 15
<212> TYPE: DNA
<213> ORGANISM: Artificial Sequence
<220> FEATURE:
<223> OTHER INFORMATION: Synthetic primer

<400> SEQUENCE: 354
tgttttgttg ttgtt                                             15

<210> SEQ ID NO 355
<211> LENGTH: 15
<212> TYPE: DNA
<213> ORGANISM: Artificial Sequence
<220> FEATURE:
<223> OTHER INFORMATION: Synthetic primer

<400> SEQUENCE: 355
tgtttcgtcg ttgtt                                             15

<210> SEQ ID NO 356
<211> LENGTH: 23
<212> TYPE: DNA

```
<213> ORGANISM: Artificial Sequence
<220> FEATURE:
<223> OTHER INFORMATION: Synthetic primer

<400> SEQUENCE: 356
gagatgggtg ggagtgtgat tta                                          23

<210> SEQ ID NO 357
<211> LENGTH: 19
<212> TYPE: DNA
<213> ORGANISM: Artificial Sequence
<220> FEATURE:
<223> OTHER INFORMATION: Synthetic primer

<400> SEQUENCE: 357
cacccaactc cacctaccc                                               19

<210> SEQ ID NO 358
<211> LENGTH: 20
<212> TYPE: DNA
<213> ORGANISM: Artificial Sequence
<220> FEATURE:
<223> OTHER INFORMATION: Synthetic primer

<400> SEQUENCE: 358
tttagggttg gtgggtaggt                                              20

<210> SEQ ID NO 359
<211> LENGTH: 25
<212> TYPE: DNA
<213> ORGANISM: Artificial Sequence
<220> FEATURE:
<223> OTHER INFORMATION: Synthetic primer

<400> SEQUENCE: 359
ttccacaata ccacacttct acaaa                                        25

<210> SEQ ID NO 360
<211> LENGTH: 19
<212> TYPE: DNA
<213> ORGANISM: Artificial Sequence
<220> FEATURE:
<223> OTHER INFORMATION: Synthetic primer

<400> SEQUENCE: 360
ttggagatgg gtgggagtg                                               19

<210> SEQ ID NO 361
<211> LENGTH: 24
<212> TYPE: DNA
<213> ORGANISM: Artificial Sequence
<220> FEATURE:
<223> OTHER INFORMATION: Synthetic primer

<400> SEQUENCE: 361
aaactacaaa ctacctacac caaa                                         24

<210> SEQ ID NO 362
<211> LENGTH: 19
<212> TYPE: DNA
<213> ORGANISM: Artificial Sequence
<220> FEATURE:
<223> OTHER INFORMATION: Synthetic primer

<400> SEQUENCE: 362
gtaggtgggt attgtgttt                                               19
```

<210> SEQ ID NO 363
<211> LENGTH: 23
<212> TYPE: DNA
<213> ORGANISM: Artificial Sequence
<220> FEATURE:
<223> OTHER INFORMATION: Synthetic primer

<400> SEQUENCE: 363
ctaatacaac attattccac aat                                              23

<210> SEQ ID NO 364
<211> LENGTH: 11
<212> TYPE: DNA
<213> ORGANISM: Artificial Sequence
<220> FEATURE:
<223> OTHER INFORMATION: Synthetic primer

<400> SEQUENCE: 364
tgttttggaa t                                                           11

<210> SEQ ID NO 365
<211> LENGTH: 11
<212> TYPE: DNA
<213> ORGANISM: Artificial Sequence
<220> FEATURE:
<223> OTHER INFORMATION: Synthetic primer

<400> SEQUENCE: 365
tgtttcggaa t                                                           11

<210> SEQ ID NO 366
<211> LENGTH: 23
<212> TYPE: DNA
<213> ORGANISM: Artificial Sequence
<220> FEATURE:
<223> OTHER INFORMATION: Synthetic primer

<400> SEQUENCE: 366
gagatgggtg ggagtgtgat tta                                              23

<210> SEQ ID NO 367
<211> LENGTH: 19
<212> TYPE: DNA
<213> ORGANISM: Artificial Sequence
<220> FEATURE:
<223> OTHER INFORMATION: Synthetic primer

<400> SEQUENCE: 367
cacccaactc cacctaccc                                                   19

<210> SEQ ID NO 368
<211> LENGTH: 20
<212> TYPE: DNA
<213> ORGANISM: Artificial Sequence
<220> FEATURE:
<223> OTHER INFORMATION: Synthetic primer

<400> SEQUENCE: 368
tttagggttg gtgggtaggt                                                  20

<210> SEQ ID NO 369
<211> LENGTH: 25
<212> TYPE: DNA
<213> ORGANISM: Artificial Sequence
<220> FEATURE:

<223> OTHER INFORMATION: Synthetic primer

<400> SEQUENCE: 369
ttccacaata ccacacttct acaaa         25

<210> SEQ ID NO 370
<211> LENGTH: 19
<212> TYPE: DNA
<213> ORGANISM: Artificial Sequence
<220> FEATURE:
<223> OTHER INFORMATION: Synthetic primer

<400> SEQUENCE: 370
ttggagatgg gtgggagtg          19

<210> SEQ ID NO 371
<211> LENGTH: 24
<212> TYPE: DNA
<213> ORGANISM: Artificial Sequence
<220> FEATURE:
<223> OTHER INFORMATION: Synthetic primer

<400> SEQUENCE: 371
aaactacaaa ctacctacac caaa          24

<210> SEQ ID NO 372
<211> LENGTH: 19
<212> TYPE: DNA
<213> ORGANISM: Artificial Sequence
<220> FEATURE:
<223> OTHER INFORMATION: Synthetic primer

<400> SEQUENCE: 372
gtaggtgggt attgtgttt          19

<210> SEQ ID NO 373
<211> LENGTH: 23
<212> TYPE: DNA
<213> ORGANISM: Artificial Sequence
<220> FEATURE:
<223> OTHER INFORMATION: Synthetic primer

<400> SEQUENCE: 373
ctaatacaac attattccac aat          23

<210> SEQ ID NO 374
<211> LENGTH: 18
<212> TYPE: DNA
<213> ORGANISM: Artificial Sequence
<220> FEATURE:
<223> OTHER INFORMATION: Synthetic primer

<400> SEQUENCE: 374
ttttgtgtgg tatgtttt          18

<210> SEQ ID NO 375
<211> LENGTH: 18
<212> TYPE: DNA
<213> ORGANISM: Artificial Sequence
<220> FEATURE:
<223> OTHER INFORMATION: Synthetic primer

<400> SEQUENCE: 375
ttttgcgcgg tatgtttt          18

```
<210> SEQ ID NO 376
<211> LENGTH: 23
<212> TYPE: DNA
<213> ORGANISM: Artificial Sequence
<220> FEATURE:
<223> OTHER INFORMATION: Synthetic primer

<400> SEQUENCE: 376
gagatgggtg ggagtgtgat tta                                          23

<210> SEQ ID NO 377
<211> LENGTH: 19
<212> TYPE: DNA
<213> ORGANISM: Artificial Sequence
<220> FEATURE:
<223> OTHER INFORMATION: Synthetic primer

<400> SEQUENCE: 377
cacccaactc cacctaccc                                               19

<210> SEQ ID NO 378
<211> LENGTH: 20
<212> TYPE: DNA
<213> ORGANISM: Artificial Sequence
<220> FEATURE:
<223> OTHER INFORMATION: Synthetic primer

<400> SEQUENCE: 378
tttagggttg gtgggtaggt                                              20

<210> SEQ ID NO 379
<211> LENGTH: 25
<212> TYPE: DNA
<213> ORGANISM: Artificial Sequence
<220> FEATURE:
<223> OTHER INFORMATION: Synthetic primer

<400> SEQUENCE: 379
ttccacaata ccacacttct acaaa                                        25

<210> SEQ ID NO 380
<211> LENGTH: 19
<212> TYPE: DNA
<213> ORGANISM: Artificial Sequence
<220> FEATURE:
<223> OTHER INFORMATION: Synthetic primer

<400> SEQUENCE: 380
ttggagatgg gtgggagtg                                               19

<210> SEQ ID NO 381
<211> LENGTH: 24
<212> TYPE: DNA
<213> ORGANISM: Artificial Sequence
<220> FEATURE:
<223> OTHER INFORMATION: Synthetic primer

<400> SEQUENCE: 381
aaactacaaa ctacctacac caaa                                         24

<210> SEQ ID NO 382
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 382
gtaggtgggt attgtgttt                                              19

<210> SEQ ID NO 383
<211> LENGTH: 23
<212> TYPE: DNA
<213> ORGANISM: Artificial Sequence
<220> FEATURE:
<223> OTHER INFORMATION: Synthetic primer

<400> SEQUENCE: 383
ctaatacaac attattccac aat                                         23

<210> SEQ ID NO 384
<211> LENGTH: 12
<212> TYPE: DNA
<213> ORGANISM: Artificial Sequence
<220> FEATURE:
<223> OTHER INFORMATION: Synthetic primer

<400> SEQUENCE: 384
ttgggtgggg gt                                                     12

<210> SEQ ID NO 385
<211> LENGTH: 12
<212> TYPE: DNA
<213> ORGANISM: Artificial Sequence
<220> FEATURE:
<223> OTHER INFORMATION: Synthetic primer

<400> SEQUENCE: 385
ttgggcgggg gt                                                     12

<210> SEQ ID NO 386
<211> LENGTH: 20
<212> TYPE: DNA
<213> ORGANISM: Artificial Sequence
<220> FEATURE:
<223> OTHER INFORMATION: Synthetic primer

<400> SEQUENCE: 386
tttagggttg gtgggtaggt                                             20

<210> SEQ ID NO 387
<211> LENGTH: 25
<212> TYPE: DNA
<213> ORGANISM: Artificial Sequence
<220> FEATURE:
<223> OTHER INFORMATION: Synthetic primer

<400> SEQUENCE: 387
ttccacaata ccacacttct acaaa                                       25

<210> SEQ ID NO 388
<211> LENGTH: 19
<212> TYPE: DNA
<213> ORGANISM: Artificial Sequence
<220> FEATURE:
<223> OTHER INFORMATION: Synthetic primer

<400> SEQUENCE: 388
gatgggtggg agtgtgatt                                              19

<210> SEQ ID NO 389
<211> LENGTH: 24

```
<212> TYPE: DNA
<213> ORGANISM: Artificial Sequence
<220> FEATURE:
<223> OTHER INFORMATION: Synthetic primer

<400> SEQUENCE: 389
aaactacaaa ctacctacac caaa                                          24

<210> SEQ ID NO 390
<211> LENGTH: 19
<212> TYPE: DNA
<213> ORGANISM: Artificial Sequence
<220> FEATURE:
<223> OTHER INFORMATION: Synthetic primer

<400> SEQUENCE: 390
gtaggtgggt attgtgttt                                                19

<210> SEQ ID NO 391
<211> LENGTH: 23
<212> TYPE: DNA
<213> ORGANISM: Artificial Sequence
<220> FEATURE:
<223> OTHER INFORMATION: Synthetic primer

<400> SEQUENCE: 391
ctaatacaac attattccac aat                                           23

<210> SEQ ID NO 392
<211> LENGTH: 13
<212> TYPE: DNA
<213> ORGANISM: Artificial Sequence
<220> FEATURE:
<223> OTHER INFORMATION: Synthetic primer

<400> SEQUENCE: 392
tagaagtgtg gta                                                      13

<210> SEQ ID NO 393
<211> LENGTH: 13
<212> TYPE: DNA
<213> ORGANISM: Artificial Sequence
<220> FEATURE:
<223> OTHER INFORMATION: Synthetic primer

<400> SEQUENCE: 393
tagaagcgtg gta                                                      13

<210> SEQ ID NO 394
<211> LENGTH: 24
<212> TYPE: DNA
<213> ORGANISM: Artificial Sequence
<220> FEATURE:
<223> OTHER INFORMATION: Synthetic primer

<400> SEQUENCE: 394
tttggtgtag gtagtttgta gttt                                          24

<210> SEQ ID NO 395
<211> LENGTH: 26
<212> TYPE: DNA
<213> ORGANISM: Artificial Sequence
<220> FEATURE:
<223> OTHER INFORMATION: Synthetic primer

<400> SEQUENCE: 395
```
aactttattc catctctctc aataca                                              26

<210> SEQ ID NO 396
<211> LENGTH: 18
<212> TYPE: DNA
<213> ORGANISM: Artificial Sequence
<220> FEATURE:
<223> OTHER INFORMATION: Synthetic primer

<400> SEQUENCE: 396
gggtaggtgg agttgggt                                                       18

<210> SEQ ID NO 397
<211> LENGTH: 30
<212> TYPE: DNA
<213> ORGANISM: Artificial Sequence
<220> FEATURE:
<223> OTHER INFORMATION: Synthetic primer

<400> SEQUENCE: 397
aacaaatact aatacaacat tattccacaa                                          30

<210> SEQ ID NO 398
<211> LENGTH: 17
<212> TYPE: DNA
<213> ORGANISM: Artificial Sequence
<220> FEATURE:
<223> OTHER INFORMATION: Synthetic primer

<400> SEQUENCE: 398
tttggtgtag gtagttt                                                        17

<210> SEQ ID NO 399
<211> LENGTH: 22
<212> TYPE: DNA
<213> ORGANISM: Artificial Sequence
<220> FEATURE:
<223> OTHER INFORMATION: Synthetic primer

<400> SEQUENCE: 399
caataattct ccaactaata aa                                                  22

<210> SEQ ID NO 400
<211> LENGTH: 13
<212> TYPE: DNA
<213> ORGANISM: Artificial Sequence
<220> FEATURE:
<223> OTHER INFORMATION: Synthetic primer

<400> SEQUENCE: 400
attagatgta gtt                                                            13

<210> SEQ ID NO 401
<211> LENGTH: 13
<212> TYPE: DNA
<213> ORGANISM: Artificial Sequence
<220> FEATURE:
<223> OTHER INFORMATION: Synthetic primer

<400> SEQUENCE: 401
attagacgta gtt                                                            13

<210> SEQ ID NO 402
<211> LENGTH: 27
<212> TYPE: DNA
<213> ORGANISM: Artificial Sequence

```
<220> FEATURE:
<223> OTHER INFORMATION: Synthetic primer

<400> SEQUENCE: 402
tgtagaagtg tggtattgtg gaataat                                    27

<210> SEQ ID NO 403
<211> LENGTH: 29
<212> TYPE: DNA
<213> ORGANISM: Artificial Sequence
<220> FEATURE:
<223> OTHER INFORMATION: Synthetic primer

<400> SEQUENCE: 403
aaactttatt ccatctctct caatacaaa                                  29

<210> SEQ ID NO 404
<211> LENGTH: 21
<212> TYPE: DNA
<213> ORGANISM: Artificial Sequence
<220> FEATURE:
<223> OTHER INFORMATION: Synthetic primer

<400> SEQUENCE: 404
tttgtagaag tgtggtattg t                                          21

<210> SEQ ID NO 405
<211> LENGTH: 22
<212> TYPE: DNA
<213> ORGANISM: Artificial Sequence
<220> FEATURE:
<223> OTHER INFORMATION: Synthetic primer

<400> SEQUENCE: 405
aaactttatt ccatctctct ca                                         22

<210> SEQ ID NO 406
<211> LENGTH: 11
<212> TYPE: DNA
<213> ORGANISM: Artificial Sequence
<220> FEATURE:
<223> OTHER INFORMATION: Synthetic primer

<400> SEQUENCE: 406
tagtttgtag g                                                     11

<210> SEQ ID NO 407
<211> LENGTH: 11
<212> TYPE: DNA
<213> ORGANISM: Artificial Sequence
<220> FEATURE:
<223> OTHER INFORMATION: Synthetic primer

<400> SEQUENCE: 407
tagttcgtag g                                                     11

<210> SEQ ID NO 408
<211> LENGTH: 27
<212> TYPE: DNA
<213> ORGANISM: Artificial Sequence
<220> FEATURE:
<223> OTHER INFORMATION: Synthetic primer

<400> SEQUENCE: 408
tgtagaagtg tggtattgtg gaataat                                    27
```

```
<210> SEQ ID NO 409
<211> LENGTH: 29
<212> TYPE: DNA
<213> ORGANISM: Artificial Sequence
<220> FEATURE:
<223> OTHER INFORMATION: Synthetic primer

<400> SEQUENCE: 409
aaactttatt ccatctctct caatacaaa                                       29

<210> SEQ ID NO 410
<211> LENGTH: 21
<212> TYPE: DNA
<213> ORGANISM: Artificial Sequence
<220> FEATURE:
<223> OTHER INFORMATION: Synthetic primer

<400> SEQUENCE: 410
tttgtagaag tgtggtattg t                                               21

<210> SEQ ID NO 411
<211> LENGTH: 22
<212> TYPE: DNA
<213> ORGANISM: Artificial Sequence
<220> FEATURE:
<223> OTHER INFORMATION: Synthetic primer

<400> SEQUENCE: 411
aaactttatt ccatctctct ca                                              22

<210> SEQ ID NO 412
<211> LENGTH: 12
<212> TYPE: DNA
<213> ORGANISM: Artificial Sequence
<220> FEATURE:
<223> OTHER INFORMATION: Synthetic primer

<400> SEQUENCE: 412
atttgttgtt tt                                                         12

<210> SEQ ID NO 413
<211> LENGTH: 12
<212> TYPE: DNA
<213> ORGANISM: Artificial Sequence
<220> FEATURE:
<223> OTHER INFORMATION: Synthetic primer

<400> SEQUENCE: 413
attcgtcgtt tt                                                         12

<210> SEQ ID NO 414
<211> LENGTH: 26
<212> TYPE: DNA
<213> ORGANISM: Artificial Sequence
<220> FEATURE:
<223> OTHER INFORMATION: Synthetic primer

<400> SEQUENCE: 414
gtagaagtgt ggtattgtgg aataat                                          26

<210> SEQ ID NO 415
<211> LENGTH: 27
<212> TYPE: DNA
<213> ORGANISM: Artificial Sequence
<220> FEATURE:
<223> OTHER INFORMATION: Synthetic primer
```

<400> SEQUENCE: 415
aaactttatt ccatctctct caataca                                              27

<210> SEQ ID NO 416
<211> LENGTH: 19
<212> TYPE: DNA
<213> ORGANISM: Artificial Sequence
<220> FEATURE:
<223> OTHER INFORMATION: Synthetic primer

<400> SEQUENCE: 416
ttgtagaagt gtggtattg                                                       19

<210> SEQ ID NO 417
<211> LENGTH: 20
<212> TYPE: DNA
<213> ORGANISM: Artificial Sequence
<220> FEATURE:
<223> OTHER INFORMATION: Synthetic primer

<400> SEQUENCE: 417
aaactttatt ccatctctct                                                      20

<210> SEQ ID NO 418
<211> LENGTH: 330
<212> TYPE: DNA
<213> ORGANISM: Artificial Sequence
<220> FEATURE:
<223> OTHER INFORMATION: bisulfite-treated methylated human insulin gene

<400> SEQUENCE: 418
atgtgggggt gagtttaggg gttttaaggt agggtatttg gttttagtt tgttttagtt           60 ttgtttgttt tttagattat tgttttttg ttatggtttt gtggatgtgt ttttgtttt          120 tgttggtgtt gttggttttt tggggatttg atttagttgt agttttttgtg aattaatatt        180 tgtgtggttt atatttggtg gaagtttttt atttagtgtg tggggaatga gttttttttt         240
atatatttaa gatttgttgg gaggtagagg atttgtaggg tgagttaatt gtttattgtt         300
gtttttggtt gttttagtt attttttgtt                                           330

<210> SEQ ID NO 419
<211> LENGTH: 330
<212> TYPE: DNA
<213> ORGANISM: Artificial Sequence
<220> FEATURE:
<223> OTHER INFORMATION: bisulfite-treated un-methylated human insulin
      gene

<400> SEQUENCE: 419
atgtgggggt gagtttaggg gttttaaggt agggtatttg gttttagtt tgttttagtt          60 ttgtttgttt tttagattat tgttttttg ttatggtttt gtggatgcgt ttttgtttt          120 tgttggcgtt gttggttttt tggggatttg atttagtcgt agttttttgtg aattaatatt        180 tgtgcggttt atatttggtg gaagtttttt atttagtgtg cggggaacga gttttttttt         240
atatatttaa gattcgtcgg gaggtagagg atttgtaggg tgagttaatt gtttattgtt         300
gtttttggtc gttttagtt attttttgtt                                           330

<210> SEQ ID NO 420
<211> LENGTH: 14
<212> TYPE: DNA
<213> ORGANISM: Artificial Sequence

```
<220> FEATURE:
<223> OTHER INFORMATION: synthetic primer

<400> SEQUENCE: 420
tggttttggt agtt                                                        14

<210> SEQ ID NO 421
<211> LENGTH: 14
<212> TYPE: DNA
<213> ORGANISM: Artificial Sequence
<220> FEATURE:
<223> OTHER INFORMATION: synthetic primer

<400> SEQUENCE: 421
tggtttcggt agtt                                                        14

<210> SEQ ID NO 422
<211> LENGTH: 13
<212> TYPE: DNA
<213> ORGANISM: Artificial Sequence
<220> FEATURE:
<223> OTHER INFORMATION: synthetic primer

<400> SEQUENCE: 422
tttttttgaa ttg                                                         13

<210> SEQ ID NO 423
<211> LENGTH: 13
<212> TYPE: DNA
<213> ORGANISM: Artificial Sequence
<220> FEATURE:
<223> OTHER INFORMATION: synthetic primer

<400> SEQUENCE: 423 tttttcgaa ttg                                                          13

<210> SEQ ID NO 424
<211> LENGTH: 29
<212> TYPE: DNA
<213> ORGANISM: Artificial Sequence
<220> FEATURE:
<223> OTHER INFORMATION: synthetic primer

<400> SEQUENCE: 424
ggaggttgta taagaaattt attgtgttt                                        29

<210> SEQ ID NO 425
<211> LENGTH: 24
<212> TYPE: DNA
<213> ORGANISM: Artificial Sequence
<220> FEATURE:
<223> OTHER INFORMATION: synthetic primer

<400> SEQUENCE: 425
accaaccctc ctctactaaa taac                                             24

<210> SEQ ID NO 426
<211> LENGTH: 15
<212> TYPE: DNA
<213> ORGANISM: Artificial Sequence
<220> FEATURE:
<223> OTHER INFORMATION: synthetic primer

<400> SEQUENCE: 426
aatggtttga tatgt                                                       15
```

```
<210> SEQ ID NO 427
<211> LENGTH: 15
<212> TYPE: DNA
<213> ORGANISM: Artificial Sequence
<220> FEATURE:
<223> OTHER INFORMATION: synthetic primer

<400> SEQUENCE: 427
aatggttcga tatgt                                                          15

<210> SEQ ID NO 428
<211> LENGTH: 22
<212> TYPE: DNA
<213> ORGANISM: Artificial Sequence
<220> FEATURE:
<223> OTHER INFORMATION: synthetic primer

<400> SEQUENCE: 428
gatgagttat ttagtagagg ag                                                  22

<210> SEQ ID NO 429
<211> LENGTH: 18
<212> TYPE: DNA
<213> ORGANISM: Artificial Sequence
<220> FEATURE:
<223> OTHER INFORMATION: synthetic primer

<400> SEQUENCE: 429
actctaattc ccaccrtt                                                       18

<210> SEQ ID NO 430
<211> LENGTH: 15
<212> TYPE: DNA
<213> ORGANISM: Artificial Sequence
<220> FEATURE:
<223> OTHER INFORMATION: synthetic primer

<400> SEQUENCE: 430
ataaaaatgg tggga                                                          15

<210> SEQ ID NO 431
<211> LENGTH: 15
<212> TYPE: DNA
<213> ORGANISM: Artificial Sequence
<220> FEATURE:
<223> OTHER INFORMATION: synthetic primer

<400> SEQUENCE: 431
ataaaaacgg tggga                                                          15

<210> SEQ ID NO 432
<211> LENGTH: 22
<212> TYPE: DNA
<213> ORGANISM: Artificial Sequence
<220> FEATURE:
<223> OTHER INFORMATION: synthetic primer

<400> SEQUENCE: 432
atggttygat atgttataaa gg                                                  22

<210> SEQ ID NO 433
<211> LENGTH: 22
<212> TYPE: DNA
<213> ORGANISM: Artificial Sequence
<220> FEATURE:
<223> OTHER INFORMATION: synthetic primer
```

```
<400> SEQUENCE: 433
tataaacact ccattcctat aa                                            22

<210> SEQ ID NO 434
<211> LENGTH: 17
<212> TYPE: DNA
<213> ORGANISM: Artificial Sequence
<220> FEATURE:
<223> OTHER INFORMATION: synthetic primer

<400> SEQUENCE: 434
aggattattg agtttat                                                  17

<210> SEQ ID NO 435
<211> LENGTH: 17
<212> TYPE: DNA
<213> ORGANISM: Artificial Sequence
<220> FEATURE:
<223> OTHER INFORMATION: synthetic primer

<400> SEQUENCE: 435
aggattatcg agtttat                                                  17

<210> SEQ ID NO 436
<211> LENGTH: 21
<212> TYPE: DNA
<213> ORGANISM: Artificial Sequence
<220> FEATURE:
<223> OTHER INFORMATION: synthetic primer

<400> SEQUENCE: 436
tttataggaa tggagtgttt a                                             21

<210> SEQ ID NO 437
<211> LENGTH: 22
<212> TYPE: DNA
<213> ORGANISM: Artificial Sequence
<220> FEATURE:
<223> OTHER INFORMATION: synthetic primer

<400> SEQUENCE: 437
aaatctccaa cattaaacat aa                                            22
```

ASSAYS FOR DIAGNOSING TYPE 1 DIABETES

RELATED APPLICATIONS

This application is a continuation-in-part of U.S. application Ser. No. 14/490,333, filed Sep. 18, 2014, which claims the benefit of priority to U.S. Provisional Patent Application Ser. No. 61/879,347, filed Sep. 18, 2013; the contents of which are hereby incorporated by reference.

BACKGROUND OF THE INVENTION

Type 1 diabetes is caused by the destruction of pancreatic β cells due to an autoimmune process, which occurs over years. By the time clinical symptoms appear, the mass of β cells is reduced by at least 70-80% (Cnop, M. et al., (2005) *Diabetes Dec.;* 54 Suppl. 2:S97-107).

A nested PCR diagnostic for diabetes has been developed that detects the relative amount of circulating un-methylated β cell insulin DNA as a result of cell death (Akirav, E. M. et. al., (2011) *Proc. Natl. Acad. Sci.* 108: 19018-19023). However, nested PCR produces biases and artifacts.

Accordingly, new methods for diagnosing and monitoring type 1 diabetes are needed.

SUMMARY OF THE INVENTION

Featured herein are novel primers, probes and assays for diagnosing and monitoring type 1 diabetes.

One aspect of the invention provides probe composition consisting essentially of the nucleotide sequence set forth in SEQ ID NO: 422, 423, 426, 427, 430, 431, 434, or 435, or combination thereof.

In some embodiments, the probe composition also includes at least one quencher probe.

In some embodiments, the quencher probe of the probe composition is selected from the group consisting of: fluorescein amidite, Iowa Black FQ quencher, and hexachlorofluorescein.

Another aspect of the invention provides a probe pair consisting essentially of the nucleotide sequence set forth in SEQ ID NOs: 422 and 423, SEQ ID NOs: 426 and 427, SEQ ID NOs: 430 and 431, or SEQ ID NOs: 434 and 435, or combination thereof.

In some embodiments, the probe pair further comprises at least one quencher probe.

In some embodiments, the quencher probe of the probe pair is selected from the group consisting of: fluorescein amidite, Iowa Black FQ quencher, and hexachloro-fluorescein.

Another aspect of the invention provides a primer pair consisting essentially of the nucleotide sequence set forth in SEQ ID NOs: 424 and 425, SEQ ID NOs: 428 and 429, SEQ ID NOs: 432 and 433, or SEQ ID NOs: 436 and 437, or combination thereof.

In some embodiments, the primer pair further comprises a chemical modification or change, label, tag, or reagent.

Another aspect of the invention relates to a method of diagnosing whether a subject has or is at risk of developing type 1 diabetes comprising the steps of:
(a) isolating genomic islet-specific glucose-6-phosphatase catalytic subunit-related (IGRP) DNA from an appropriate sample obtained from a subject and treating the isolated DNA with bisulfite;
(b) contacting the DNA with an appropriate amount of a composition comprising a combination probe pair and primer pair containing nucleotide sequences indicative of the methylation status of said DNA to form a reaction mixture;
(c) loading the reaction mixture into a droplet generator;
(d) depositing the droplets generated onto a plate and transferring the plate into a polymerase chain reactor for amplification;
(e) transferring the plate into a droplet reader for analysis of the data, wherein the ratio of detected unmethylated IGRP or insulin DNA copy number to a reference DNA copy number indicates that the subject has or is at risk of developing type 1 diabetes.

In certain embodiments of the methods, the combination probe pair comprises an unmethylated probe and a methylated probe.

In certain embodiments of the methods, the unmethylated probe is selected from the group consisting of the nucleotide sequence set forth in SEQ ID NO: 422, 426, 430, and 434, or combination thereof.

In certain embodiments of the methods, the methylated probe is selected from the group consisting of the nucleotide sequence set forth in SEQ ID NO: 423, 427, 431, and 435, or combination thereof.

In certain embodiments of the methods, the probe is selected from the group consisting of the nucleotide sequence set forth in SEQ ID NO: 422, 423, 426, 427, 430, 431, 434, and 435, or combination thereof.

In certain embodiments of the methods, the primer is selected from the group consisting of the nucleotide sequences set forth in SEQ ID NO: 424, 425, 428, 429, 432, 433, 436, and 437, or combination thereof.

In certain embodiments of the methods, the probe pair is selected from the group consisting of SEQ ID NOs: 422 and 423, SEQ ID NOs: 426 and 427, SEQ ID NOs: 430 and SEQ ID NOs: 431, and 434 and 435.

In certain embodiments of the methods, the primer pair is selected from the group consisting of SEQ ID NOs: 424 and 425, SEQ ID NOs: 428 and 429, SEQ ID NOs: 432 and 433, and SEQ ID NOs: 436 and 437.

In certain embodiments of the methods, the combination probe pair and primer pair is selected from the group consisting of SEQ ID NOs: 422-425; SEQ ID NOs: 426-429; SEQ ID NOs: 430-433; and SEQ ID NOs: 434-437.

In certain embodiments of the methods, the combination probe pair and primer pair is SEQ ID NOs: 422-425.

In certain embodiments of the methods, the combination probe pair and primer pair is SEQ ID NOs: 426-429.

In certain embodiments of the methods, the combination probe pair and primer pair is SEQ ID NOs: 430-433.

In certain embodiments of the methods, the combination probe pair and primer pair is SEQ ID NOs: 434-437.

In certain embodiments of the methods, the subject has received or is receiving anti-cancer or chemotherapy, has undergone or is undergoing anti-cancer or chemotherapy, or is suffering from cancer.

In certain embodiments of the methods, the subject is a mammal.

In certain embodiments of the methods, the subject is human.

In certain embodiments of the methods, the reference DNA of step (e) is total IGRP or insulin DNA, methylated IGRP or insulin DNA, or total DNA from any other gene or genes.

In certain embodiments, reference gene in step (e) of any of the aforementioned methods is any gene that can be used to monitor how much DNA is present in serum from a given patient at that time. In certain embodiments, one would use the gene that is being probed for in the beta cell death assay. Examples of reference gene includes, but not limited to, glyceraldehyde 3-phosphate dehydrogenase (GAPDH), ACTIN, or hypoxanthine-guanine phosphoribosyltransferase (HPRT). Other housekeeping genes are contemplated.

The assays are highly sensitive and may be performed in a multiplexed fashion to diagnose diabetes before the onset of clinical symptoms and provide clinicians with a tool to decide for whom and when immune therapy might be useful.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Figure 1:
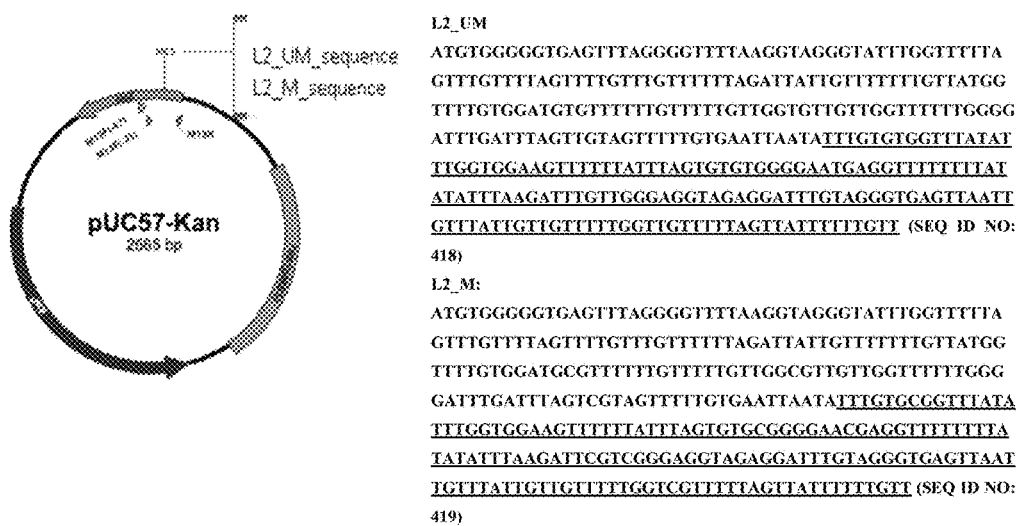
FIG. 1 depicts the cloning of L2_UM DNA (SEQ ID NO: 418) and L2_M DNA (SEQ ID NO: 419) into the pUC57 plasmid. The underlined sequences highlight the regions of primers and probes.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION OF THE INVENTION

Described herein are specific primers and probes, which can be used to measure the relative amounts of methylated and un-methylated insulin DNA in serum obtained from a human subject. The un-methylated form of the gene expresses functional insulin, while the methylated form does not express protein. Since β cells are the only significant source of insulin gene expression, the assay is able to measure epigenetically circulating un-methylated insulin DNA as a marker for β cell death. Methylated insulin DNA is used for normalizing the varying levels of DNA between individual specimens.

TABLE 1

List of primers and probes

| | |
|---|---|
| L2_KH1_FWD4 | GTGGTTTATATTTGGTGGA (SEQ ID NO. 5) |
| L2_KH1_REV4 | ATTAACTCACCCTACAAATC (SEQ ID NO. 6) |

The nucleotide sequence of the unmethylated insulin DNA detection probe is: ATTTAAGATTTGTTGGGAGGTAGAG (SEQ ID NO: 1) and the nucleotide sequence of the methylated insulin DNA detection probe is: ATTTAAGATTCGTCGGGAGGTAGAG (SEQ ID NO: 2). One of skill in the art could alter the probes by deleting, replacing of altering one or more nucleotides without substantially changing probe function.

The probes target a region of the human insulin gene with 2 CpG sites (i.e., regions of DNA where a cytosine nucleotide occurs next to a guanine nucleotide). When DNA is treated with bisulfite, the un-methylated CpG is converted to TG (thymine, guanine), while a methylated CpG site is protected from this change. The two probes described herein target either a methylated or un-methylated insulin gene.

Also described are double quencher probes specific for un-methylated human insulin gene DNA detection with fluorescein amidite (FAM): L2_KH 1_UM 5'-/56-FAM/ATTTAAGAT/ZEN/TTGTTGGGAGGTAGAG/3IAB-kFQ/-3' (SEQ ID NO: 178) and for methylated human insulin gene detection with hexachloro-fluoroscein (HEX): L2_KH1_M 5'-/5HEX/ATTTAAGAT/ZEN/TCGTCGGGAGGTAGAG/3IABkFQ/-3' (SEQ ID NO: 179).

Use of these probes significantly reduces the background noise thereby increasing the noise to signal ratio.

The forward and reverse human insulin gene primers used in the examples are GTGGTTTATATTTGGTGGA (SEQ ID NO: 5) and ATTAACTCACCCTACAAATC (SEQ ID NO: 6). However, one of skill in the art may vary these sequences, e.g., by deleting, substituting or altering certain nucleotides without substantially impacting primer function.

Also provided herein are specific primers and probes, which can be used to measure the relative amounts of methylated and un-methylated islet specific glucose-6-phosphatase catalytic subunit-related proteins (IGRP) DNA in serum obtained from a human subject. IGRP is solely expressed in beta cells. Gene expression is controlled by methylation of CpGs. Therefore, the methylation pattern of the IGRP gene is unique to beta cells, which can serve as a biomarker for beta cell death.

Such human patients may be selected from patients with recent onset T1D (up to 1 year after diagnosis) or at high risk of diabetes. High risk of diabetes patients do not have diabetes but are relatives of patients with T1D and have at least one or more autoantibody. Other patients may be those who have received or is receiving anti-cancer or chemotherapy, has undergone or is undergoing anti-cancer or chemotherapy, or is suffering from cancer.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, Langerhans cell histiocytosis, laryngeal cancer, leukemia, lung cancer, non-small cell lung cancer, small cell lung cancer, Hodgkin lymphoma, lymphoma, medulloblastoma, medulloepithelioma, melanoma, mesothelioma, mouth cancer, multiple myeloma, nasopharyngeal cancer, neuroblastoma, non-Hodgkin lymphoma, oral cancer, oropharyngeal cancer, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm, pleuropulmonary blastoma, primary central nervous system lymphoma, prostate cancer, rectal cancer, renal cell (kidney) cancer, rhabdomyosarcoma, salivary gland cancer, sarcoma, Ewing sarcoma family of tumors, sarcoma, Sezary syndrome, skin cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, or Wilms tumor.

Anti-cancer therapy may include treatment with anti-PD-1, anti-PD-L1, nivolumab, 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, carboplatin, carmustine, CB1093, chlorambucil, cisplatin, crisnatol, cyclophosphamide, cytarabine, cytosine arabinoside, cytoxan, dacarbazine, dactinomycin, daunorubicin, decarbazine, deferoxamine, demethoxy-hypocrellin A, docetaxel, doxifluridine, doxorubicin, EB1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, or zorubicin.

Chemotherapy may include treatment with small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenypamino]-6-{[4-(N,N-dimethylamino)-1-oxo-2-bute-n-1-yl]amino}-7-((S)-tetrahydrofuran-3-yloxy)quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, The probes and primers described herein are chemically modified. For example, the primers and probes may be linked to a water soluble polymers, labels, and reagents to facilitate detection, solubility, affinity, binding, annealing temperature, and specificity, or to decrease aggregation, background signal, and the like. The polymer may have a single reactive group, such as an active ester for acylation or an aldehyde for alkylation, so that the degree of polymerization may be controlled. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. The reagent may be selected from the group consisting of biotin and avidin, carbohydrates and lectins, complementary nucleotide sequences, complementary peptide sequences, effector and receptor molecules, enzyme cofactors and enzymes, and enzyme inhibitors and enzymes.

The probes and primers may be altered so as to have certain "sequence identity or homology" to any of the sequences described herein. "Sequence identity or homology" refers to the sequence similarity between two nucleic acid sequences. When a position in both of the two compared sequences is occupied by the same base, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. Generally, a comparison is made when two sequences are aligned to give maximum homology. Exemplary levels of sequence identity include, but are not limited to, 80, 81, 82, 83, 84, 85, 86, 87, 88, 89, 90, 91, 92, 93, 94, 95, 96, 97, 98, 99% or more sequence identity to a given sequence (e.g., any of SEQ ID NOs: 1-437).

The probes and primers described herein may be contacted with isolated and bisulfite-treated genomic DNA from an appropriate sample (e.g. serum, islet cells or peripheral blood mononuclear cells (PBMCs)). The reaction mixture may be loaded into a droplet generator. The droplets may be deposited on a plate and transferred into a polymerase chain reactor for amplification. The plate may then be transferred to a droplet reader for analysis of the data.

Use of the described probes and primers in a sensitive diagnostic assay, such as Droplet Digital Polymerase Chain Reaction (ddPCR), results in a highly specific and sensitive assay. In particular, as shown in the following examples, fewer than 13 copies were detected in a 25 µl PCR reaction with the target gene. In addition, in a recovery assay, where 5000 copies of L2_M plasmid representing bisulfite-treated methylated human insulin gene DNA were spiked with fewer than 10 copies of L2_UM plasmid representing bisulfite-treated un-methylated target DNA, L2_UM DNA was successfully detected.

As the results reported in the following example show, use of the described probes, primers and assays can be used to determine insulin DNA methylation status at low concentrations of DNA.

These primers and probes alone or in conjunction with instructions for use may be prepared as a kit for diagnosing or monitoring type 1 diabetes.

Table 2 lists additional probes and primers for amplification of methylation sensitive sites. Each assay has one set of probes, which can be used with 1 to 7 different sets of primers. Some probes will require modifications to the probes themselves to increase the annealing temperature and specificity such as—minor groove binder (MGB) modification, locked nucleic acid modification (LNA) and or Zen modification.

TABLE 2

List of Probes and Primers

| 5'-3' | Type (5'-3') | Sequence1 | Amplicon |
|---|---|---|---|
| | Probe-Unmeth | AGAGTTTTGTTTTGTA (SEQ ID NO: 7) | |
| | Probe_meth | AGAGTTTCGTTTTGTA (SEQ ID NO: 8) | |
| Primer Pair 1 | Forward Primer | GGGATAGTAGTGTAA (SEQ ID NO: 9) | |
| Primer Pair 1 | Reverse Primer | CCTACTCACAACTAA (SEQ ID NO: 10) | |
| | Product | | 118 |
| | Type | Sequence5 | Amplicon |
| | Probe-Unmeth | TGGTTATTGGGTTTT (SEQ ID NO: 11) | |
| | Probe_meth | TGGTTATCGGGTTTT (SEQ ID NO: 12) | |
| Primer Pair 1 | Forward Primer | GGAAAGTGGTTTAGGTGAGGGTTT (SEQ ID NO: 13) | |
| Primer Pair 1 | Reverse Primer | CTCCTTAATCATCAACACCTCTTCCTC (SEQ ID NO: 14) | |
| | Product | | 142 |
| Primer Pair 2 | Forward Primer | TAGTTGTGAGTAGGGATAGGTT (SEQ ID NO: 15) | |
| Primer Pair 2 | Reverse Primer | AATCTCCTTAATCATCAACACCT (SEQ ID NO: 16) | |
| | Product | | 97 |
| Primer Pair 3 | Forward Primer | GGTTTAATGTGGAAAGTGGTTTAG (SEQ ID NO: 17) | |
| Primer Pair 3 | Reverse Primer | AACCATTTCCCTAATACTAAATCTATAA (SEQ ID NO: 18) | |
| | Product | | 186 |
| Primer Pair 4 | Forward Primer | TTTGGTTTAATGTGGAAAGT (SEQ ID NO: 19) | |
| Primer Pair 4 | Reverse Primer | CCAAACCATTTCCCTAATAC (SEQ ID NO: 20) | |
| | Product | | 192 |
| Primer Pair 5 | Forward Primer | GGGATAGTAGTGTAAAGAGTT (SEQ ID NO: 21) | |
| Primer Pair 5 | Reverse Primer | ACTACAATTTCCAAACCATTTC (SEQ ID NO: 22) | |
| | Product | | 245 |
| | Type | Sequence6 | Amplicon |
| | Probe-Unmeth | TTAATGATTTGTTGGTTTTGA (SEQ ID NO: 23) | |
| | Probe_meth | TTAATGATTCGTTGGTTTTGA (SEQ ID NO: 24) | |
| Primer Pair 1 | Forward Primer | GGAAAGTGGTTTAGGTGAGGGTTT (SEQ ID NO: 25) | |
| Primer Pair 1 | Reverse Primer | ATCTCCTTAATCATCAACACCTCTTCC (SEQ ID NO: 26) | |
| | Product | | 144 |
| Primer Pair 2 | Forward Primer | GTGAGTAGGGATAGGTTTGGTTAT (SEQ ID NO: 27) | |
| Primer Pair 2 | Reverse Primer | CCCTACCACCTAACCCATTAAA (SEQ ID NO: 28) | |
| | Product | | 197 |
| Primer Pair 3 | Forward Primer | GGATAGGTTTGGTTATTGGGTTT (SEQ ID NO: 29) | |
| Primer Pair 3 | Reverse Primer | TCCAAACCATTTCCCTAATACTAAAT (SEQ ID NO: 30) | |
| | Product | | 119 |
| Primer Pair 4 | Forward Primer | TAGTTGTGAGTAGGGATAGGT (SEQ ID NO: 31) | |
| Primer Pair 4 | Reverse Primer | AAACTACAATTTCCAAACCATTTC (SEQ ID NO: 32) | |
| | Product | | 143 |
| Primer Pair 5 | Forward Primer | TTTAATGTGGAAAGTGGTTTAG (SEQ ID NO: 33) | |
| Primer Pair 5 | Reverse Primer | AAATCTCCTTAATCATCAACAC (SEQ ID NO: 34) | |
| | Product | | 154 |

TABLE 2-continued

List of Probes and Primers

| | Type | Sequence7 | Amplicon |
|---|---|---|---|
| | Probe-Unmeth | AAGAGGTGTTGATGATTAAGGAGAT (SEQ ID NO: 35) | |
| | Probe_meth | AAGAGGTGTTGACGATTAAGGAGAT (SEQ ID NO: 36) | |
| Primer Pair 1 | Forward Primer | GTGAGTAGGGATAGGTTTGGTTAT (SEQ ID NO: 37) | |
| Primer Pair 1 | Reverse Primer | CCCTACCACCTAACCCATTAAA (SEQ ID NO: 38) | |
| | Product | | 197 |
| Primer Pair 2 | Forward Primer | GAAAGTGGTTTAGGTGAGGGTT (SEQ ID NO: 39) | |
| Primer Pair 2 | Reverse Primer | TCCAAACCATTTCCCTAATACTAAATCT (SEQ ID NO: 40) | |
| | Product | | 179 |
| Primer Pair 3 | Forward Primer | TAGTTGTGAGTAGGGATAGGT (SEQ ID NO: 41) | |
| Primer Pair 3 | Reverse Primer | AAACTACAATTTCCAAACCATTTC (SEQ ID NO: 42) | |
| | Product | | 143 |
| Primer Pair 4 | Forward Primer | GATAGGTTTGGTTATTGGGTTT (SEQ ID NO: 43) | |
| Primer Pair 4 | Reverse Primer | ATTTCCAAACCATTTCCCTAATA (SEQ ID NO: 44) | |
| | Product | | 121 |
| Primer Pair 5 | Forward Primer | TTTAATGATTTGTTGGTTT (SEQ ID NO: 45) | |
| Primer Pair 5 | Reverse Primer | CCCACTAACTTTATAATCTC (SEQ ID NO: 46) | |
| | Product | | 201 |

| | Type | Sequence8 | Amplicon |
|---|---|---|---|
| | Probe-Unmeth | AAATGGTTTGGAAATTGTA (SEQ ID NO: 47) | |
| | Probe_meth | AAATGGTTCGGAAATTGTA (SEQ ID NO: 48) | |
| Primer Pair 1 | Forward Primer | TGAGGAAGAGGTGTTGATGATT (SEQ ID NO: 49) | |
| Primer Pair 1 | Reverse Primer | CCCTACCACCTAACCCATTAAA (SEQ ID NO: 50) | |
| | Product | | 136 |
| Primer Pair 2 | Forward Primer | AGAGGTGTTGATGATTAAGGAGATT (SEQ ID NO: 51) | |
| Primer Pair 2 | Reverse Primer | ACCTCTTCTAATACAACCTATCCTAAA (SEQ ID NO: 52) | |
| | Product | | 223 |
| Primer Pair 3 | Forward Primer | AGTTGTGAGTAGGGATAGG (SEQ ID NO: 53) | |
| Primer Pair 3 | Reverse Primer | CCCACTAACTTTATAATCTCAAA (SEQ ID NO: 54) | |
| | Product | | 247 |
| Primer Pair 4 | Forward Primer | TTTGAGGAAGAGGTGTT (SEQ ID NO: 55) | |
| Primer Pair 4 | Reverse Primer | ACCTCTTCTAATACAACCTA (SEQ ID NO: 56) | |
| | Product | | 231 |
| Primer Pair 5 | Forward Primer | TTTATAGATTTAGTATTAGGG (SEQ ID NO: 57) | |
| Primer Pair 5 | Reverse Primer | CTACTTAATAACCTCTTCT (SEQ ID NO: 58) | |
| | Product | | 206 |

| | Type | Sequence9 | Amplicon |
|---|---|---|---|
| | Probe-Unmeth | TTAGGTGGTAGGG (SEQ ID NO: 59) | |
| | Probe_meth | TTAGGTGGTAGGG (SEQ ID NO: 60) | |
| Primer Pair 1 | Reverse Primer | AATAACCTCTTCTAATACAACCTATCCT (SEQ ID NO: 61) | |
| Primer Pair 1 | Product | | 183 |
| | Forward Primer | AGTATTAGGGAAATGGTTTGGA (SEQ ID NO: 62) | |
| Primer Pair 2 | Reverse Primer | CAAACCTACTTAATAACCTCTTCTAAT (SEQ ID NO: 63) | |
| Primer Pair 2 | Product | | 200 |
| | Forward Primer | GAGGAAGAGGTGTTGATG (SEQ ID NO: 64) | |
| Primer Pair 3 | Reverse Primer | CCCACTAACTTTATAATCTCAAA (SEQ ID NO: 65) | |
| Primer Pair 3 | Product | | 181 |
| | Forward Primer | TTTAGTATTAGGGAAATG (SEQ ID NO: 66) | |
| Primer Pair 4 | Reverse Primer | ACCTACTTAATAACCTC (SEQ ID NO: 67) | |
| Primer Pair 4 | Product | | 200 |

| | Type | Sequence10 | Amplicon |
|---|---|---|---|
| | Probe-Unmeth | AAGTTAGTGGGGGTTT (SEQ ID NO: 68) | |
| | Probe_meth | AAGTTAGCGGGGTTT (SEQ ID NO: 69) | |
| Primer Pair 1 | Forward Primer | TTTAATGGGTTAGGTGGTAGGG (SEQ ID NO: 70) | |
| Primer Pair 1 | Reverse Primer | ACCTCTTCTAATACAACCTATCCTAAA (SEQ ID NO: 71) | |
| | Product | | 115 |
| Primer Pair 2 | Forward Primer | GGGAAATGGTTTGGAAATTGTAGTT (SEQ ID NO: 72) | |
| Primer Pair 2 | Reverse Primer | ACCTACTTAATAACCTCTTCTAATACAACC (SEQ ID NO: 73) | |
| | Product | | 190 |

TABLE 2-continued

List of Probes and Primers

| | | | |
|---|---|---|---|
| Primer Pair 3 | Forward Primer | GTATTAGGGAAATGGTTTGGAAAT (SEQ ID NO: 74) | |
| Primer Pair 3 | Reverse Primer | ACAAACCTACTTAATAACCTCTTCTA (SEQ ID NO: 75) | |
| | Product | | 200 |
| Primer Pair 4 | Forward Primer | AGTATTAGGGAAATGGT (SEQ ID NO: 76) | |
| Primer Pair 4 | Reverse Primer | CAAACCTACTTAATAACC (SEQ ID NO: 77) | |
| | Product | | 200 |
| | Type | Sequence12 | Amplicon |
| | Probe-Unmeth | TTTGTCTTAGGT (SEQ ID NO: 78) | |
| | Probe_meth | TTTGCGTTAGGT (SEQ ID NO: 79) | |
| Primer Pair 1 | Forward Primer | GGTTGTATTAGAAGAGGTTATTAAGTAGGT (SEQ ID NO: 80) | |
| Primer Pair 1 | Reverse Primer | CTTCACAAACCCAACCACATCC (SEQ ID NO: 81) | |
| | Product | | 131 |
| Primer Pair 2 | Forward Primer | TTAGGATAGGTTGTATTAGAAGAGGTTATT (SEQ ID NO: 82) | |
| Primer Pair 2 | Reverse Primer | CCAACCACATCCTCCCTACT (SEQ ID NO: 83) | |
| | Product | | 129 |
| Primer Pair 3 | Forward Primer | TAATGGGTTAGGTGGTAGGG (SEQ ID NO: 84) | |
| Primer Pair 3 | Reverse Primer | CCCACATACTTCACAAACC (SEQ ID NO: 85) | |
| | Product | | 234 |
| Primer Pair 4 | Forward Primer | AGGATAGGTTGTATTAGAAGA (SEQ ID NO: 86) | |
| Primer Pair 4 | Reverse Primer | AAATCCAACCACCCTAAA (SEQ ID NO: 87) | |
| | Product | | 91 |
| Primer Pair 5 | Forward Primer | TTGAGATTATAAAGTTAGTGG (SEQ ID NO: 88) | |
| Primer Pair 5 | Reverse Primer | AAACCAAATACCCTACC (SEQ ID NO: 89) | |
| | Product | | 227 |
| | Type | Sequence13 | Amplicon |
| | Probe-Unmeth | TAGGGAGGATGTGGTTGGGT (SEQ ID NO: 90) | |
| | Probe_meth | TAGGGAGGACGTGGTTGGGT (SEQ ID NO: 91) | |
| Primer Pair 1 | Forward Primer | GTGTTAGGTGGGTTTAGGA (SEQ ID NO: 92) | |
| Primer Pair 1 | Reverse Primer | AAACCAACAACACCAACAA (SEQ ID NO: 93) | |
| | Product | | 223 |
| Primer Pair 2 | Forward Primer | AGGATAGGTTGTATTAGAAGAGG (SEQ ID NO: 94) | |
| Primer Pair 2 | Reverse Primer | AAACCAAATACCCTACCTTAAA (SEQ ID NO: 95) | |
| | Product | | 182 |
| Primer Pair 3 | Forward Primer | TTAGGGTGGTTGGATTT (SEQ ID NO: 96) | |
| Primer Pair 3 | Reverse Primer | CACACAAATATTAATTCACAAA (SEQ ID NO: 97) | |
| | Product | | 250 |
| | Type | Sequence14 | Amplicon |
| | Probe-Unmeth | TTGTTGGTGTTGTTGG (SEQ ID NO: 98) | |
| | Probe_meth | TTGTTGGCGTTGTTGG (SEQ ID NO: 99) | |
| Primer Pair 1 | Forward Primer | GAGGATGTGGTTGGGTTTGTGA (SEQ ID NO: 100) | |
| Primer Pair 1 | Reverse Primer | AACTTCCACCAAATATAAACCACACAAATA (SEQ ID NO: 101) | |
| | Product | | 231 |
| Primer Pair 2 | Forward Primer | GGTTGGGTTTGTGAAGTATGTG (SEQ ID NO: 102) | |
| Primer Pair 2 | Reverse Primer | ACCAAATATAAACCACACAAATATTAATTC (SEQ ID NO: 103) | |
| | Product | | 216 |
| Primer Pair 3 | Forward Primer | TTGTAGTAGGGAGGATGTGG (SEQ ID NO: 104) | |
| Primer Pair 3 | Reverse Primer | AAACTTCCACCAAATATAAACCA (SEQ ID NO: 105) | |
| | Product | | 242 |
| Primer Pair 4 | Forward Primer | TTTAAGGTAGGGTATTTGGTTT (SEQ ID NO: 106) | |
| Primer Pair 4 | Reverse Primer | CCTCTACCTCCCAACAAATC (SEQ ID NO: 107) | |
| | Product | | 248 |
| Primer Pair 5 | Forward Primer | GTGTTAGGTGGGTTTAGGA (SEQ ID NO: 108) | |
| Primer Pair 5 | Reverse Primer | AAACTACAACTAAATCAAATCCC (SEQ ID NO: 109) | |
| | Product | | 250 |
| Primer Pair 6 | Forward Primer | TTTAAGGTAGGGTATTTGGTTT (SEQ ID NO: 110) | |
| Primer Pair 6 | Reverse Primer | ACCACACAAATATTAATTCACAAA (SEQ ID NO: 111) | |
| | Product | | 166 |

TABLE 2-continued

List of Probes and Primers

| | | | |
|---|---|---|---|
| Primer Pair 7 | Forward Primer | TTGTAGTAGGGAGGATGTGG (SEQ ID NO: 112) | |
| Primer Pair 7 | Reverse Primer | AAACTACAACTAAATCAAATCCC (SEQ ID NO: 113) | |
| | Product | | 200 |

| | Type | Sequence15 | Amplicon |
|---|---|---|---|
| | Probe-Unmeth | TTAGTTGTAGTT (SEQ ID NO: 114) | |
| | Probe_meth | TTAGTCGTAGTT (SEQ ID NO: 115) | |
| Primer Pair 1 | Forward Primer | GGTTGGGTTTGTGAAGTATGTG (SEQ ID NO: 116) | |
| Primer Pair 1 | Reverse Primer | ACCAAATATAAACCACACAAATATTAATTC (SEQ ID NO: 117) | |
| | Product | | 216 |
| Primer Pair 2 | Forward Primer | TTGTAGTAGGGAGGATGTGG (SEQ ID NO: 118) | |
| Primer Pair 2 | Reverse Primer | AAACTTCCACCAAATATAAACCA (SEQ ID NO: 119) | |
| | Product | | 242 |
| Primer Pair 3 | Forward Primer | TTTGTTGGTGTTGTTGGTTT (SEQ ID NO: 120) | |
| Primer Pair 3 | Reverse Primer | CCTCTACCTCCCAACAAATC (SEQ ID NO: 121) | |
| | Product | | 152 |
| Primer Pair 4 | Forward Primer | TTTAAGGTAGGGTATTTGGTTT (SEQ ID NO: 122) | |
| Primer Pair 4 | Reverse Primer | ACCACACAAATATTAATTCACAAA (SEQ ID NO: 123) | |
| | Product | | 166 |

| | Type | Sequence16 | Amplicon |
|---|---|---|---|
| | Probe-Unmeth | TTGTGTGGTTTA (SEQ ID NO: 124) | |
| | Probe_meth | TTGTGCGGTTTA (SEQ ID NO: 125) | |
| Primer Pair 1 | Forward Primer | TTTGTTGGTGTTGTTGGTTT (SEQ ID NO: 126) | |
| Primer Pair 1 | Reverse Primer | CCTCTACCTCCCAACAAATC (SEQ ID NO: 127) | |
| | Product | | 152 |
| Primer Pair 2 | Forward Primer | GGGATTTGATTTAGTTGTAGTTT (SEQ ID NO: 128) | |
| Primer Pair 2 | Reverse Primer | CTCACCCTACAAATCCTCTAC (SEQ ID NO: 129) | |
| | Product | | 142 |
| Primer Pair 3 | Forward Primer | TTTAAGGTAGGGTATTTGGTT (SEQ ID NO: 130) | |
| Primer Pair 3 | Reverse Primer | ACCTCCCAACAAATCTTAAATA (SEQ ID NO: 131) | |
| | Product | | 243 |
| Primer Pair 4 | Forward Primer | GTTGGGTTTGTGAAGTA (SEQ ID NO: 132) | |
| Primer Pair 4 | Reverse Primer | CCCACACACTAAATAAA (SEQ ID NO: 133) | |
| | Product | | 240 |

| | Type | Sequence17 | Amplicon |
|---|---|---|---|
| | Probe-Unmeth | AGTGTGTGGGGAA (SEQ ID NO: 134) | |
| | Probe_meth | AGTGTGCGGGGAA (SEQ ID NO: 135) | |
| Primer Pair 1 | Forward Primer | ATTTGTGTGGTTTATATTTGGTGGAAGT (SEQ ID NO: 136) | |
| Primer Pair 1 | Reverse Primer | ACTCACCCTACAAATCCTCTACCT (SEQ ID NO: 137) | |
| | Product | | 108 |
| Primer Pair 2 | Forward Primer | TTGTGAATTAATATTTGTGTGGTTTATATT (SEQ ID NO: 138) | |
| Primer Pair 2 | Reverse Primer | TCCTCTACCTCCCAACAAATC (SEQ ID NO: 139) | |
| | Product | | 106 |
| Primer Pair 3 | Forward Primer | TTTGTTGGTGTTGTTGGTTT (SEQ ID NO: 140) | |
| Primer Pair 3 | Reverse Primer | TCTACCTCCCAACAAATCTTAAATA (SEQ ID NO: 141) | |
| | Product | | 150 |
| Primer Pair 4 | Forward Primer | TTTGTGAATTAATATTTGTGTGGT (SEQ ID NO: 142) | |
| Primer Pair 4 | Reverse Primer | CAATAAACAATTAACTCACCCTAC (SEQ ID NO: 143) | |
| | Product | | 134 |
| Primer Pair 5 | Forward Primer | GGGATTTGATTTAGTTGTAGTTT (SEQ ID NO: 144) | |
| Primer Pair 5 | Reverse Primer | CTAAATAACAACCTCCTACCC (SEQ ID NO: 145) | |
| | Product | | 240 |

| | Type | Sequence18 | Amplicon |
|---|---|---|---|
| | Probe-Unmeth | AGATTTGTTGGGAG (SEQ ID NO: 146) | |
| | Probe_meth | AGATTCGTCCGGAG (SEQ ID NO: 147) | |
| Primer Pair 1 | Forward Primer | ATTTGTGTGGTTTATATTTGGTGGAAGT (SEQ ID NO: 148) | |
| Primer Pair 1 | Reverse Primer | ACAATTAACTCACCCTACAAATCCTCTAC (SEQ ID NO: 149) | |
| | Product | | 115 |

TABLE 2-continued

List of Probes and Primers

| | | | |
|---|---|---|---|
| Primer Pair 2 | Forward Primer | TGAATTAATATTTGTGTGGTTTATATTTGG (SEQ ID NO: 150) | |
| Primer Pair 2 | Reverse Primer | ACAATAAACAATTAACTCACCCTACA (SEQ ID NO: 151) | |
| | Product | | 131 |
| Primer Pair 3 | Forward Primer | TTTGTGAATTAATATTTGTGTGGTTTA (SEQ ID NO: 152) | |
| Primer Pair 3 | Reverse Primer | CCTACTAAATAACAACCTCCTACC (SEQ ID NO: 153) | |
| | Product | | 222 |
| Primer Pair 4 | Forward Primer | TGTTGGTGTTGTTGGTTT (SEQ ID NO: 154) | |
| Primer Pair 4 | Reverse Primer | CCCTTCTACCCATACTAAATAAA (SEQ ID NO: 155) | |
| | Product | | 242 |
| Primer Pair 5 | Forward Primer | TTTGTGAATTAATATTTGTG (SEQ ID NO: 156) | |
| Primer Pair 5 | Reverse Primer | CCCTACTAAATAACAACC (SEQ ID NO: 157) | |
| | Product | | 223 |

| | Type | Sequence20 | Amplicon |
|---|---|---|---|
| | Probe-Unmeth | TTGGTTGTTTTT (SEQ ID NO: 158) | |
| | Probe_meth | TTGGTCGTTTTT (SEQ ID NO: 159) | |
| Primer Pair 1 | Forward Primer | GGTAGAGGATTTGTAGGGTGAGTTAAT (SEQ ID NO: 160) | |
| Primer Pair 1 | Reverse Primer | CCCTACTAAATAACAACCTCCTACCC (SEQ ID NO: 161) | |
| | Product | | 125 |
| Primer Pair 2 | Forward Primer | TTGTTGGGAGGTAGAGGATTTGTA (SEQ ID NO: 162) | |
| Primer Pair 2 | Reverse Primer | AAACCAACACCATCCTCAAACTAAA (SEQ ID NO: 163) | |
| | Product | | 238 |
| Primer Pair 3 | Forward Primer | AGGGTGAGTTAATTGTTTATTGTTGTTT (SEQ ID NO: 164) | |
| Primer Pair 3 | Reverse Primer | ACATACCCACCCTCTAATATATCTCAA (SEQ ID NO: 165) | |
| | Product | | 250 |
| Primer Pair 4 | Forward Primer | TAAGATTTGTTGGGAGGTAGAG (SEQ ID NO: 166) | |
| Primer Pair 4 | Reverse Primer | CCCTTCTACCCATACTAAATAAA (SEQ ID NO: 167) | |
| | Product | | 115 |
| Primer Pair 5 | Forward Primer | GTAGGGTGAGTTAATTGTTTATT (SEQ ID NO: 168) | |
| Primer Pair 5 | Reverse Primer | AACCAACACCATCCTCA (SEQ ID NO: 169) | |
| | Product | | 216 |

| | Type | Sequence21 | Amplicon |
|---|---|---|---|
| | Probe-Unmeth | TTTGGTGTTTTT (SEQ ID NO: 170) | |
| | Probe_meth | TTTGGCGTTTTT (SEQ ID NO: 171) | |
| Primer Pair 1 | Forward Primer | GGTAGAGGATTTGTAGGGTGAGTTAAT (SEQ ID NO: 172) | |
| Primer Pair 1 | Reverse Primer | CCCTACTAAATAACAACCTCCTACCC (SEQ ID NO: 173) | |
| | Product | | 125 |
| Primer Pair 2 | Forward Primer | TTGTTGGGAGGTAGAGGATTTGTA (SEQ ID NO: 174) | |
| Primer Pair 2 | Reverse Primer | AAACCAACACCATCCTCAAACTAAA (SEQ ID NO: 175) | |
| | Product | | 238 |
| Primer Pair 3 | Forward Primer | AGGGTGAGTTAATTGTTTATTGTTGTTT (SEQ ID NO: 176) | |
| Primer Pair 3 | Reverse Primer | ACATACCCACCCTCTAATATATCTCAA (SEQ ID NO: 177) | |
| | Product | | 250 |
| Primer Pair 4 | Forward Primer | AGATTTGTTGGGAGGTAGAG (SEQ ID NO: 180) | |
| Primer Pair 4 | Reverse Primer | AACCAACACCATCCTCA (SEQ ID NO: 181) | |
| | Product | | 242 |
| Primer Pair 5 | Forward Primer | GTAGGGTGAGTTAATTGTTTAT (SEQ ID NO: 182) | |
| Primer Pair 5 | Reverse Primer | CCCTTCTACCCATACTAAAT (SEQ ID NO: 183) | |
| | Product | | 88 |

| | Type | Sequence22 | Amplicon |
|---|---|---|---|
| | Probe-Unmeth | TGGTTATGTTTTAA (SEQ ID NO: 184) | |
| | Probe_meth | TGGTTACCTTTTAA (SEQ ID NO: 185) | |
| Primer Pair 1 | Forward Primer | GGGTAGGAGGTTGTTATTTAGTAGGG (SEQ ID NO: 186) | |
| Primer Pair 1 | Reverse Primer | AAACCAACACCATCCTCAAACT (SEQ ID NO: 187) | |
| | Product | | 130 |
| Primer Pair 2 | Forward Primer | AGGGTGAGTTAATTGTTTATTGTTGTTT (SEQ ID NO: 188) | |
| Primer Pair 2 | Reverse Primer | ACATACCCACCCTCTAATATATCTCAA (SEQ ID NO: 189) | |
| | Product | | 250 |

TABLE 2-continued

List of Probes and Primers

| | | | |
|---|---|---|---|
| Primer Pair 3 | Forward Primer | GGGTAGGAGGTTGTTATTT (SEQ ID NO: 190) | |
| Primer Pair 3 | Reverse Primer | ACATACCCACCCTCTAATA (SEQ ID NO: 191) | |
| | Product | | 165 |
| Primer Pair 4 | Forward Primer | TTAGTATGGGTAGAAGGG (SEQ ID NO: 192) | |
| Primer Pair 4 | Reverse Primer | AAATTCTAACTAAACCACAAA (SEQ ID NO: 193) | |
| | Product | | 124 |

| | Type | Sequence23 | Amplicon |
|---|---|---|---|
| | Probe-Unmeth | TGAGGATGGTGTTG (SEQ ID NO: 194) | |
| | Probe_meth | TGAGGACGGTGTTG (SEQ ID NO: 195) | |
| Primer Pair 1 | Forward Primer | AGGGTGAGTTAATTGTTATTGTTGTTT (SEQ ID NO: 196) | |
| Primer Pair 1 | Reverse Primer | ACATACCCACCCTCTAATATATCTCAA (SEQ ID NO: 197) | |
| | Product | | 250 |
| Primer Pair 2 | Forward Primer | GGGTAGGAGGTTGTTATTTAGT (SEQ ID NO: 198) | |
| Primer Pair 2 | Reverse Primer | AAACATACCCACCCTCTAATA (SEQ ID NO: 199) | |
| | Product | | 167 |
| Primer Pair 3 | Forward Primer | TTTGTGGTTTAGTTAGAATTT (SEQ ID NO: 200) | |
| Primer Pair 3 | Reverse Primer | CCCTCCTCCAAACATAA (SEQ ID NO: 201) | |
| | Product | | 250 |

| | Type | Sequence24 | Amplicon |
|---|---|---|---|
| | Probe-Unmeth | TGGTTTTGGTAGTT (SEQ ID NO: 420) | |
| | Probe_meth | TGGTTTCGGTAGTT (SEQ ID NO: 421) | |
| Primer Pair 1 | Forward Primer | AGGGTGAGTTAATTGTTATTGTTGTTT (SEQ ID NO: 202) | |
| Primer Pair 1 | Reverse Primer | ACATACCCACCCTCTAATATATCTCAA (SEQ ID NO: 203) | |
| | Product | | 250 |
| Primer Pair 2 | Forward Primer | GGGTAGGAGGTTGTTATTTAGT (SEQ ID NO: 204) | |
| Primer Pair 2 | Reverse Primer | AAACATACCCACCCTCTAATA (SEQ ID NO: 205) | |
| | Product | | 167 |
| Primer Pair 3 | Forward Primer | TTAGTTTGAGGATGGTGT (SEQ ID NO: 206) | |
| Primer Pair 3 | Reverse Primer | CCTCCTCCAAACATAATAAA (SEQ ID NO: 207) | |
| | Product | | 229 |
| Primer Pair 4 | Forward Primer | TTTGTGGTTTAGTTAGAATTT (SEQ ID NO: 208) | |
| Primer Pair 4 | Reverse Primer | AAACACTTAAATCTACAATCAT (SEQ ID NO: 209) | |
| | Product | | 161 |

| | Type | Sequence25 | Amplicon |
|---|---|---|---|
| | Probe-Unmeth | AGTTTTGAGATA (SEQ ID NO: 210) | |
| | Probe_meth | AGTTTCGAGATA (SEQ ID NO: 211) | |
| Primer Pair 1 | Forward Primer | TTGAGGATGGTGTTGGTTT (SEQ ID NO: 212) | |
| Primer Pair 1 | Reverse Primer | CACCCTCCTCCAAACATAATAA (SEQ ID NO: 213) | |
| | Product | | 227 |
| Primer Pair 2 | Forward Primer | GGGTAGGAGGTTGTTATTTAGT (SEQ ID NO: 214) | |
| Primer Pair 2 | Reverse Primer | AAACATACCCACCCTCTAATA (SEQ ID NO: 215) | |
| | Product | | 167 |
| Primer Pair 3 | Forward Primer | TTTAGTTTGAGGATGGTG (SEQ ID NO: 216) | |
| Primer Pair 3 | Reverse Primer | AAACACTTAAATCTACAAT CAT (SEQ ID NO: 217) | |
| | Product | | 142 |
| Primer Pair 4 | Forward Primer | TGTGGTTTAGTTAGAATTT (SEQ ID NO: 218) | |
| Primer Pair 4 | Reverse Primer | AATCTACAATCATCAAATAA (SEQ ID NO: 219) | |
| | Product | | 150 |

| | Type | Sequence26 | Amplicon |
|---|---|---|---|
| | Probe-Unmeth | TGGGTATGTTTTT (SEQ ID NO: 220) | |
| | Probe_meth | TGGGTACGTTTTT (SEQ ID NO: 221) | |
| Primer Pair 1 | Forward Primer | TTGAGGATGGTGTTGGTTT (SEQ ID NO: 222) | |
| Primer Pair 1 | Reverse Primer | CACCCTCCTCCAAACATAATAA (SEQ ID NO: 223) | |
| | Product | | 227 |
| Primer Pair 2 | Forward Primer | GGGTAGGAGGTTGTTATTTAGTAGG (SEQ ID NO: 224) | |
| Primer Pair 2 | Reverse Primer | AAACACTTAAATCTACAATCATCAAATAAA (SEQ ID NO: 225) | |
| | Product | | 247 |

TABLE 2-continued

List of Probes and Primers

| | | | |
|---|---|---|---|
| Primer Pair 3 | Forward Primer | GGGTAGGAGGTTGTTATT (SEQ ID NO: 226) | |
| Primer Pair 3 | Reverse Primer | AAACACTTAAATCTACAATCAT (SEQ ID NO: 227) | |
| | Product | | 247 |
| Primer Pair 4 | Forward Primer | TTTAGTTTGAGGATGGTG (SEQ ID NO: 228) | |
| Primer Pair 4 | Reverse Primer | CAAACAAACAACCACAC (SEQ ID NO: 229) | |
| | Product | | 247 |

| | Type | Sequence27 | Amplicon |
|---|---|---|---|
| | Probe-Unmeth | TTATTTGTTTTT (SEQ ID NO: 230) | |
| | Probe_meth | TTATTCGTTTTT (SEQ ID NO: 231) | |
| Primer Pair 1 | Forward Primer | TTTGAGATATATTAGAGGGTGGGTATGT (SEQ ID NO: 232) | |
| Primer Pair 1 | Reverse Primer | AACCCACTCAAACAAACAACCA (SEQ ID NO: 233) | |
| | Product | | 223 |
| Primer Pair 2 | Forward Primer | TTGAGGATGGTGTTGGTTT (SEQ ID NO: 234) | |
| Primer Pair 2 | Reverse Primer | CACCCTCCTCCAAACATAATAA (SEQ ID NO: 235) | |
| | Product | | 227 |
| Primer Pair 3 | Forward Primer | GGGTAGGAGGTTGTTATTTAGTAGG (SEQ ID NO: 236) | |
| Primer Pair 3 | Reverse Primer | AAACACTTAAATCTACAATCATCAAATAAA (SEQ ID NO: 237) | |
| | Product | | 247 |
| Primer Pair 4 | Forward Primer | GGGTAGGAGGTTGTTATT (SEQ ID NO: 238) | |
| Primer Pair 4 | Reverse Primer | AAACACTTAAATCTACAATCAT (SEQ ID NO: 239) | |
| | Product | | 247 |

| | Type | Sequence28 | Amplicon |
|---|---|---|---|
| | Probe-Unmeth | TGTTTTTGTAGTT (SEQ ID NO: 240) | |
| | Probe_meth | TGTTTCGTAGTT (SEQ ID NO: 241) | |
| Primer Pair 1 | Forward Primer | GAGATATATTAGAGGGTGGGTATGTT (SEQ ID NO: 242) | |
| Primer Pair 1 | Reverse Primer | ACACCCTCCTCCAAACATAATAAA (SEQ ID NO: 243) | |
| | Product | | 199 |
| Primer Pair 2 | Forward Primer | GGGATAGTAGTGTAAAGAGTTT (SEQ ID NO: 244) | |
| Primer Pair 2 | Reverse Primer | CCTATCCCTACTCACAACTAAA (SEQ ID NO: 245) | |
| | Product | | 124 |
| Primer Pair 3 | Forward Primer | TGAGGATGGTGTTGGTT (SEQ ID NO: 246) | |
| Primer Pair 3 | Reverse Primer | CACTTAAATCTACAATCATCAAATAAA (SEQ ID NO: 247) | |
| | Product | | 132 |
| Primer Pair 4 | Forward Primer | TTTGTGGTTTAGTTAGAATTT (SEQ ID NO: 248) | |
| Primer Pair 4 | Reverse Primer | AAACACTTAAATCTACAATCAT (SEQ ID NO: 249) | |
| | Product | | 161 |

| | Type | Sequence29 | Amplicon |
|---|---|---|---|
| | Probe-Unmeth | ATGATTGTAGA (SEQ ID NO: 250) | |
| | Probe_meth | ATGATCGTAGA (SEQ ID NO: 251) | |
| Primer Pair 1 | Forward Primer | GAGATATATTAGAGGGTGGGTATGTT (SEQ ID NO: 252) | |
| Primer Pair 1 | Reverse Primer | ACACCCTCCTCCAAACATAATAAA (SEQ ID NO: 253) | |
| | Product | | 199 |

| | Type | Sequence30 | Amplicon |
|---|---|---|---|
| | Probe-Unmeth | TGTTTTATGTTGTTTGT (SEQ ID NO: 254) | |
| | Probe_meth | TGTTTTACGTTGTTTGT (SEQ ID NO: 255) | |
| Primer Pair 1 | Forward Primer | GAGATATATTAGAGGGTGGGTATGTT (SEQ ID NO: 256) | |
| Primer Pair 1 | Reverse Primer | ACACCCTCCTCCAAACATAATAAA (SEQ ID NO: 257) | |
| | Product | | 199 |
| Primer Pair 2 | Forward Primer | TTTATTTGATGATTGTAGATTTAAGTGTTT (SEQ ID NO: 258) | |
| Primer Pair 2 | Reverse Primer | AAACAACCACACCCTCCT (SEQ ID NO: 259) | |
| | Product | | 130 |
| Primer Pair 3 | Forward Primer | TATTTGATGATTGTAGATTT (SEQ ID NO: 260) | |
| Primer Pair 3 | Reverse Primer | CCCATCTCCTAACTATAA (SEQ ID NO: 261) | |
| | Product | | 189 |

| | Type | Sequence31 | Amplicon |
|---|---|---|---|
| | Probe-Unmeth | TTGGGTGAATAT (SEQ ID NO: 262) | |
| | Probe_meth | TTGGGCGAATAT (SEQ ID NO: 263) | |
| Primer Pair 1 | Forward Primer | GAGATATATTAGAGGGTGGGTATGTT (SEQ ID NO: 264) | |

TABLE 2-continued

List of Probes and Primers

| | | | |
|---|---|---|---|
| Primer Pair 1 | Reverse Primer | ACACCCTCCTCCAAACATAATAAA (SEQ ID NO: 265) | |
| | Product | | 199 |
| Primer Pair 2 | Forward Primer | TTTATTTGATGATTGTAGATTTAAGTGTTT (SEQ ID NO: 266) | |
| Primer Pair 2 | Reverse Primer | AAACAACCACACCCTCCT (SEQ ID NO: 267) | |
| | Product | | 130 |
| Primer Pair 3 | Forward Primer | TATTTGATGATTGTAGATTT (SEQ ID NO: 268) | |
| Primer Pair 3 | Reverse Primer | CCCATCTCCTAACTATAA (SEQ ID NO: 269) | |
| | Product | | 189 |
| | Type | Sequence32 | Amplicon |
| | Probe-Unmeth | ATTATGTTTGGAGG (SEQ ID NO: 270) | |
| | Probe_meth | ATTACGTTCGGAGG (SEQ ID NO: 271) | |
| Primer Pair 1 | Forward Primer | TTTATTTGATGATTGTAGATTTAAGTGTTT (SEQ ID NO: 272) | |
| Primer Pair 1 | Reverse Primer | CAAACAAACAACCACACCCT (SEQ ID NO: 273) | |
| | Product | | 135 |
| Primer Pair 2 | Forward Primer | TATTTGATGATTGTAGATTT (SEQ ID NO: 274) | |
| Primer Pair 2 | Reverse Primer | CCCATCTCCTAACTATAA (SEQ ID NO: 275) | |
| | Product | | 189 |
| | Type | Sequence33 | Amplicon |
| | Probe-Unmeth | AGGAGGGTGTGGTTG (SEQ ID NO: 276) | |
| | Probe_meth | AGGAGGGCGTGGTTG (SEQ ID NO: 277) | |
| Primer Pair 1 | Forward Primer | TTGATGATTGTAGATTTAAGTGTTT (SEQ ID NO: 278) | |
| Primer Pair 1 | Reverse Primer | AAATCTAACCCACTCAAACAAA (SEQ ID NO: 279) | |
| | Product | | 144 |
| Primer Pair 2 | Forward Primer | TATTTGATGATTGTAGATTT (SEQ ID NO: 280) | |
| Primer Pair 2 | Reverse Primer | CCCATCTCCTAACTATAA (SEQ ID NO: 281) | |
| | Product | | 189 |
| | Type | Sequence34 | Amplicon |
| | Probe-Unmeth | TTTTGTTGTTAGG (SEQ ID NO: 282) | |
| | Probe_meth | TTTTGTCGTTAGG (SEQ ID NO: 283) | |
| Primer Pair 1 | Forward Primer | TGGTTGTTTGTTTGAGTGGGTTAGA (SEQ ID NO: 284) | |
| Primer Pair 1 | Reverse Primer | ACCCACATATCCCACCTCCTT (SEQ ID NO: 285) | |
| | Product | | 174 |
| Primer Pair 2 | Forward Primer | TTTGGAGGAGGGTGTGGTTG (SEQ ID NO: 286) | |
| Primer Pair 2 | Reverse Primer | AACCTAAACAAATAATCCCAATACTTCTCC (SEQ ID NO: 287) | |
| | Product | | 138 |
| Primer Pair 3 | Forward Primer | GAGGGTGTGGTTGTTTGTTTGA (SEQ ID NO: 288) | |
| Primer Pair 3 | Reverse Primer | CCCAACACCCACATATCCCA (SEQ ID NO: 289) | |
| | Product | | 187 |
| Primer Pair 4 | Forward Primer | TTATGTTTGGAGGAGGGT (SEQ ID NO: 290) | |
| Primer Pair 4 | Reverse Primer | AAACCTAAACAAATAATCCCAATA (SEQ ID NO: 291) | |
| | Product | | 144 |
| Primer Pair 5 | Forward Primer | TGATTGTAGATTTAAGTGTTT (SEQ ID NO: 292) | |
| Primer Pair 5 | Reverse Primer | CCCATCTCCTAACTATAAA (SEQ ID NO: 293) | |
| | Product | | 182 |
| | Type | Sequence35 | Amplicon |
| | Probe-Unmeth | TTTTATGGTAG (SEQ ID NO: 294) | |
| | Probe_meth | TTTTACGGTAG (SEQ ID NO: 295) | |
| Primer Pair 1 | Forward Primer | TGGTTGTTTGTTTGAGTGGGTTAGA (SEQ ID NO: 296) | |
| Primer Pair 1 | Reverse Primer | ACCCACATATCCCACCTCCTT (SEQ ID NO: 297) | |
| | Product | | 174 |
| Primer Pair 2 | Forward Primer | TTTGGAGGAGGGTGTGGTTG (SEQ ID NO: 298) | |
| Primer Pair 2 | Reverse Primer | AACCTAAACAAATAATCCCAATACTTCTCC (SEQ ID NO: 299) | |
| | Product | | 138 |
| Primer Pair 3 | Forward Primer | GAGGGTGTGGTTGTTTGTTTGA (SEQ ID NO: 300) | |
| Primer Pair 3 | Reverse Primer | CCCAACACCCACATATCCCA (SEQ ID NO: 301) | |
| | Product | | 187 |
| Primer Pair 4 | Forward Primer | TTATGTTTGGAGGAGGGT (SEQ ID NO: 302) | |
| Primer Pair 4 | Reverse Primer | AAACCTAAACAAATAATCCCAATA (SEQ ID NO: 303) | |
| | Product | | 144 |

TABLE 2-continued

List of Probes and Primers

| | | | |
|---|---|---|---|
| Primer Pair 5 | Forward Primer | TGATTGTAGATTTAAGTGTTT (SEQ ID NO: 304) | |
| Primer Pair 5 | Reverse Primer | CCCATCTCCTAACTATAAA (SEQ ID NO: 305) | |
| | Product | | 182 |

| | Type | Sequence36 | Amplicon |
|---|---|---|---|
| | Probe-Unmeth | TGTGGGTGTTGGG (SEQ ID NO: 306) | |
| | Probe_meth | TGTGGGCGTTGGG (SEQ ID NO: 307) | |
| Primer Pair 1 | Forward Primer | GGGAGAAGTATTGGGATTATTTGTTTAGGT (SEQ ID NO: 308) | |
| Primer Pair 1 | Reverse Primer | ACACTCCCACCCATCTCCAA (SEQ ID NO: 309) | |
| | Product | | 164 |
| Primer Pair 2 | Forward Primer | GGGAAGGAGGTGGGATA (SEQ ID NO: 310) | |
| Primer Pair 2 | Reverse Primer | CCATCTCCAACCAAACTAAAC (SEQ ID NO: 311) | |
| | Product | | 97 |
| Primer Pair 3 | Forward Primer | GGGAGAAGTATTGGGATTATTTG (SEQ ID NO: 312) | |
| Primer Pair 3 | Reverse Primer | CTACCCACCAACCCTAAATC (SEQ ID NO: 313) | |
| | Product | | 184 |
| Primer Pair 4 | Forward Primer | TTTGTTTGAGTGGGTTAGA (SEQ ID NO: 314) | |
| Primer Pair 4 | Reverse Primer | CCACACTAAATATAAACCTACAA (SEQ ID NO: 315) | |
| | Product | | 199 |
| Primer Pair 5 | Forward Primer | TTTATAGTTAGGAGATGGG (SEQ ID NO: 316) | |
| Primer Pair 5 | Reverse Primer | CCAAACTAAACCCAAATTA (SEQ ID NO: 317) | |
| | Product | | 186 |

| | Type | Sequence37 | Amplicon |
|---|---|---|---|
| | Probe-Unmeth | TTAGTTTGGTTGG (SEQ ID NO: 318) | |
| | Probe_meth | TTAGTTCGGTTGG (SEQ ID NO: 319) | |
| Primer Pair 1 | Forward Primer | GGAGGTGGGATATGTGGGTGT (SEQ ID NO: 320) | |
| Primer Pair 1 | Reverse Primer | ACCTACCCACCAACCCTAAATCA (SEQ ID NO: 321) | |
| | Product | | 124 |
| Primer Pair 2 | Forward Primer | GGGAGAAGTATTGGGATTATTTGTTTAGGT (SEQ ID NO: 322) | |
| Primer Pair 2 | Reverse Primer | ACAATACCCACCTACCCACCAA (SEQ ID NO: 323) | |
| | Product | | 195 |
| Primer Pair 3 | Forward Primer | GTTTGTAGGTTTATATTTAGTGTGGGTGAT (SEQ ID NO: 324) | |
| Primer Pair 3 | Reverse Primer | CTAAATCACACTCCCACCCATCT (SEQ ID NO: 325) | |
| | Product | | 84 |
| Primer Pair 4 | Forward Primer | GGGAAGGAGGTGGGATA (SEQ ID NO: 326) | |
| Primer Pair 4 | Reverse Primer | ACCCTAAATCACACTCCCA (SEQ ID NO: 327) | |
| | Product | | 117 |
| Primer Pair 5 | Forward Primer | GGGAGAAGTATTGGGATTA (SEQ ID NO: 328) | |
| Primer Pair 5 | Reverse Primer | AAACACAATACCCACCTA (SEQ ID NO: 329) | |
| | Product | | 199 |

| | Type | Sequence38 | Amplicon |
|---|---|---|---|
| | Probe-Unmeth | AGTGTGATTTA (SEQ ID NO: 330) | |
| | Probe_meth | AGTGCGATTTA (SEQ ID NO: 331) | |
| Primer Pair 1 | Forward Primer | GGGAGAAGTATTGGGATTATTTGTTTAGGT (SEQ ID NO: 332) | |
| Primer Pair 1 | Reverse Primer | ACAATACCCACCTACCCACCAA (SEQ ID NO: 333) | |
| | Product | | 195 |
| Primer Pair 2 | Forward Primer | AATTTGGGTTTAGTTTGGTTGGAGA (SEQ ID NO: 334) | |
| Primer Pair 2 | Probe | AGTGTGATTTA (SEQ ID NO: 335) | |
| | Reverse Primer | CACCCAACTCCACCTACCC (SEQ ID NO: 336) | |
| Primer Pair 3 | Product | | 169 |
| Primer Pair 3 | Forward Primer | TTTAATTTGGGTTTAGTTTGG (SEQ ID NO: 337) | |
| | Probe | AGTGTGATTTA (SEQ ID NO: 338) | |
| Primer Pair 4 | Reverse Primer | AACACAATACCCACCTAC (SEQ ID NO: 339) | |
| Primer Pair 4 | Product | | 75 |

| | Type | Sequence39 | Amplicon |
|---|---|---|---|
| | Probe-Unmeth | TTGGTGGGTAG (SEQ ID NO: 340) | |
| | Probe_meth | TTGGCGGGTAG (SEQ ID NO: 341) | |
| Primer Pair 1 | Forward Primer | GAGATGGGTGGGAGTGTGATTTA (SEQ ID NO: 342) | |
| Primer Pair 1 | Reverse Primer | CACCCAACTCCACCTACCC (SEQ ID NO: 343) | |
| | Product | | 148 |

TABLE 2-continued

List of Probes and Primers

| | | | |
|---|---|---|---|
| Primer Pair 2 | Forward Primer | TTGGAGATGGGTGGGAGTG (SEQ ID NO: 344) | |
| Primer Pair 2 | Reverse Primer | AAACTACAAACTACCTACACCAAA (SEQ ID NO: 345) | |
| | Product | | 180 |

| | Type | Sequence40 | Amplicon |
|---|---|---|---|
| | Probe-Unmeth | AGGTGGGTA (SEQ ID NO: 346) | |
| | Probe_meth | AGGCGGGTA (SEQ ID NO: 347) | |
| Primer Pair 1 | Forward Primer | GAGATGGGTGGGAGTGTGATTTA (SEQ ID NO: 348) | |
| Primer Pair 1 | Reverse Primer | CACCCAACTCCACCTACCC (SEQ ID NO: 349) | |
| | Product | | 148 |
| Primer Pair 2 | Forward Primer | TTGGAGATGGGTGGGAGTG (SEQ ID NO: 350) | |
| Primer Pair 2 | Reverse Primer | AAACTACAAACTACCTACACCAAA (SEQ ID NO: 351) | |
| | Product | | 180 |
| Primer Pair 3 | Forward Primer | GATTTAGGGTTGGTGGGT (SEQ ID NO: 352) | |
| Primer Pair 3 | Reverse Primer | CCACAATACCACACTTCTACA (SEQ ID NO: 353) | |
| | Product | | 200 |

| | Type | Sequence41 | Amplicon |
|---|---|---|---|
| | Probe-Unmeth | TGTTTTGTTGTTGTT (SEQ ID NO: 354) | |
| | Probe_meth | TGTTTCGTCGTTGTT (SEQ ID NO: 355) | |
| Primer Pair 1 | Forward Primer | GAGATGGGTGGGAGTGTGATTTA (SEQ ID NO: 356) | |
| Primer Pair 1 | Reverse Primer | CACCCAACTCCACCTACCC (SEQ ID NO: 357) | |
| | Product | | 148 |
| Primer Pair 2 | Forward Primer | TTTAGGGTTGGTGGGTAGGT (SEQ ID NO: 358) | |
| Primer Pair 2 | Reverse Primer | TTCCACAATACCACACTTCTACAAA (SEQ ID NO: 359) | |
| | Product | | 200 |
| Primer Pair 3 | Forward Primer | TTGGAGATGGGTGGGAGTG (SEQ ID NO: 360) | |
| Primer Pair 3 | Reverse Primer | AAACTACAAACTACCTACACCAAA (SEQ ID NO: 361) | |
| | Product | | 180 |
| Primer Pair 4 | Forward Primer | GTAGGTGGGTATTGTGTTT (SEQ ID NO: 362) | |
| Primer Pair 4 | Reverse Primer | CTAATACAACATTATTCCACAAT (SEQ ID NO: 363) | |
| | Product | | 200 |

| | Type | Sequence42 | Amplicon |
|---|---|---|---|
| | Probe-Unmeth | TGTTTTGGAAT (SEQ ID NO: 364) | |
| | Probe_meth | TGTTTCGGAAT (SEQ ID NO: 365) | |
| Primer Pair 1 | Forward Primer | GAGATGGGTGGGAGTGTGATTTA (SEQ ID NO: 366) | |
| Primer Pair 1 | Reverse Primer | CACCCAACTCCACCTACCC (SEQ ID NO: 367) | |
| | Product | | 148 |
| Primer Pair 2 | Forward Primer | TTTAGGGTTGGTGGGTAGGT (SEQ ID NO: 368) | |
| Primer Pair 2 | Reverse Primer | TTCCACAATACCACACTTCTACAAA (SEQ ID NO: 369) | |
| | Product | | 200 |
| Primer Pair 3 | Forward Primer | TTGGAGATGGGTGGGAGTG (SEQ ID NO: 370) | |
| Primer Pair 3 | Reverse Primer | AAACTACAAACTACCTACACCAAA (SEQ ID NO: 371) | |
| | Product | | 180 |
| Primer Pair 4 | Forward Primer | GTAGGTGGGTATTGTGTTT (SEQ ID NO: 372) | |
| Primer Pair 4 | Reverse Primer | CTAATACAACATTATTCCACAAT (SEQ ID NO: 373) | |
| | Product | | 200 |

| | Type | Sequence43 | Amplicon |
|---|---|---|---|
| | Probe-Unmeth | TTTTGTGTGGTATGTTTT (SEQ ID NO: 374) | |
| | Probe_meth | TTTTGCGCGGTATGTTTT (SEQ ID NO: 375) | |
| Primer Pair 1 | Forward Primer | GAGATGGGTGGGAGTGTGATTTA (SEQ ID NO: 376) | |
| Primer Pair 1 | Reverse Primer | CACCCAACTCCACCTACCC (SEQ ID NO: 377) | |
| | Product | | 148 |
| Primer Pair 2 | Forward Primer | TTTAGGGTTGGTGGGTAGGT (SEQ ID NO: 378) | |
| Primer Pair 2 | Reverse Primer | TTCCACAATACCACACTTCTACAAA (SEQ ID NO: 379) | |
| | Product | | 200 |
| Primer Pair 3 | Forward Primer | TTGGAGATGGGTGGGAGTG (SEQ ID NO: 380) | |
| Primer Pair 3 | Reverse Primer | AAACTACAAACTACCTACACCAAA (SEQ ID NO: 381) | |
| | Product | | 180 |

TABLE 2-continued

List of Probes and Primers

| | | | |
|---|---|---|---|
| Primer Pair 4 | Forward Primer | GTAGGTGGGTATTGTGTTT (SEQ ID NO: 382) | |
| Primer Pair 4 | Reverse Primer | CTAATACAACATTATTCCACAAT (SEQ ID NO: 383) | |
| | Product | | 200 |

| | Type | Sequence45 | Amplicon |
|---|---|---|---|
| | Probe-Unmeth | TTGGGTGGGGT (SEQ ID NO: 384) | |
| | Probe_meth | TTGGGCGGGGT (SEQ ID NO: 385) | |
| Primer Pair 1 | Forward Primer | TTTAGGGTTGGTGGGTAGGT (SEQ ID NO: 386) | |
| Primer Pair 1 | Reverse Primer | TTCCACAATACCACACTTCTACAA (SEQ ID NO: 387) | |
| | Product | | 200 |
| Primer Pair 2 | Forward Primer | GATGGGTGGGAGTGTGATT (SEQ ID NO: 388) | |
| Primer Pair 2 | Reverse Primer | AAACTACAAACTACCTACACCAAA (SEQ ID NO: 389) | |
| | Product | | 175 |
| Primer Pair 3 | Forward Primer | GTAGGTGGGTATTGTGTTT (SEQ ID NO: 390) | |
| Primer Pair 3 | Reverse Primer | CTAATACAACATTATTCCACAAT (SEQ ID NO: 391) | |
| | Product | | 200 |

| | Type | Sequence46 | Amplicon |
|---|---|---|---|
| | Probe-Unmeth | TAGAAGTGTGGTA (SEQ ID NO: 392) | |
| | Probe_meth | TAGAAGCGTGGTA (SEQ ID NO: 393) | |
| Primer Pair 1 | Forward Primer | TTTGGTGTAGGTAGTTTGTAGTTT (SEQ ID NO: 394) | |
| Primer Pair 1 | Reverse Primer | AACTTTATTCCATCTCTCTCAATACA (SEQ ID NO: 395) | |
| | Product | | 182 |
| Primer Pair 2 | Forward Primer | GGGTAGGTGGAGTTGGGT (SEQ ID NO: 396) | |
| Primer Pair 2 | Reverse Primer | AACAAATACTAATACAACATTATTCCACAA (SEQ ID NO: 397) | |
| | Product | | 112 |
| Primer Pair 3 | Forward Primer | TTTGGTGTAGGTAGTTT (SEQ ID NO: 398) | |
| Primer Pair 3 | Reverse Primer | CAATAATTCTCCAACTAATAAA (SEQ ID NO: 399) | |
| | Product | | 113 |

| | Type | Sequence47 | Amplicon |
|---|---|---|---|
| | Probe-Unmeth | ATTAGATGTAGTT (SEQ ID NO: 400) | |
| | Probe_meth | ATTAGACGTAGTT (SEQ ID NO: 401) | |
| Primer Pair 1 | Forward Primer | TGTAGAAGTGTGGTATTGTGGAATAAT (SEQ ID NO: 402) | |
| Primer Pair 1 | Reverse Primer | AAACTTTATTCCATCTCTCTCAATACAAA (SEQ ID NO: 403) | |
| | Product | | 140 |
| Primer Pair 2 | Forward Primer | TTTGTAGAAGTGTGGTATTGT (SEQ ID NO: 404) | |
| Primer Pair 2 | Reverse Primer | AAACTTTATTCCATCTCTCTCA (SEQ ID NO: 405) | |
| | Product | | 142 |

| | Type | Sequence48 | Amplicon |
|---|---|---|---|
| | Probe-Unmeth | TAGTTTGTAGG (SEQ ID NO: 406) | |
| | Probe_meth | TAGTTCGTAGG (SEQ ID NO: 407) | |
| Primer Pair 1 | Forward Primer | TGTAGAAGTGTGGTATTGTGGAATAAT (SEQ ID NO: 408) | |
| Primer Pair 1 | Reverse Primer | AAACTTTATTCCATCTCTCTCAATACAAA (SEQ ID NO: 409) | |
| | Product | | 140 |
| Primer Pair 2 | Forward Primer | TTTGTAGAAGTGTGGTATTGT (SEQ ID NO: 410) | |
| Primer Pair 2 | Reverse Primer | AAACTTTATTCCATCTCTCTCA (SEQ ID NO: 411) | |
| | Product | | 142 |

| | Type | Sequence49 | Amplicon |
|---|---|---|---|
| | Probe-Unmeth | ATTTGTTGTTTT (SEQ ID NO: 412) | |
| | Probe_meth | ATTCGTCGTTTT (SEQ ID NO: 413) | |
| Primer Pair 1 | Forward Primer | GTAGAAGTGTGGTATTGTGGAATAAT (SEQ ID NO: 414) | |
| Primer Pair 1 | Reverse Primer | AAACTTTATTCCATCTCTCTCAATACA (SEQ ID NO: 415) | |
| | Product | | 139 |
| Primer Pair 2 | Forward Primer | TTGTAGAAGTGTGGTATTG (SEQ ID NO: 416) | |
| Primer Pair 2 | Reverse Primer | AAACTTTATTCCATCTCTCT (SEQ ID NO: 417) | |
| | Product | | 141 |

EXEMPLIFICATION

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Experimental Design

All CpG sites for the human insulin gene (hg19_knownGene_uc021qcd.1 range=chr11:2181009-2182439) were mapped. The sequence was then transformed to a sequence representing bisulfate-treated DNA, where all Cs are converted to Ts and in the case of a methylated CpG site, the C is protected from conversion to T. The probes were designed to include two CpG sites at nucleotides 21814010 and 21814012 in positions +396 and +399 from the transcription start site.

The nucleotide sequence of the methylation sensitive probe is: ATTTAAGATTTGTTGGGAGGTAGAG (SEQ ID NO: 1) and the nucleotide sequence of the methylation insensitive probe is: ATTTAAGATTCGTCGGGAGGTAGAG (SEQ ID NO: 2). The sequences of the forward and reverse primers are: GTGGTTTATATTTGGTGGA (SEQ ID NO: 5) and ATTAACTCACCCTACAAATC (SEQ ID NO: 6).

To increase sensitivity, specificity and to reduce background fluorescence, the probes were designed with an internal Zen quencher (ZEN) in addition to the 3' Iowa Black FQ quencher (3IABkFQ). The ZEN probes were synthesized by Integrated DNA Technologies.

The synthetic L2_M (SEQ ID NO: 419) and L2_UM (SEQ ID NO: 418) sequences, which are replicas of bisulfite-treated methylated and un-methylated human insulin gene sequences (region 2181155-2181465 on Chr11), respectively, were cloned into pUC57 plasmids (Genewiz, Inc).

FIG. 1 illustrates the cloned sequences in pUC57 Kan plasmid. The plasmids were used for optimization of PCR conditions and to determine the sensitivity and specificity of the primers and probes.

Reaction mixtures of 25 µl volume, comprising 1× Droplet PCR supermix, (BioRad), 900 µM primer mix, 250 µM probe mix, 5 µl of plasmid (copy number ranging from 100,000 to 1 and mixed populations of un-methylated and methylated plasmids) or 4 µl of bisulfite treated genomic DNA from either serum, islet cells or peripheral blood mononuclear cells (PBMCs) was prepared. Twenty µl of the PCR reaction mix was loaded into a separate well of an eight channel droplet generator cartridge, and in a separate corresponding well 70 µl of droplet generation oil (BioRad) was loaded. The cartridge was loaded into a droplet generator (Biorad). Forty µl of the generated droplets were carefully transferred to a 96 well PCR plate and the PCR reaction was run on a thermal cycle with the following protocol: 10 min activation at 95° C. followed by 40 cycles of a two-step amplification protocol of 30 seconds at 94° C. denaturation and 60 seconds at 58° C. for a combined annealing-extension step. A final 10 min at 98° C. inactivation step completed the reaction.

The PCR plate was then transferred to a Qx100 droplet reader (Biorad), which automatically reads the droplets from each well of the plate. Analysis of ddPCR data was performed using QuantaSoft Analysis software.

Islet, PBMCs and serum samples from non-diabetic and diabetic patients were used to validate the protocol developed using the plasmids. DNA was isolated using the Qiagen blood and tissue DNA extraction kit. DNA was bisulfite treated using an EZ DNA Methylation kit (Zymo Research, Irvine, Calif.).

Limit of detection assays were performed with plasmids, islets and PBMCs. The plasmid suspensions were made in a series of 10 fold serial dilutions from 100,000 copies to 1 copy. Bisulfite-treated DNA from islets and PBMCs were diluted over a ¼ dilution series up to 1/1024 with amounts ranging from 148 ng to 0.1 ng.

Results

In the multiplexed assay, the probe for unmethylated human insulin gene DNA successfully detected 1 copy/µl of plasmid and showed no cross amplification with the plasmid representing methylated DNA. The probe for methylated DNA successfully detected 1 copy/µl per reaction and showed minimal cross amplification only with high numbers of plasmid representing un-methylated insulin gene DNA.

In the recovery assay, where approximately 3000 copies/µl of L2_M plasmid were mixed with 10 copies of the L2_UM plasmid, the ddPCR successfully detected the L2_UM plasmid successfully.

Using human islet tissue and PBMCs, we were able to detect unmethylated insulin DNA in as low as 0.1 ng of DNA. Also, the ratio of methylated insulin DNA to unmethylated insulin DNA did not change over varying concentrations. We then tested the assay with clinical samples, and were able to detect unmethylated DNA in pre-diabetics. Also, the ratio of unmethylated insulin coding DNA to methylated insulin DNA was significantly elevated in pre-diabetic (mean 0.4264±0.04034 N=6) patients compared to non-diabetic human controls (0.2122±0.02449 N=13).

Example 2

Development of IGRP β Cell Death Assay.

Figure 2:
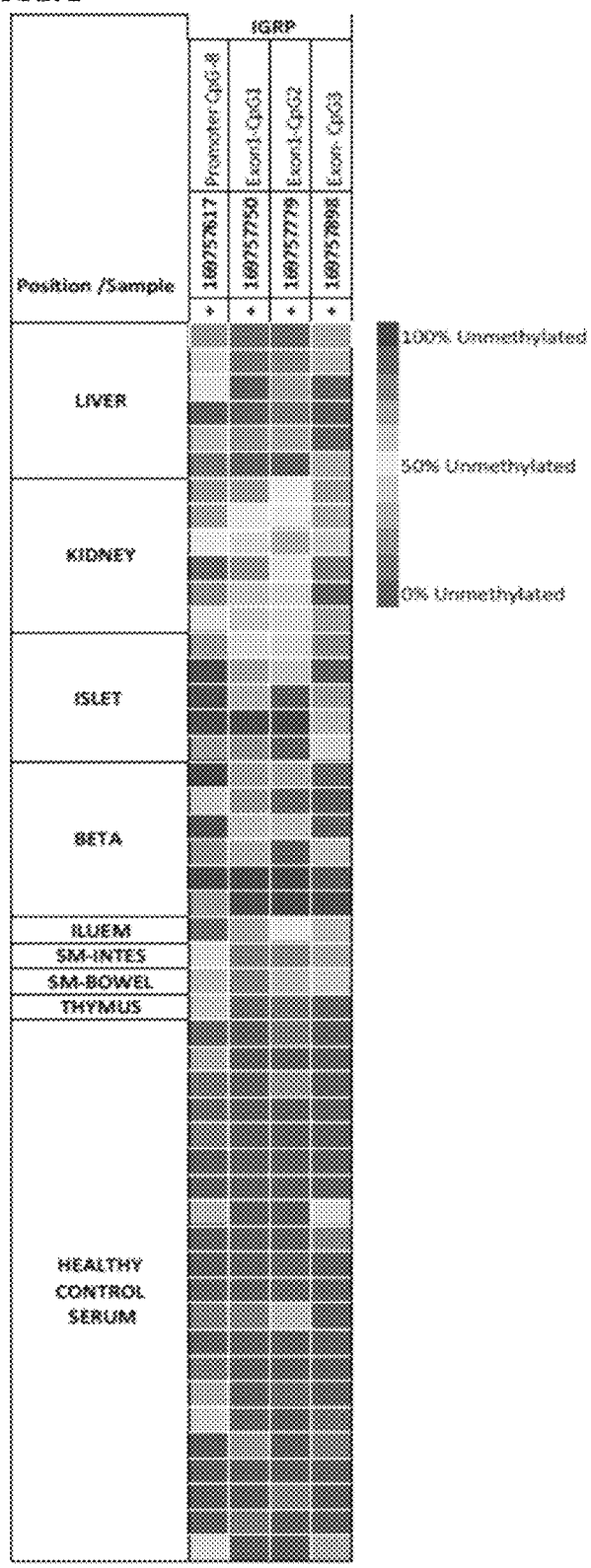
FIG. 2 depicts a heat map representing the level of methylation across four islet specific glucose-6-phosphatase catalytic subunit-related proteins (IGRP) CpG sites amongst different samples.

1) The islet-specific glucose-6-phosphatase catalytic subunit-related protein (IGRP) gene was sequenced using MethylSeq. Forty-eight (48) human samples were processed and analyzed using Zymo's Targeted Bisulfite Sequencing Full Service amplicon design, library preparation, sequencing, and bioinformatics pipeline. Data generated from the sequencing identified several CpG sites (FIG. 2) for further assay development. Several primer pairs and probe combinations were designed for the 4 most promising sites on the IGRP gene (Table 3). All reactions were developed on the Droplet digital PCR. (ddPCR). Data from the ddPCR was expressed as a ratio of the copy numbers of PCR products using a probe specific for unmethylated CpG sites and methylated+unmethylated CpG sites. In certain embodiments, the sequences have a MGB tag attached to them to increase the melting temperature. In certain embodiments, the sequences have a double quencher added to them for reducing the background fluorescence (ZEN from Integrated DNA Technologies (IDT)). In all embodiments, all probes are labeled with either FAM, HEX, or VIC dye.

TABLE 3

List of Primers and Probes for 4 CpG sites across IGRP gene

| Name | Type | Sequence (5'-3') | Amplicon |
|---|---|---|---|
| IGRP_P8_UM | Probe-Unmeth | TTTTTTTGAATTG (SEQ ID NO: 422) | |
| IGRP_P8_M | Probe-Meth | TTTTTTCGAATTG (SEQ ID NO: 423) | |
| IGRP_P8.1_FWD | Primer | GGAGGTTGTATAAGAAATTTATTG TGTTT (SEQ ID NO 424) | |
| IGRP_P8.1_REV | Primer | ACCAACCCTCCTCTACTAAATAAC (SEQ ID NO: 425) | |
| | Product | | 134 bp |
| IGRP_EX1-1_UM | Probe-Unmeth | AATGGTTTGATATGT (SEQ ID NO: 426) | |
| IGRP_EX1-1_M | Probe-Meth | AATGGTTCGATATGT (SEQ ID NO: 427) | |
| IGRP_EX1-1.1FWD | Primer | GATGAGTTATTTAGTAGAGGAG (SEQ ID NO: 428) | |
| IGRP_EX1-1.1REV | Primer | ACTCTAATTCCCACCTTT (SEQ ID NO: 429) | |
| | Product | | 120 bp |
| IGRP_EX1-2_UM | Probe-Unmeth | ATAAAAATGGTGGGA (SEQ ID NO: 430) | |
| IGRP_EX1-2_M | Probe-Meth | ATAAAAACGGTGGGA (SEQ ID NO: 431) | |
| IGRP_EX1-2.1 | FWD Primer | ATGGTTTGATATGTTATAAAGG (SEQ ID NO: 432) | |
| IGRP_EX1-2.1 | REV Primer | TATAAACACTCCATTCCTATAA (SEQ ID NO: 433) | |
| | Product | | 130 bp |
| IGRP_EX1-3_UM | Probe-Unmeth | AGGATTATTGAGTTTAT (SEQ ID NO: 434) | |
| IGRP_EX1-3_M | Probe-Meth | AGGATTATCGAGTTTAT (SEQ ID NO: 435) | |
| IGRP_EX1-3.1_FWD | Primer | TTTATAGGAATGGAGTGTTTA (SEQ ID NO: 436) | |
| IGRP_EX1-3.1_REV | Primer | AAATCTCCAACATTAAACATAA (SEQ ID NO: 437) | |
| | Product | | 94 bp |

2) Measurement of Unmethylated/Total IGRP DNA:

DNA was purified from 200 µl to 500 µl of serum using cfDNA Kit as suggested by the manufacturer (Zymo Research, Irvine, Calif.), with a modified incubation period of 20 min at 45° C. in the final step. DNA was bisulfite treated using EZ DNA Methylation Kit (Zymo Research, Irvine, Calif.). Each 25 µl volume of PCR reaction consisted of 1× Droplet PCR supermix (BioRad, Hercules, Calif.), 900 nM of each primer, 250 nM of each probe (Table 3), and 5 µl of sample (bisulfite treated DNA). A no-template control (NTC) reaction was run in parallel. Twenty 0 of each PCR reaction mix was loaded into separate wells of an eight channel droplet generator cartridge and 70 µl of droplet generation oil (BioRad Hercules, Calif.) was loaded in a separate corresponding well. The cartridge was then loaded into a droplet generator (Biorad, Hercules, Calif.). Forty µl of the generated droplets were transferred to a 96 well PCR plate. The plate was heat sealed and the PCR reaction run on a thermal cycler with the following protocol: 10 min activation at 95° C. followed by 40 cycles of a two-step amplification protocol (30 s at 94° C. denaturation and 60 s at 50° C., or appropriate annealing temperature of the primers and probe). A final 10 min at 98° C. inactivation step was used to complete the reaction. The PCR plate was then transferred to a QX200 droplet reader (Biorad, Hercules, Calif.), and the reaction products were analyzed with QuantaSoft (Bio-Rad) Analysis software. Discrimination between droplets that contain the target (positives) and those that do not (negatives) was done by applying a fluorescence amplitude threshold based on the amplitude read from the negative template control (NTC) well in QuantaSoft (Bio-Rad, Hercules, Calif.). Using a Poisson distribution, the number of unmethylated and methylated copy numbers per microliter of sample was calculated. For each sample, the ratio of unmethylated IGRP DNA to that of total IGRP DNA was calculated. Very low yields of DNA can result in artifact ratios because small differences in droplets are magnified when the ratio is calculated. The quality control in the analysis described herein eliminates samples in which the starting material had extensive degradation. Samples with less than 1 copy/µl were not used for analysis. Each ddPCR plate incorporated plasmid controls and biological controls consisting of liver and islet DNAs. The ratios for each of the controls was known, and therefore, if on any plate run the ratios do not fall within the known ranges, the experiment was repeated. Such a plate run failure was extremely rare. Characterization of the IGRP Assay Performance with Plasmid Controls.

Figure 3:
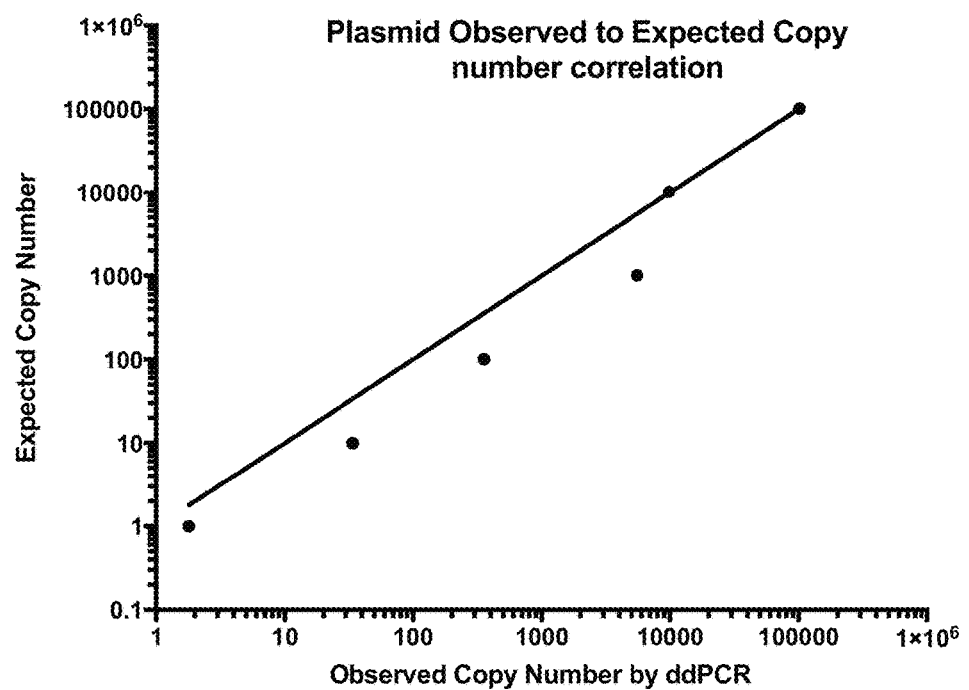
FIG. 3 is a graph showing a linear regression correlation curve: $R^2=0.998$ and slope=0.99±0.019, p<0.0001. A correlation in copy number was observed between the input plasmid copy number and the copy number calculated from the ddPCR results.

Two plasmids were constructed and designed with synthetic DNA sequences that were identical to bisulfite-treated methylated and unmethylated sequences of the IGRP DNA. To determine the linearity, specificity and sensitivity over the theoretical dynamic range of ddPCR, a four-fold dilution series for each plasmid was prepared. The ddPCR response was linear with concentration of targets ranging from approximately 5000 copies/µl to 1 copy/µl. Linear regression correlation coefficients ($r^2$) for the log transformed copy number between ddPCR and the plasmid dilution series was 0.998, with a slope of 0.99±0.019, p<0.0001 (FIG. 3, data is shown only for probe Ex_1-2.1).

Figure 4:
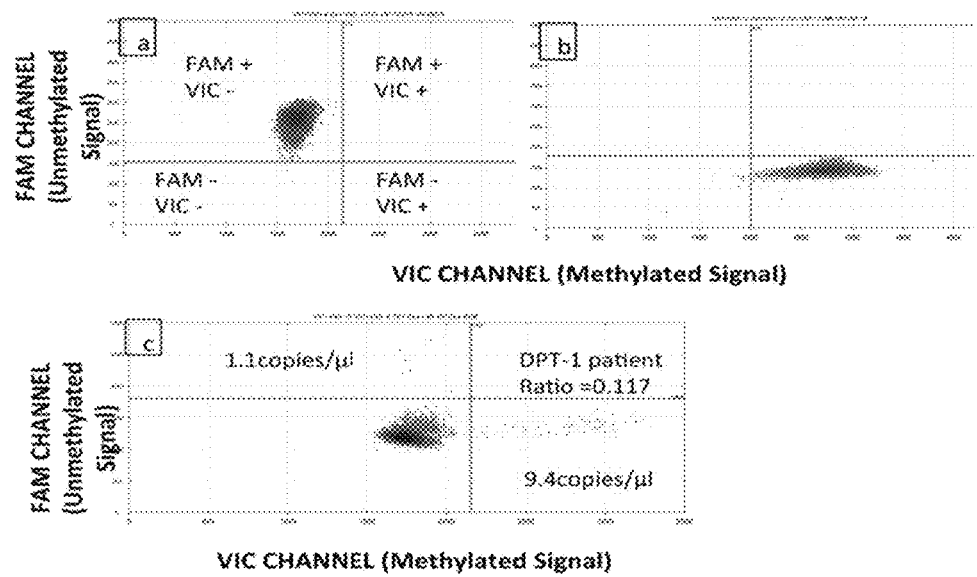
FIG. 4 contains three panels, a, b, and c. Panel a is a graph showing specificity of the Exon1_2.1IGRP ddPCR assay. Even at saturating concentrations of unmethylated target (blue droplets), no droplets were seen in the VIC channel (green) and (b) at saturating concentrations of methylated target (green droplets), no droplets were seen in the VIC channel (green) and in the FAM channel. Panel c indicates the sensitivity of the IGRP probe to detect 1 copy of unmethylated target DNA in a complex biological patient serum sample.

To determine the specificity of the assay, it was tested to determine if the probe that targets the unmethylated CpG of the gene would pick up the methylated target. At saturating levels of the methylated plasmid, the unmethylated probe did not amplify the methylated plasmid and at saturating levels of unmethylated plasmid the methylated probe did not amplify the unmethylated plasmid (FIGS. 4a and 4b, data is shown for Ex_1-2.1 probe). Given that the difference between the unmethylated target to methylated target was one nucleotide, a highly specific assay was developed on the ddPCR platform. The assay was also sensitive enough to pick up 1 copy/µl of unmethylated IGRP DNA in a complex biological serum sample as demonstrated in FIG. 4c (data is shown for Ex_1-2.1 probe).

Test of Specificity for the IGRP Probes with Biological Samples.

Once the technical aspects of the assays had been developed, the applicability of these four probes were tested with human tissue and serum samples. Given the prior experience with INS gene, the ratios of the four IGRP probes were evaluated across serum samples from healthy control subjects (HC), liver, islets and β cells. Three out for the four probes gave very low ratios for healthy serum samples while assay Pr8.1-1 gave HC ratios closer to that seen with the INS gene. The ratios from β cells was much higher across all assays (0.955 to 0.911, Table 4) compared to INS gene ratios (unmeth/total ratio=0.8). This confirmed the sequencing data results, that the selected IGRP CpGs were mostly methylated across all tissues and unmethylated in β cells. Based on the results from biological samples and the technical performance of the assay, IGRP Ex_1-2.1 (corresponding to SEQ ID NOs: 430-433) was chosen as the lead probe to test baseline responses from non-diabetic, diabetic and at risk populations.

TABLE 4

Ratios (unmethylated/total copy number) from Healthy controls serum samples (HC), liver, islets and beta cells.

| Sample/CpG | Pr-8.1-1 | EX_1-1.1 | EX_1-2.1 | EX_1-3.1 |
|---|---|---|---|---|
| HC1 | 0.184 | 0.044 | 0.052 | 0.047 |
| HC2 | 0.199 | 0.039 | 0.056 | 0.066 |
| HC3 | 0.126 | 0.023 | 0.042 | 0.052 |
| HC4 | 0.221 | 0.030 | 0.021 | 0.040 |
| HC5 | 0.113 | 0.008 | 0.010 | 0.087 |
| HC6 | 0.133 | 0.045 | 0.066 | 0.106 |
| Islets | 0.766 | 0.131 | 0.482 | 0.248 |
| Liver | 0.479 | 0.065 | 0.204 | 0.083 |
| Beta Cells | 0.955 | 0.911 | 0.941 | 0.919 |

Figure 5:
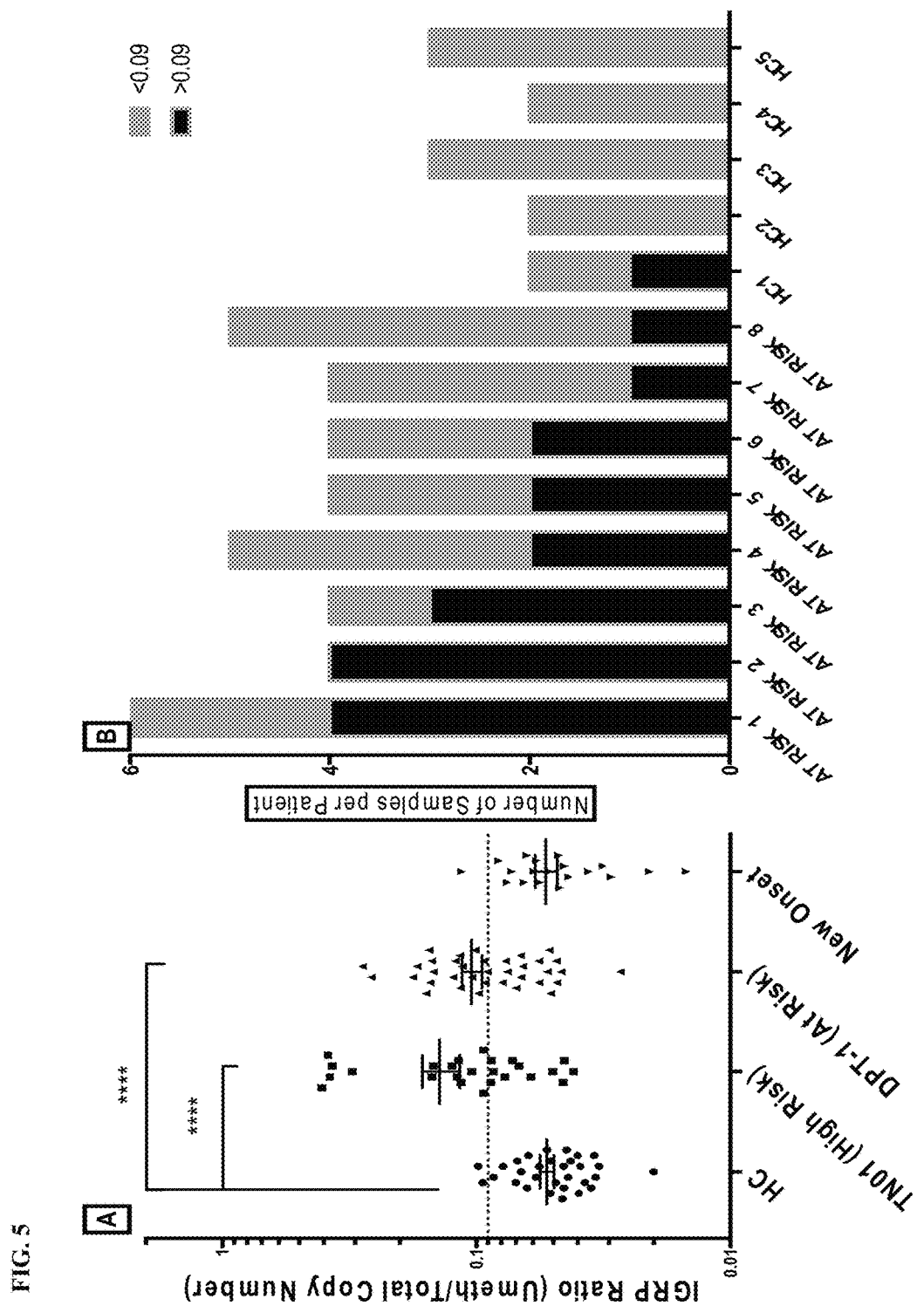
FIG. 5 contains two panels showing analysis of unmethylated IGRP DNA ratios in patients. Panel a shows samples from subjects at high risk for T1D (TN01), at risk DPT-1 cohort and from new onsets were compared with samples from healthy controls (HCs). The median+interquartile range is shown (p=0.0001 by Kruskal-Wallis test for HC versus TN01 and p=0.0001 for HC versus DPT-1). Panel b depicts that 8/8 DPT-1 subjects showed elevated ratios in least at one time point in follow up compared to 1/5 healthy controls (p=0.007, Fisher's exact test).

Analysis of β Cell Killing with the Ex 1.2.1 IGRP Probe in Subjects At-Risk for T1D:

The ratio of unmethylated/methylated IGRP DNA was compared in serum of 19 individuals with recent onset T1D (up to 1 year after diagnosis), 8 participants (36 samples) in the Diabetes Prevention Trial-1 (DPT-1), and 26 individuals identified in the TrialNet TN01 study as "high-risk". The DPT-1 and TN01 subjects do not have diabetes but are relatives of patients with T1D, and have at least 1+ autoantibody. The DPT-1 (at-risk) subjects were followed for up to 6 years and about 3 samples were obtained from each subject. The TN01 (high-risk) individuals had 2+ or more autoantibodies and also had dysglycemia during an Oral Glucose Tolerance Test (OGTT). The participants were largely children, and were compared to age matched HCs (FIG. 5A). When the 26 samples from the TN01 high-risk subjects were used for the calculations, the average ratios of unmethylated/total ratios for IGRP DNA was found to be significantly higher compared to controls (FIG. 5A, p<0.0001). In the TN01 high risk subjects, analyzed on a single occasion, 15/26 measurements were above 0.09. The new onsets all had IGRP unmethylated/total similar to HCs probably due to the significant loss of β cells in these children as a result of T1D and consistent with our published findings that most β cell killing occurs prior to clinical disease presentation. Also, 8/8 patients in the DPT-1 trial had an elevated IGRP ratio at least once during their longitudinal sampling (FIG. 5B).

Figure 6:
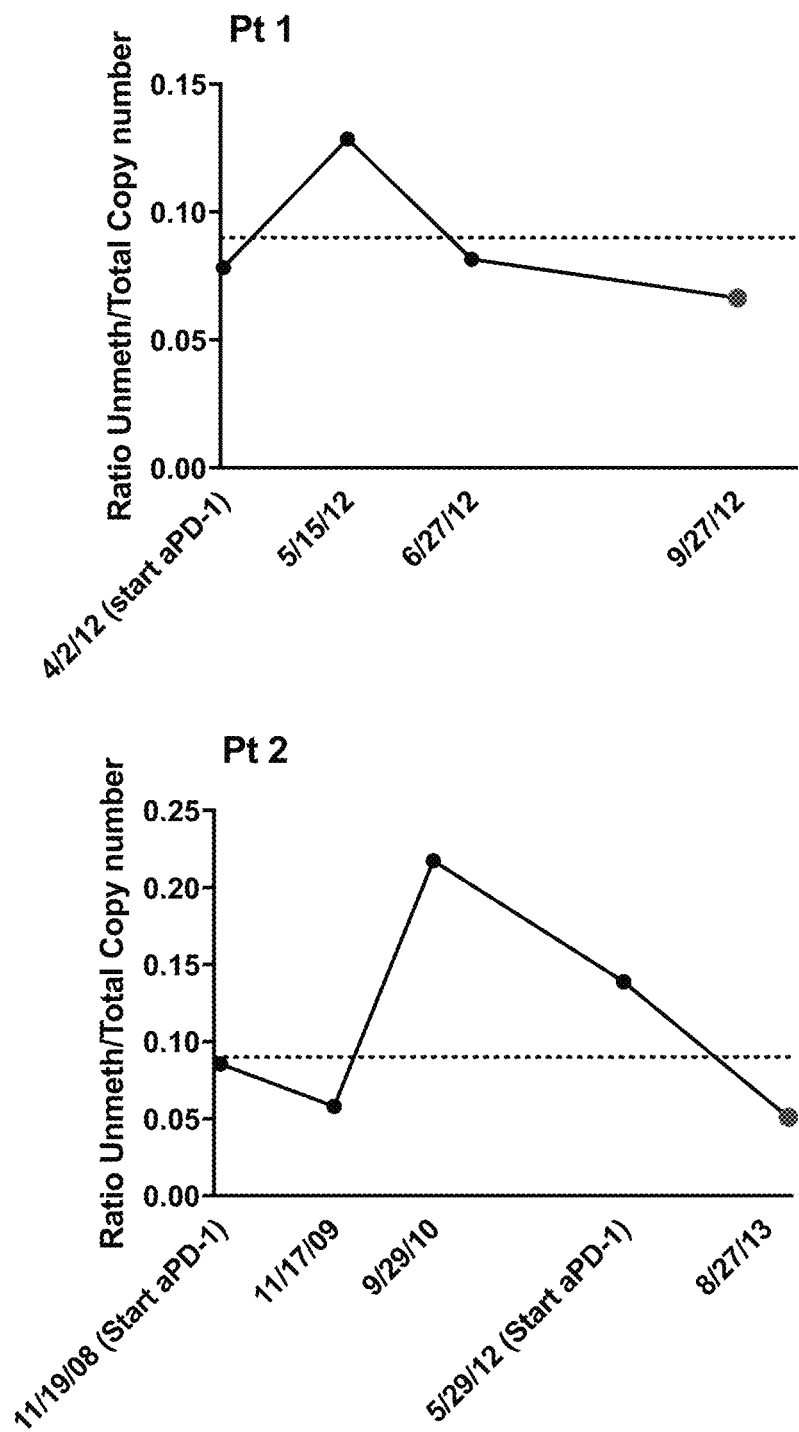
FIG. 6 shows the analysis of IGRP ratio in two patients who received anti-PD-1 therapy and went on to develop diabetes. Both Patient 1 and 2 showed elevated ratios before developing diabetes as indicated by the red dot in the graph.

Elevated β Cell Killing after Checkpoint Inhibitor (CPI) Treatment:

Two patients were studied who developed insulin dependent diabetes after they were treated with anti-PD-1 or anti-PD-L1 CPIs for melanoma. In these two subjects, ages 56 and 68, an increase in the ratio of unmethylated/total IGRP DNA occurred about 2 and 22 months after a first course of anti-PD-1+anti-CTLA-4 and an extended course of anti-PD-1 treatment (FIG. 6). For Pt2, a course of nivolumab was stopped and then re-administered 18 months prior to the onset of hyperglycemia.

In summary, the work described herein in patients with T1D, and preliminary data in patients with cancers treated with CPI suggested that β cell killing that occurred in vivo prior to the onset of hyperglycemia can be detected. These studies described herein from patients with cancers who were treated with CPIs indicated that this measurement may identify individuals who will develop diabetes prior to its clinical onset. The assay, therefore, may fulfill an important unmet medical need. First, it was designed to identify patients who were developing β cell destruction and were likely to present with insulin dependent diabetes before they develop more serious manifestations of the disease. In this regard, a measure of β cell death that can be performed on a serum sample would represent an important addition to other laboratory tests used to monitor patients. Second, the analysis may shed light on immune responses to CPI therapy. Anti-tumor responses may be improved in those who received CPI and developed diabetes or β cell killing. Finally, understanding the kinetics of this adverse event and in whom it occurs may suggest new therapeutic strategies that may prevent the autoimmune events while enabling the anti-tumor responses. Therefore, based on this understanding of the mechanism of CPI, and the findings presented herein, therapies may be tailored to avoid the complications of autoimmunity, which can be monitored with the compositions and methods described herein.

INCORPORATION BY REFERENCE

The contents of all references, patent applications, patents, and published patent applications, as well as the Figures and the sequences, cited throughout this application are hereby incorporated by reference in their entirety as if each individual publication or patent was specifically and individually incorporated by reference. In case of conflict, the present application, including any definitions herein, may control.

EQUIVALENTS

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention may become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method of diagnosing whether a subject has or is at risk of developing type 1 diabetes comprising the steps of:
   (a) isolating genomic islet-specific glucose-6-phosphatase catalytic subunit-related (IGRP) DNA from a biological sample comprising serum obtained from a subject and treating the isolated DNA with bisulfate;
   (b) contacting the bisulfite-treated DNA with an appropriate amount of a composition comprising a combination recombinant, double quencher probe pair and primer pair containing nucleotide sequences indicative of the methylation status of said bisulfite-treated DNA to form a reaction mixture, wherein said probe pair comprises a first probe and a second probe,
   said first probe comprising a fluorescent dye at the 5' end of the first probe, a first quencher inserted within the first probe, and a second quencher at the 3' end of the first probe,
   said second probe comprising a fluorescent dye at the 5' end of the second probe, a first quencher inserted within the second probe, and a second quencher at the 3' end of the second probe, and
   said first probe and said second probe comprise different fluorescent dyes;
   (c) loading the reaction mixture into a droplet generator;
   (d) depositing the droplets generated onto a plate and transferring the plate into a polymerase chain reactor for amplification by droplet digital polymerase chain reaction (ddPCR);
   (e) transferring the plate into a droplet reader for analysis of the ddPCR;
   (f) detecting the ratio of unmethylated IGRP DNA copy number to total or methylated IGRP DNA copy number; and
   (g) diagnosing the subject as having or at risk of developing type I diabetes where said subject has an increased ratio of unmethylated IGRP DNA copy number to total or methylated IGRP DNA copy number compared to a control value.

2. The method of claim 1, wherein the combination probe pair comprises a probe to detect unmethylated IGRP (unmethylated probe) and a probe to detect methylated IGRP (methylated probe).

3. The method of claim 2, wherein the unmethylated probe is selected from the group consisting of the nucleotide sequence set forth in SEQ ID NO: 422, 426, 430, and 434, or combination thereof.

4. The method of claim 2, wherein the methylated probe is selected from the group consisting of the nucleotide sequence set forth in SEQ ID NO: 423, 427, 431, and 435, or combination thereof.

5. The method of claim 2, wherein the unmethylated and methylated probe is selected from the group consisting of the nucleotide sequence set forth in SEQ ID NO: 422, 423, 426, 427, 430, 431, 434, and 435, or combination thereof.

6. The method of claim 2, wherein the primer is selected from the group consisting of the nucleotide sequences set forth in SEQ ID NO: 424, 425, 428, 429, 432, 433, 436, and 437, or combination thereof.

7. The method of claim 2, wherein the probe pair is selected from the group consisting of SEQ ID NOs: 422 and 423, SEQ ID NOs: 426 and 427, SEQ ID NOs: 430 and SEQ ID NOs: 431, and 434 and 435.

8. The method of claim 2, wherein the primer pair is selected from the group consisting of SEQ ID NOs: 424 and 425, SEQ ID NOs: 428 and 429, SEQ ID NOs: 432 and 433, and SEQ ID NOs: 436 and 437.

9. The method of claim 2, wherein the combination probe pair and primer pair is selected from the group consisting of SEQ ID NOs: 422-425; SEQ ID NOs: 426-429; SEQ ID NOs: 430-433; and SEQ ID NOs: 434-437.

10. The method of claim 9, wherein the combination probe pair and primer pair is SEQ ID NOs: 422-425.

11. The method of claim 9, wherein the combination probe pair and primer pair is SEQ ID NOs: 426-429.

12. The method of claim 9, wherein the combination probe pair and primer pair is SEQ ID NOs: 430-433.

13. The method of claim 9, wherein the combination probe pair and primer pair is SEQ ID NOs: 434-437.

14. The method of claim 2, wherein the subject has received or is receiving an anti-cancer therapy or chemotherapy, has undergone or is undergoing an anti-cancer therapy or chemotherapy, or is suffering from cancer.

15. The method of claim 2, wherein the subject is a mammal.

16. The method of claim 15, wherein the subject is human.

17. The method of claim 1, wherein the control value is the ratio of unmethylated IGRP DNA copy number to total or methylated IGRP DNA copy number detected in a healthy or non-diabetic subject, or a reference value.

* * * * *